US011155639B2

(12) United States Patent
Kim et al.

(10) Patent No.: US 11,155,639 B2
(45) Date of Patent: Oct. 26, 2021

(54) METHOD FOR PRODUCING ANTIBODY CH3 DOMAIN HETERODIMERIC MUTANT PAIR USING YEAST MATING AND CH3 MUTANT PAIR PRODUCED THEREBY

(71) Applicant: AJOU UNIVERSITY INDUSTRY-ACADEMIC COOPERATION FOUNDATION, Suwon-si (KR)

(72) Inventors: Yong Sung Kim, Suwon-si (KR); Hye Ji Choi, Gumi-si (KR); Ji Hee Ha, Suwon-si (KR)

(73) Assignee: AJOU UNIVERSITY INDUSTRY—ACADEMIC COOPERATION FOUNDATION, Suwon-si (KR)

( * ) Notice: Subject to any disclaimer, the term of this patent is extended or adjusted under 35 U.S.C. 154(b) by 762 days.

(21) Appl. No.: 15/778,966

(22) PCT Filed: Oct. 12, 2016

(86) PCT No.: PCT/KR2016/011396
§ 371 (c)(1),
(2) Date: May 24, 2018

(87) PCT Pub. No.: WO2017/065484
PCT Pub. Date: Apr. 20, 2017

(65) Prior Publication Data
US 2018/0346600 A1    Dec. 6, 2018

(30) Foreign Application Priority Data

Oct. 12, 2015    (KR) .................. 10-2015-0142181

(51) Int. Cl.
*C07K 16/46*    (2006.01)
*C12N 15/81*    (2006.01)
(Continued)

(52) U.S. Cl.
CPC ............ *C07K 16/46* (2013.01); *C07K 16/468* (2013.01); *C12N 15/1037* (2013.01);
(Continued)

(58) Field of Classification Search
CPC .............. A61K 2039/505; C07K 16/46; C07K 16/468; C07K 2317/10; C07K 2317/31;
(Continued)

(56) References Cited

U.S. PATENT DOCUMENTS 5,807,706 A    9/1998  Carter et al.
2010/0009866 A1    1/2010  Prinz et al.
(Continued)

FOREIGN PATENT DOCUMENTS

EP    2927321 A1    10/2015
JP    H11-500915 A    1/1999
(Continued)

OTHER PUBLICATIONS

K. Gunasekaran et al., "Enhancing antibody Fc heterodimer formation through electrostatic steering effects : applications to bispecific molecules and monovalent IgG", JBC Papers in Press, Apr. 16, 2010, pp. 1-20 (20 pages total).
(Continued)

*Primary Examiner* — Jeremy C Flinders
(74) *Attorney, Agent, or Firm* — Sughrue Mion, PLLC

(57) ABSTRACT

A method for evaluating and screening a mutant inducing the high-efficiency formation of heterodimers from a human antibody heavy chain constant region mutant pair combination library in order to increase the yield of formation of human antibody heterodimeric heavy chain constant regions. A heterodimeric heavy chain constant region (heterodimeric F) library is obtained by the method. A CH3 domain mutant pair, in which the formation of the heterodimeric heavy chain constant regions is preferred in the
(Continued)

library, forms heterodimeric heavy chain constant regions at a high yield of at least 80-90%, and also has excellent thermal stability and retains binding ability to the heavy chain constant region receptor (FcRn).

29 Claims, 36 Drawing Sheets

Specification includes a Sequence Listing.

(51) Int. Cl.
  *C12N 15/10* (2006.01)
  *C40B 40/02* (2006.01)
  *A61K 39/00* (2006.01)
  *C40B 20/04* (2006.01)

(52) U.S. Cl.
  CPC ........ *C12N 15/81* (2013.01); *A61K 2039/505* (2013.01); *C07K 2317/10* (2013.01); *C07K 2317/31* (2013.01); *C07K 2317/35* (2013.01); *C07K 2317/526* (2013.01); *C07K 2317/64* (2013.01); *C07K 2319/30* (2013.01); *C40B 20/04* (2013.01); *C40B 40/02* (2013.01)

(58) Field of Classification Search
  CPC .......... C07K 2317/35; C07K 2317/526; C07K 2317/64; C07K 2319/30; C12N 15/1037; C12N 15/81; C40B 40/02; C40B 20/04
  See application file for complete search history.

(56) References Cited

U.S. PATENT DOCUMENTS

| | | | |
|---|---|---|---|
| 2010/0256339 | A1 | 10/2010 | Bossenmaier et al. |
| 2010/0286374 | A1 | 11/2010 | Kannan et al. |
| 2011/0054151 | A1 | 3/2011 | Lazr et al. |
| 2012/0149876 | A1 | 6/2012 | Von Kreudenstein et al. |
| 2014/0072579 | A1 | 3/2014 | De Kruif et al. |

FOREIGN PATENT DOCUMENTS

| | | | |
|---|---|---|---|
| JP | 2011-508604 | A | 3/2011 |
| JP | 2012-522524 | A | 9/2012 |
| KR | 10-2013-0103325 | A | 9/2013 |
| KR | 10-2013-0135866 | A | 12/2013 |
| KR | 10-2014-0067944 | A | 6/2014 |
| WO | 96/27011 | A1 | 9/1996 |
| WO | 2009080004 | A1 | 7/2009 |
| WO | 2011143545 | A1 | 11/2011 |
| WO | 2012025530 | A1 | 3/2012 |
| WO | 2012032080 | A1 | 3/2012 |
| WO | 2015/150447 | A1 | 10/2015 |

OTHER PUBLICATIONS

Communication dated May 23, 2019, from the European Patent Office in application No. 16855701.5.
Du-San Baek, et al., "Construction of a Large Synthetic Human Fab Antibody Library on Yeast Cell Surface by Optimized Yeast Mating", Journal of Microbiology and Biotechnology, 2014, pp. 408-420, vol. 24, No. 3.
Hye-Ji Choi, et al., "Engineering of Immunoglobulin Fc Heterodimers Using Yeast Surface-Displayed Combinatorial Fc Library Screening", PloS One, Dec. 2015, pp. 1/20-20/20, vol. 10, No. e0145349.
Ji-Hee Ha, et al., "Immunoglobulin Fc Heterodimer Platform Technology: From Design to Applications in Therapeutic Antibodies and Proteins", Frontiers in Immunology, Oct. 6, 2016, pp. 1-16, article No. 394.
International Search Report for PCT/KR2016/011396 dated Jan. 10, 2017 [PCT/ISA/210].
Written Opinion for PCT/KR2016/011396 dated Jan. 10, 2017 [PCT/ISA/237].
Notification of Reason for Refusal for Korean Application No. 10-2015-0142181 dated Jun. 27, 2017.
Notice of Final Rejection for Korean Application No. 10-2015-0142181 dated Jan. 25, 2018.
Japanese Patent Office; Communication dated Oct. 31, 2017 in Application No. 2015-543998.
Korean Intellectual Property Office, Communication dated Mar. 11, 2014 in application No. PCT/KR2013/010861.
Xie, Zhigang et al., "A new format of bispecific antibody: highly efficient heterodimerization, expression and tumor cell lysis", Journal of Immunological Methods, vol. 296, No. 1, 2005, pp. 95-101, XP027659093.
Korean Intellectual Property Office, Communication dated Mar. 24, 2015 issued in Korean application No. 10-2013-0145564.
Merchant AM et al., "An efficient route to human bispecific IgG", Nature Biotechnology 16, 677-681 (1998) doi:10.1038/nbt0798-677, 1 page.
Klein et al, MABS, "Progress in overcoming the chain association issue in bispecific heterodimeric IgG antibodies," vol. 4 No. 6, Nov. 1, 2012, 11 pages in total.
European Patent Office, Communication dated May 12, 2016 issued in European application No. 13859121.9.
Examination Report dated Nov. 20, 2019 from the Intellectual Property Office of India in Application No. 5014/DELNP/2015.
Atwell et al., "Stable Heterodimers from Remodeling the Domain Interface of a Homodimer using a Phage Display Library", J. Mol. Biol. (1997) 270, pp. 26-35.
Chan et al., "Therapeutic antibodies for autoimmunity and inflammation", Nature Reviews (2010) 10, pp. 301-316.
Choi et al., "A Heterodimeric Fc-Based Bispecific Antibody Simultaneously Targeting VEGFR-2 and Met Exhibits Potent Antitumor Activity", Mol. Cancer. Ther.(2013), pp. 2748-2759.
Choi et al., "Crystal structures of immunoglobulin Fc heterodimers reveal the molecular basis for heterodimer formation", Molecular Immunology (2015) 65 , pp. 377-383.
Cunningham et al., "Subgroups of Amino Acid Sequences in the Variable Regions of Immunoglobulin Heavy Chains", Proc. Natl. Acad. Sci. U S A (1969) 64(3), pp. 997-1003.
Davis et al., "SEEDbodies: Fusion Proteins Based on Strand-Exchange Engineered Domain (SEED) CH3 Heterodimers in an Fc Analogue Platform for Asymmetric Binders or Immunofusions and Bispecific Antibodies", Protein Eng. Des. Sel. (2010) 23(4), pp. 195-202.
Feng et al., "Design, Expression and Characterization of a Soluble Single-Chain Functional Human Neonatal Fc Receptor", Protein Expression and Purification (2011) 79(1), pp. 66-71.
Gunasekaran et al., "Enhancing Antibody Fc Heterodimer Formation Through Electrostatic Steering Effects: Applications to Bispecific Molecules and Monovalent IgG", J. Biol. Chem. (2010) 285(25), pp. 19637-19646.
Holliger et al., "Engineered antibody fragments and the rise of single domains", Nat. Biotechnol. (2005) 23(9), pp. 1126-1136.
Kim et al., "Comparative Analyses of Complex Formation and Binding Sites Between Human Tumor Necrosis Factor-Alpha and Its Three Antagonists Elucidate Their Different Neutralizing Mechanisms", J Mol Biol (2007) 374, pp. 1374-1388.
Lu et al., "Simultaneous Blockade of Both the Epidermal Growth Factor Receptor and the Insulin-Like Growth Factor Receptor Signaling Pathways in Cancer Cells with a Fully Human Recombinant Bispecific Antibody", J Biol Chem (2004) 279(4), pp. 2856-2865.
Miller et al., "Design, Construction, and in Vitro Analyses of Multivalent Antibodies", J. Immunol. (2003) 170(9), pp. 4854-4861.
Milstein et al., "Hybrid Hybridomas and Their Use in Immunohistochemistry", Nature (1983) 305, pp. 537-540.
Moore et al., "A Novel Bispecific Antibody Format Enables Simultaneous Bivalent and Monovalent Co-Engagement of Distinct Target Antigens", MAbs (2011) 3(6), pp. 546-557.

(56) References Cited

OTHER PUBLICATIONS

Ridgway et al., "'Knobs-Into-Holes' Engineering of Antibody CH3 Domains for Heavy Chain Heterodimerization" Protein Eng. (1996) 9(7), pp. 617-621.
Strop et al., "Generating Bispecific Human Igg1 and Igg2 Antibodies from Any Antibody Pair" J Mol Biol (2012) 420, pp. 204-219.
Von Kreudenstein et al., "Protein Engineering and the Use of Molecular Modeling and Simulation: The Case of Heterodimeric Fc Engineering", Methods (2014) 65, pp. 77-94.
Von Kreudenstein et al., "Improving Biophysical Properties of a Bispecific Antibody Scaffold to Aid Developability: Quality by Molecular Design." mAb (2013) 5, pp. 646-654.

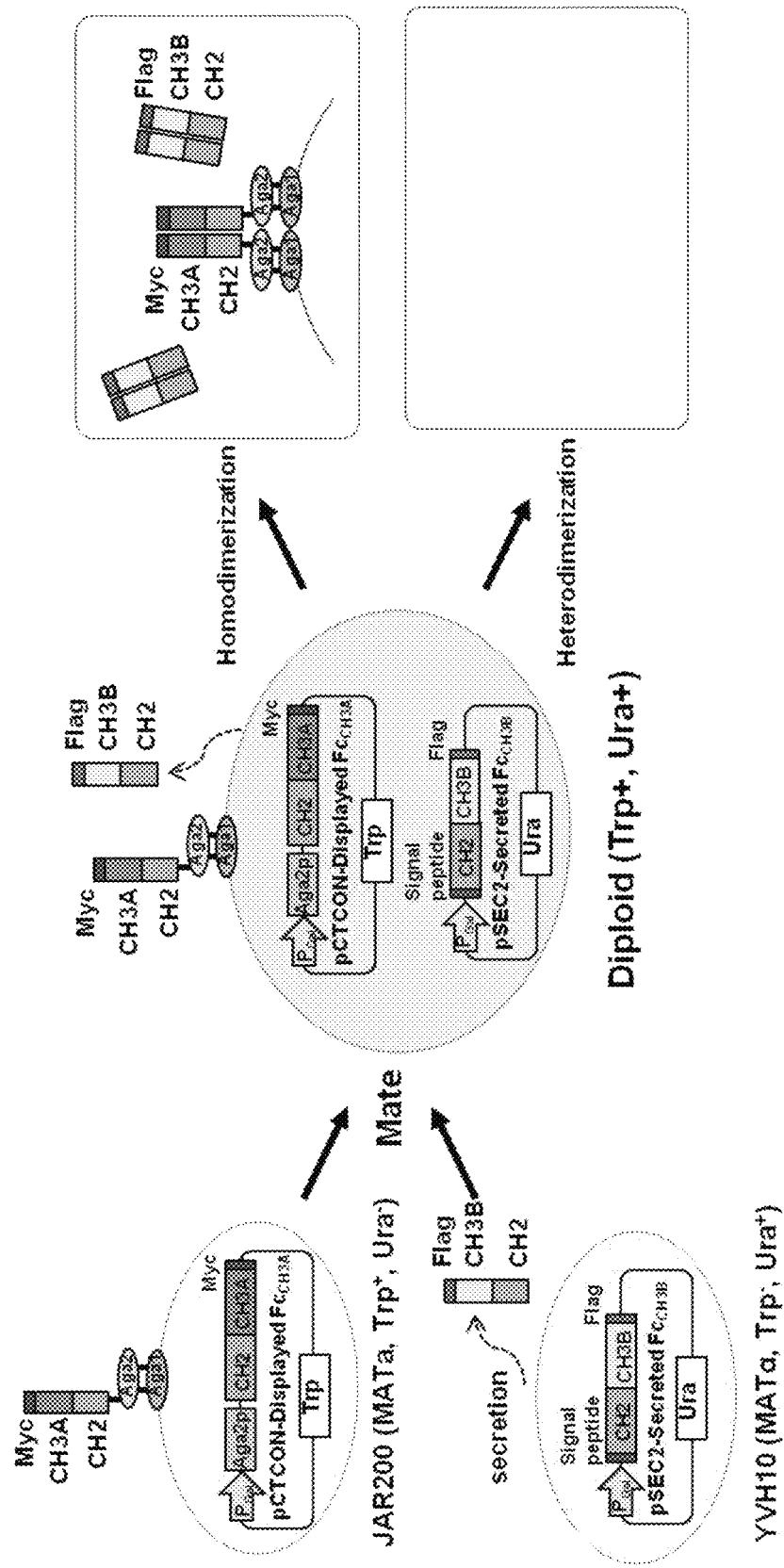
[Fig. 1]

[Fig. 2]
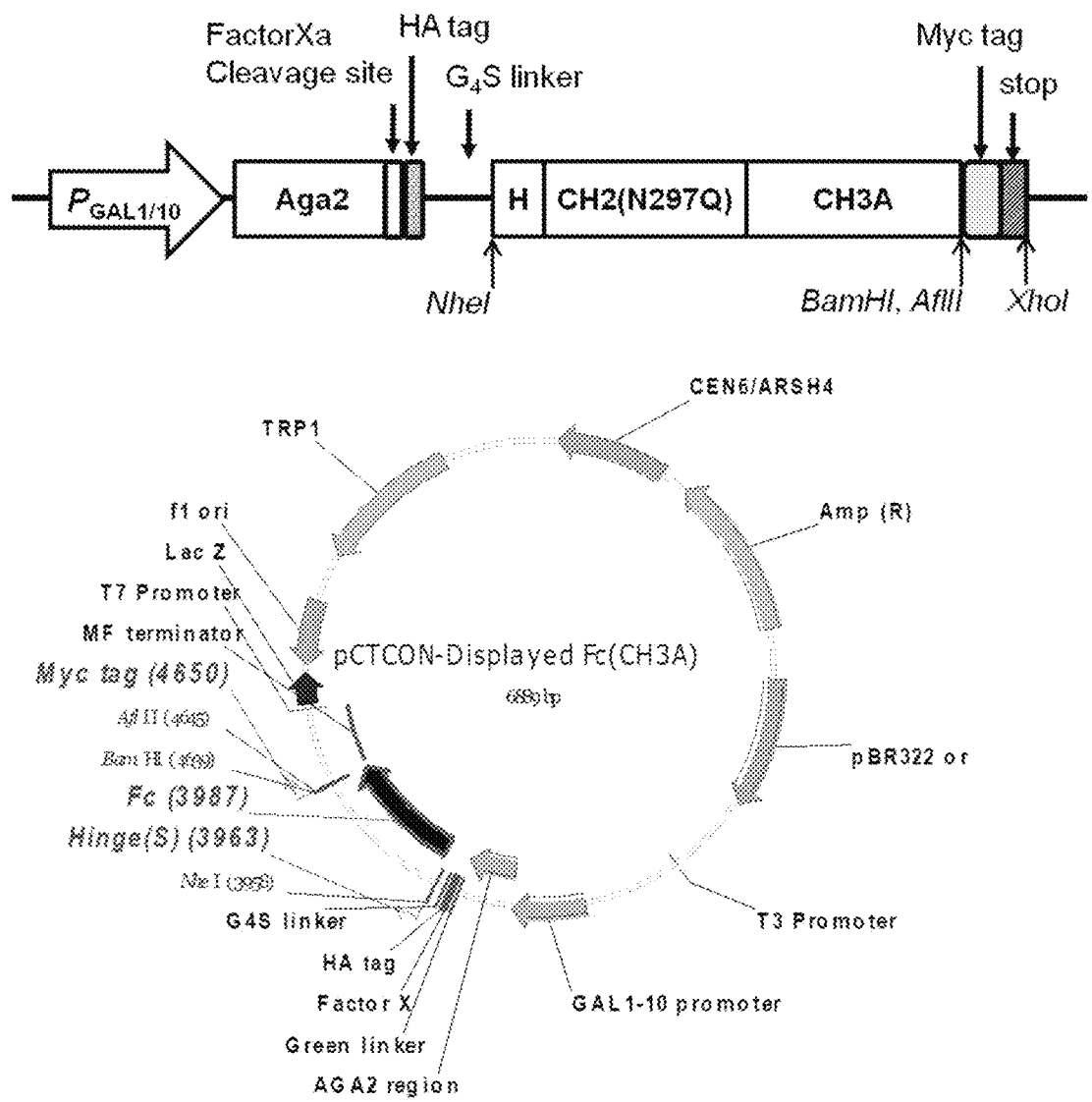

[Fig. 3]
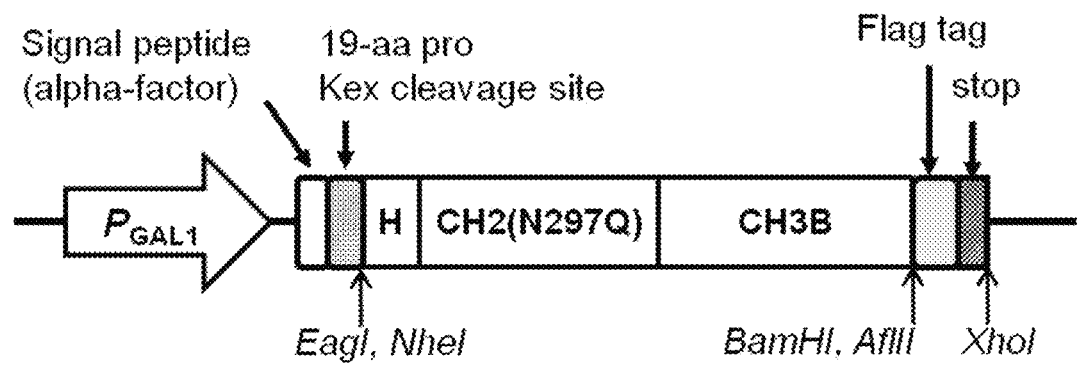
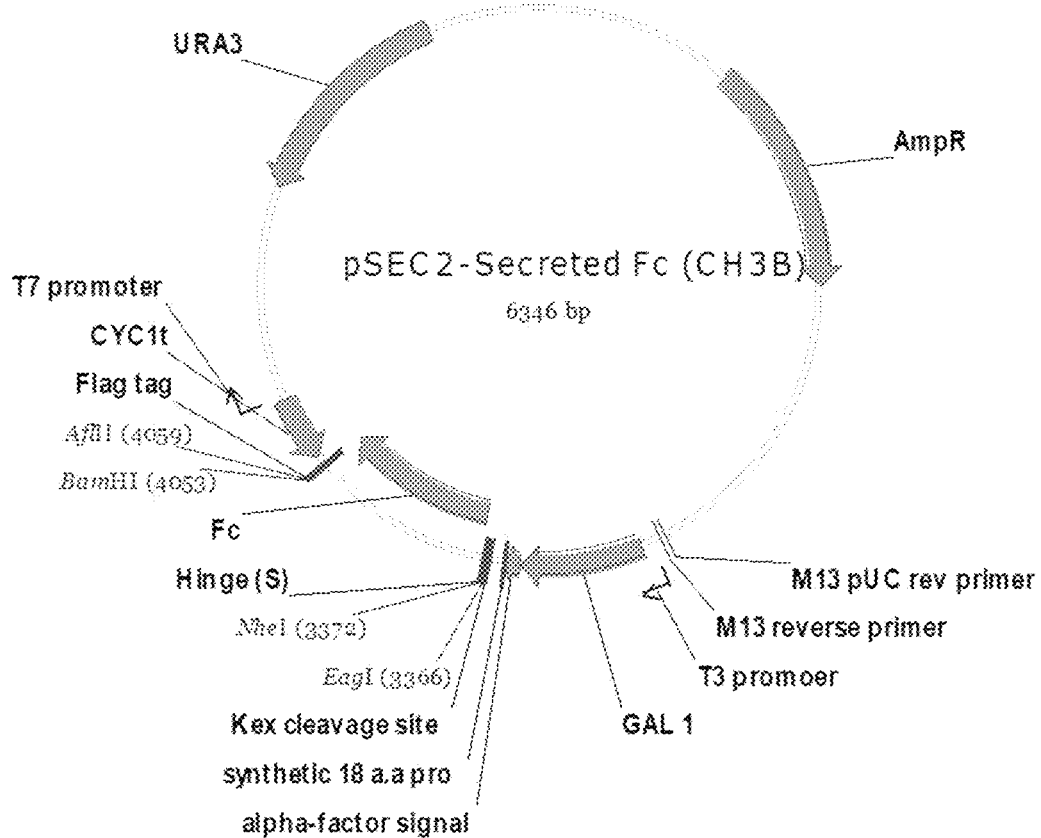

[Fig. 4A]
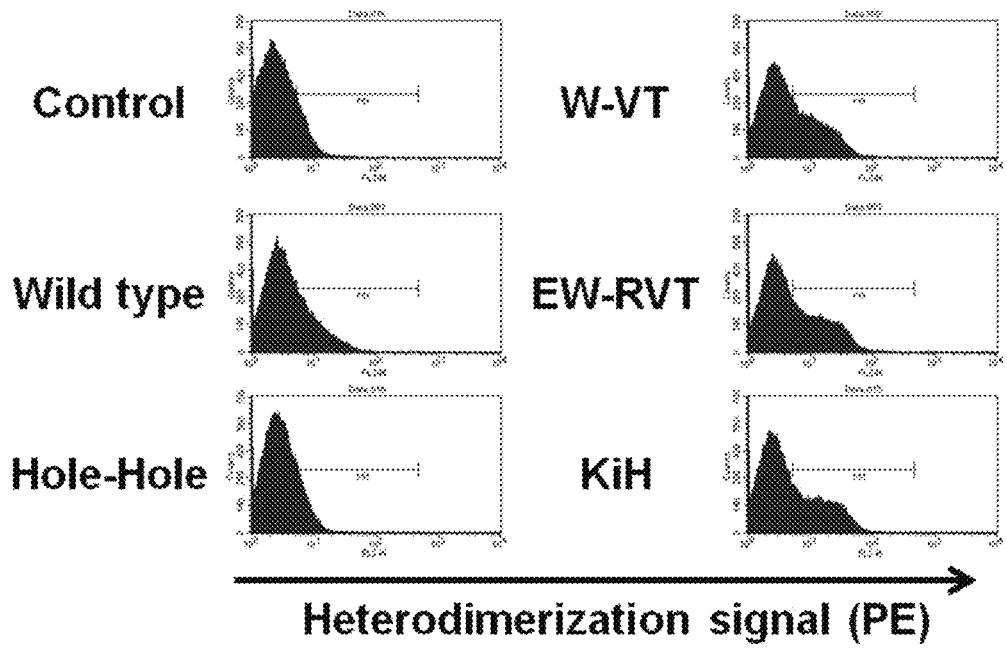
[Fig. 4B]
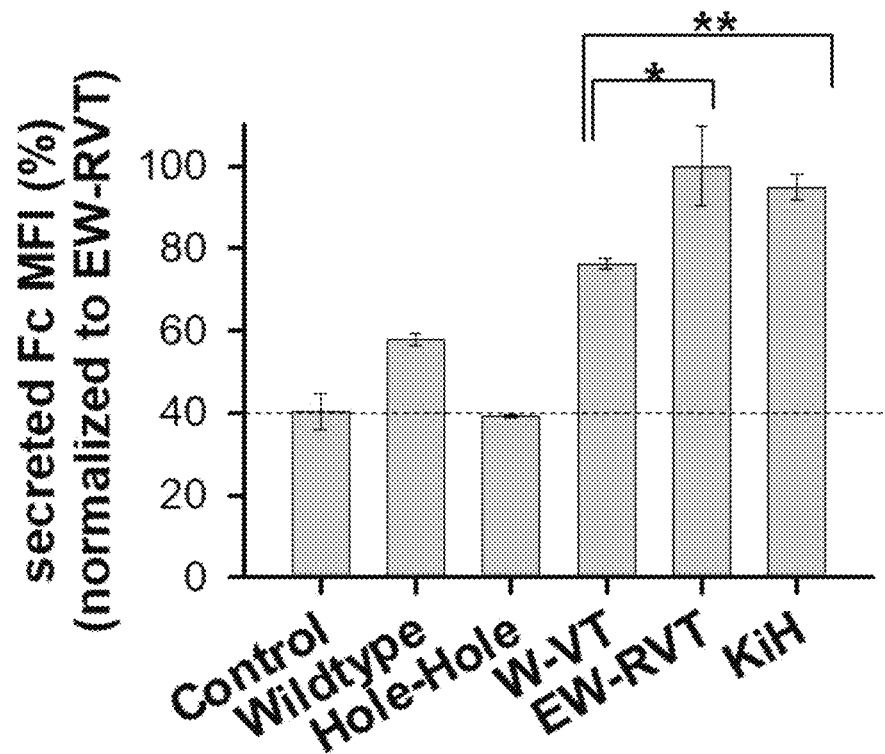

[Fig. 5]
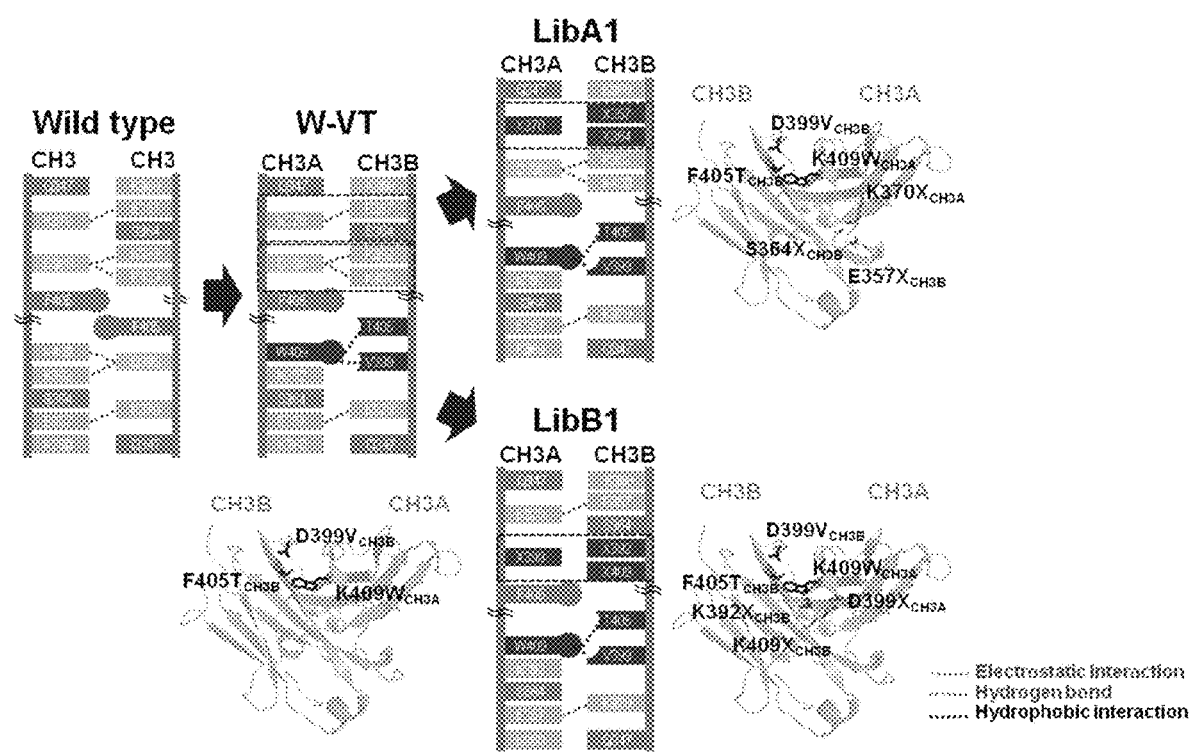

[Fig. 6A]
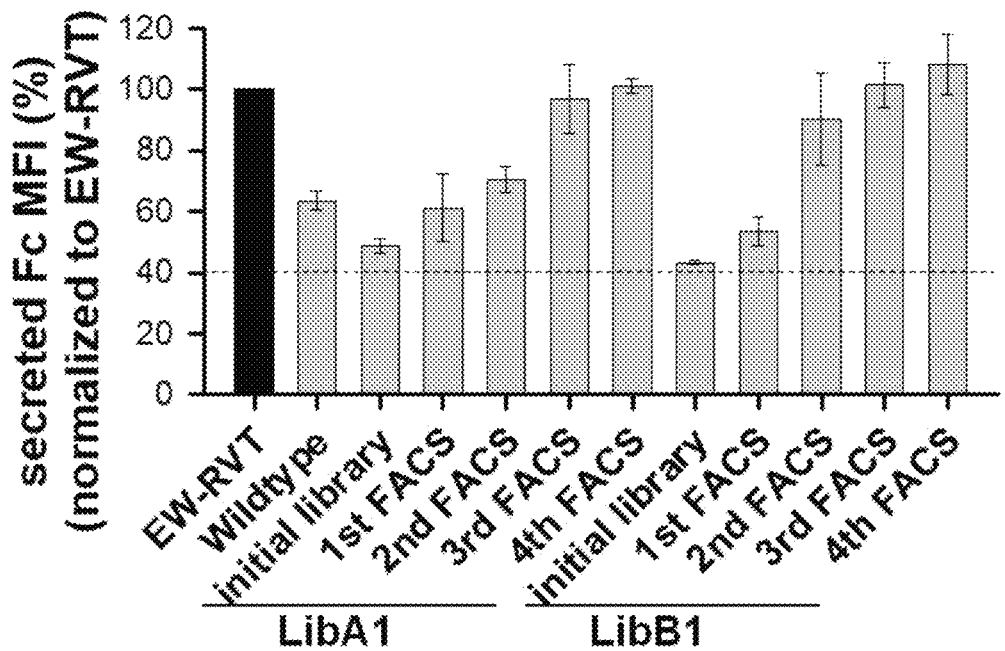
[Fig. 6B]
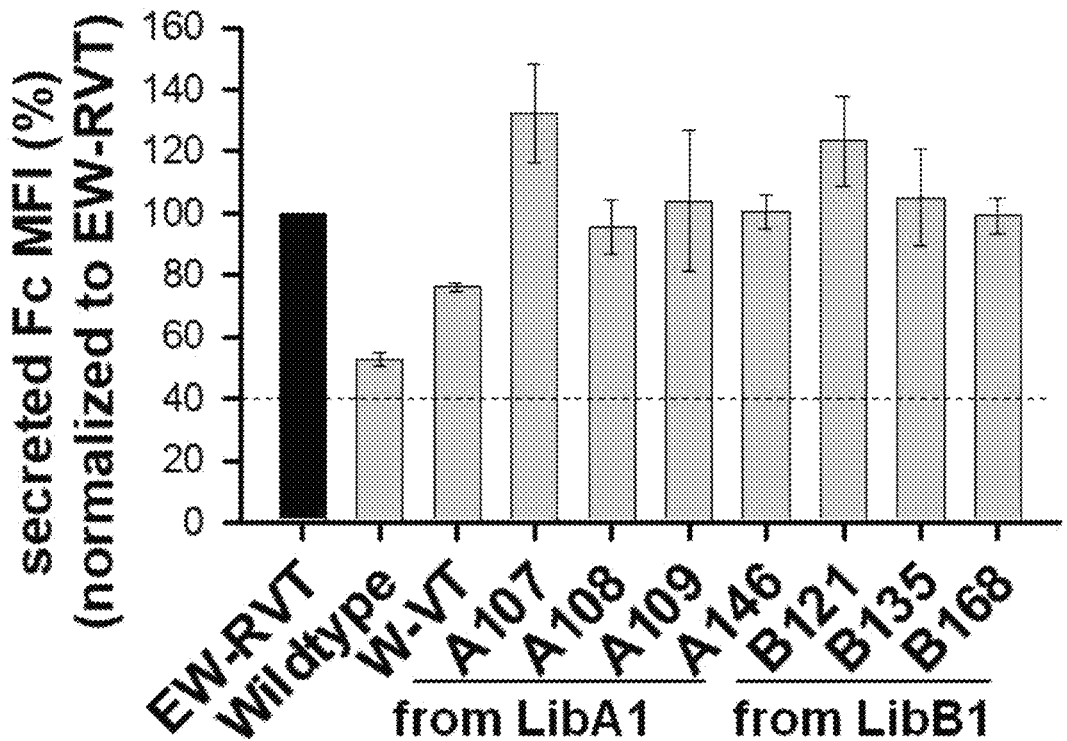

[Fig. 7]
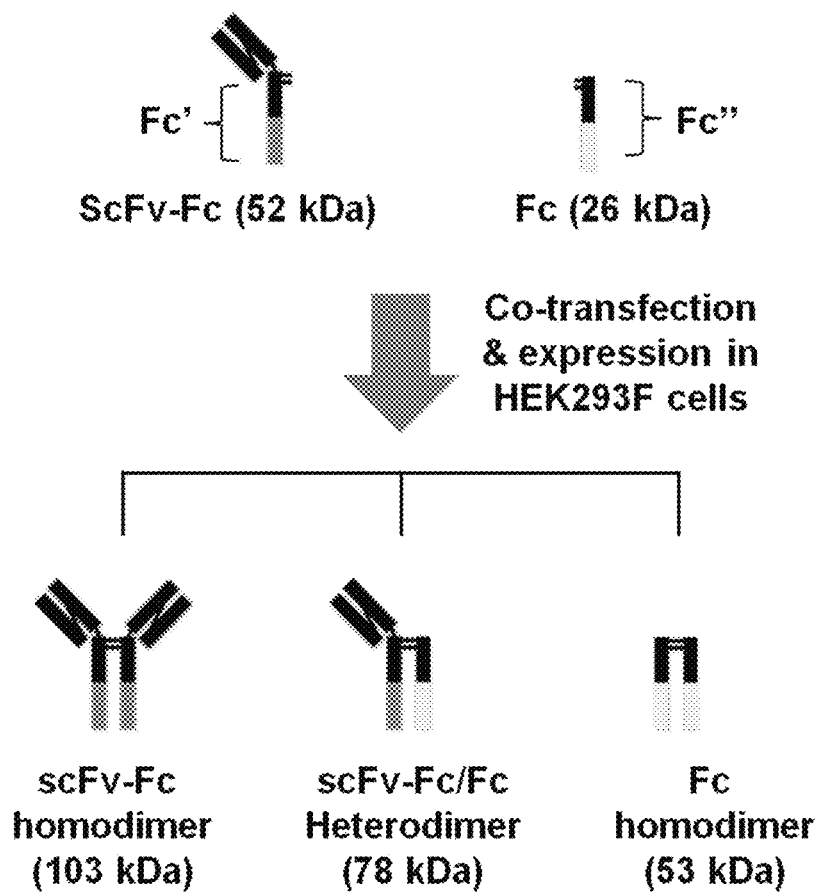

[Fig. 8]
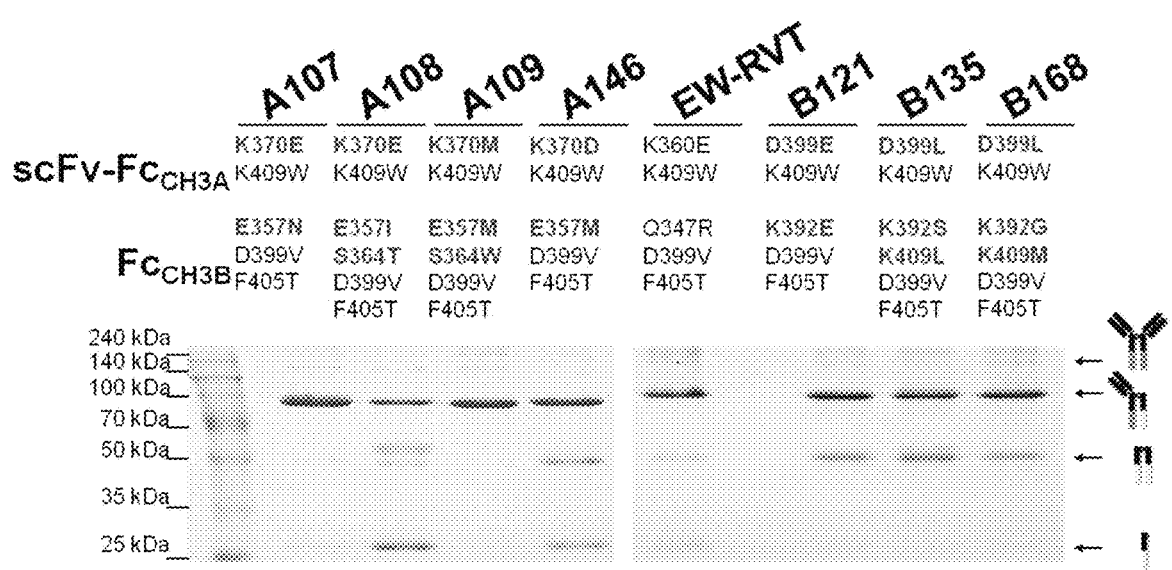

[Fig. 9]
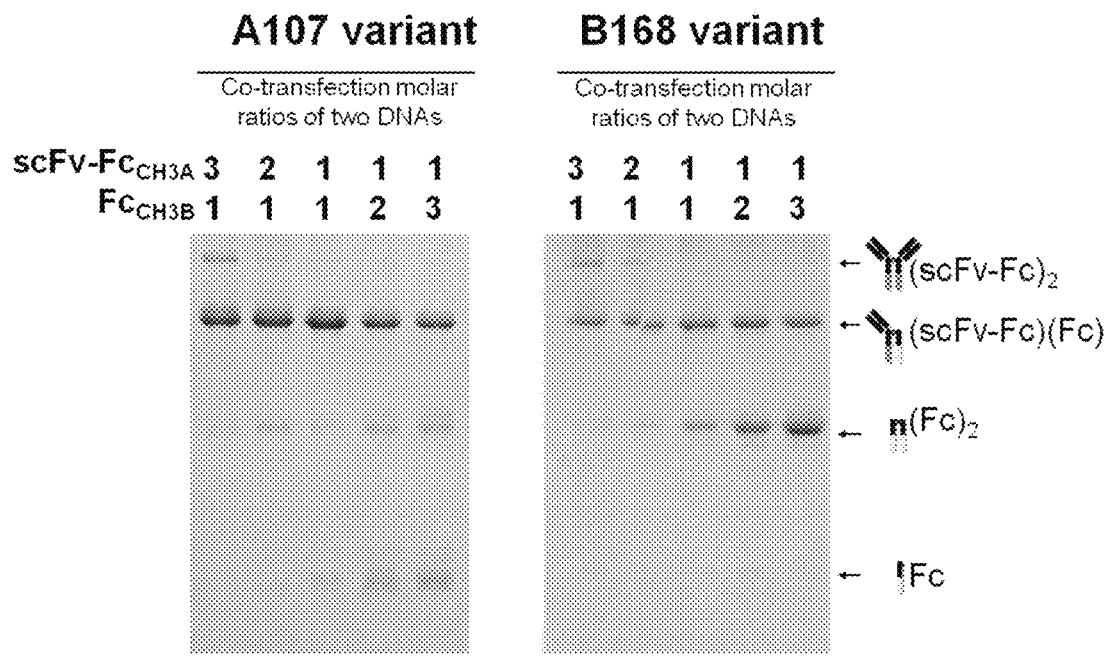
[Fig. 10]

[Fig. 11]
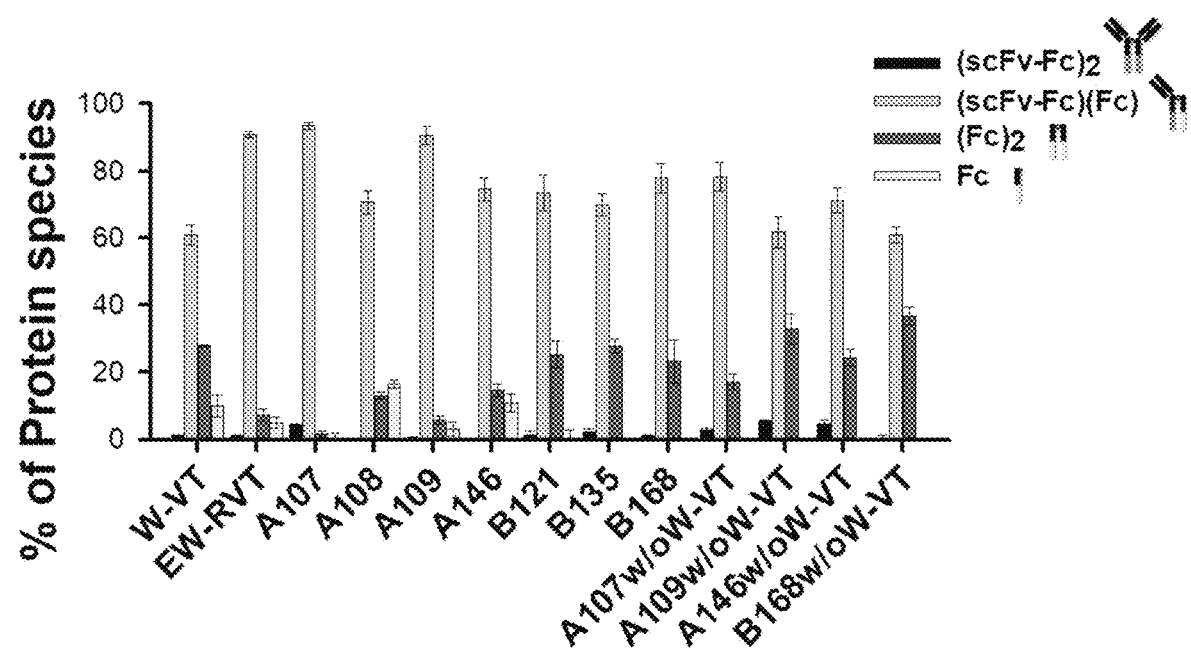

[Fig. 12A]
- ······ Distance
- ⟶ Unpaired charged residue
- ⟶ Steric clash
- ······ Hydrogen bond
- ---- π-π interaction
- ---- Electrostatic / cation-π interaction
- — — Disulfide bond
- ⟷ Electrostatic / anion-π repulsion
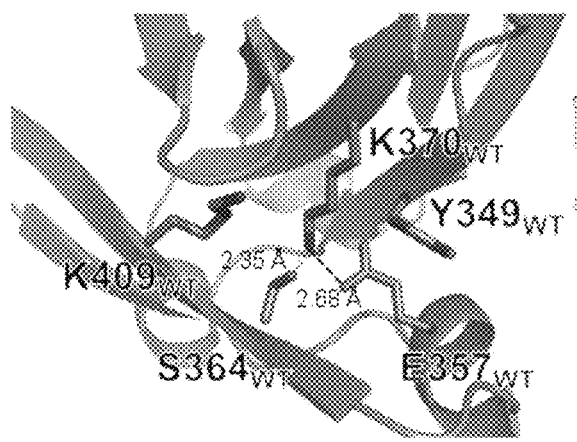
Wild type
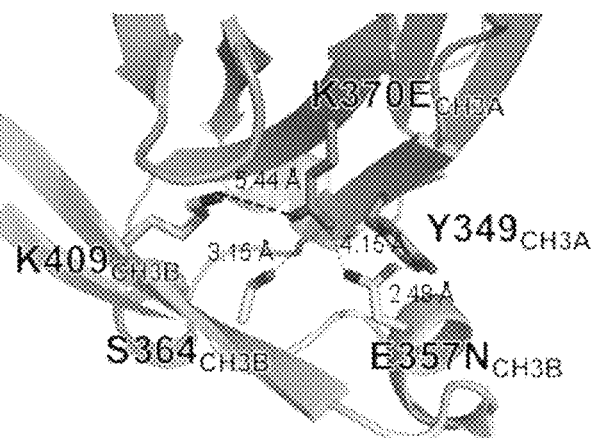
A107 heterodimer
(CH3A-CH3B)
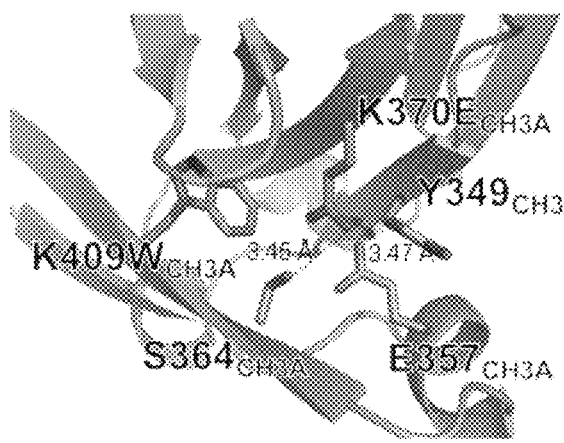
A107 homodimer
(CH3A-CH3A)
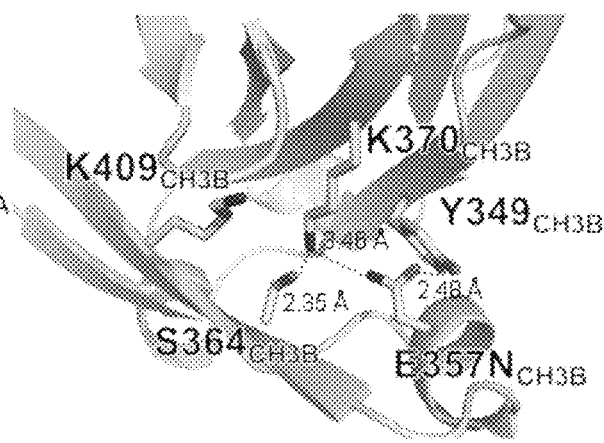
A107 homodimer
(CH3B-CH3B)

[Fig. 12B]
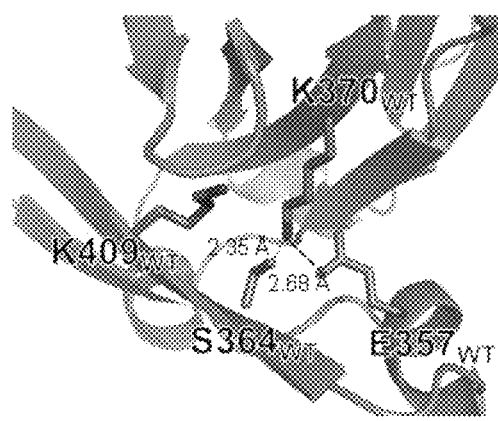
Wild type
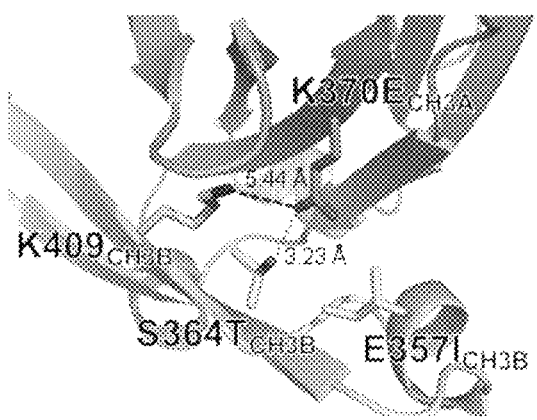
A108 heterodimer
(CH3A-CH3B)
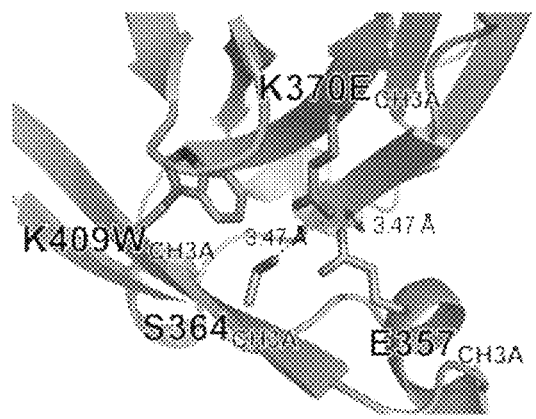
A108 homodimer
(CH3A-CH3A)
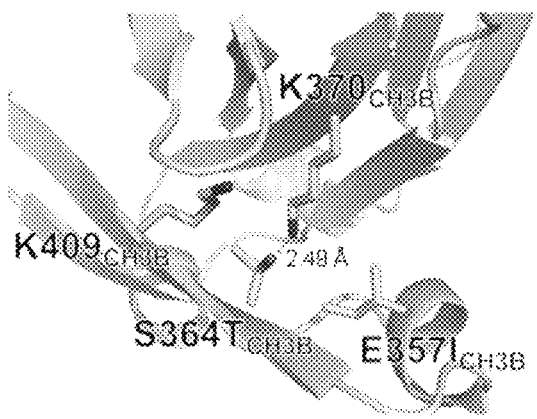
A108 homodimer
(CH3B-CH3B)

[Fig. 13A]
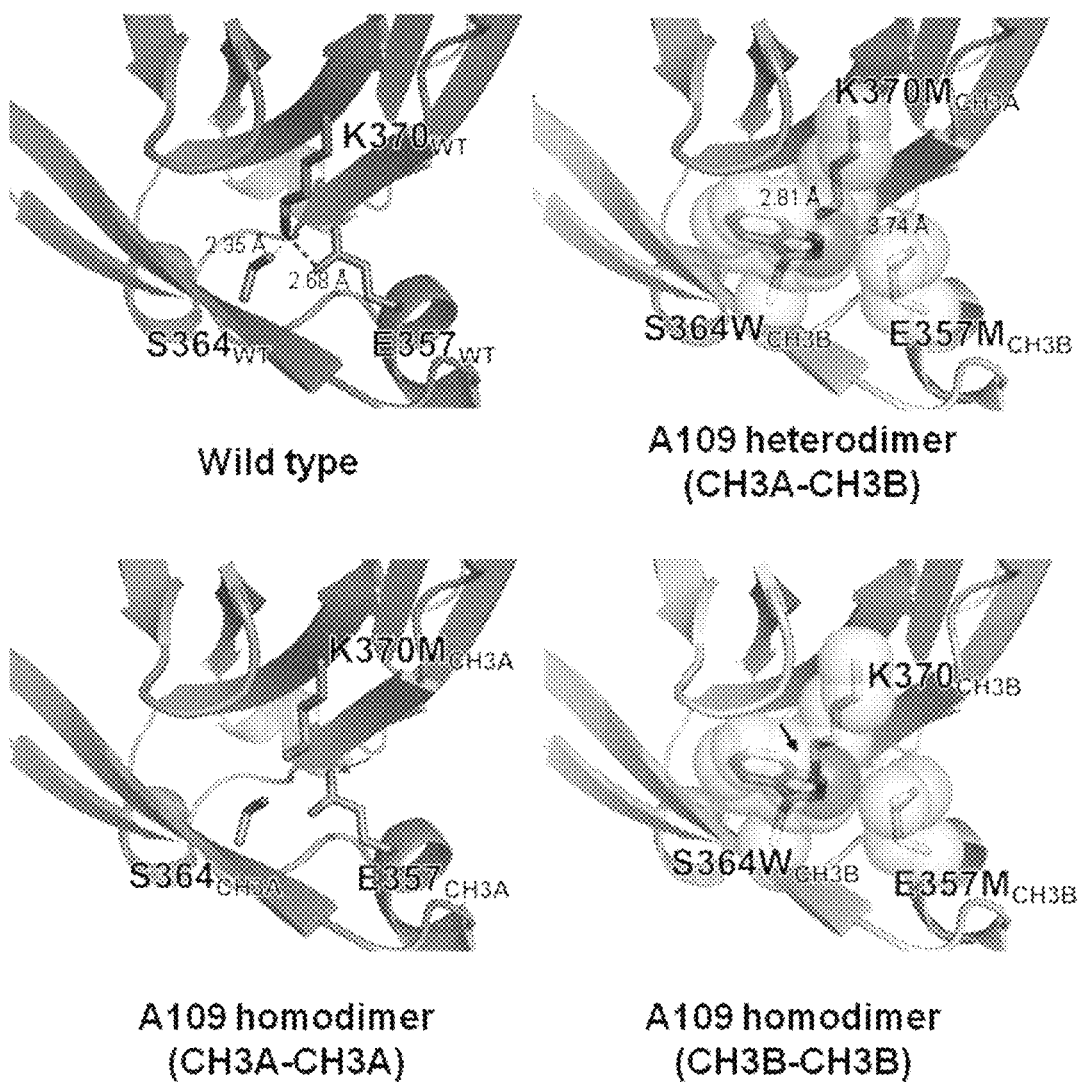

[Fig. 13B]
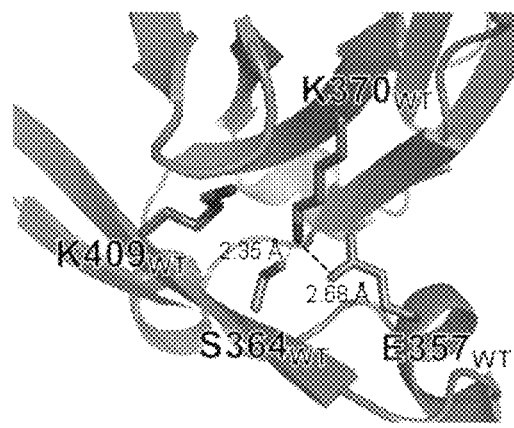
Wild type
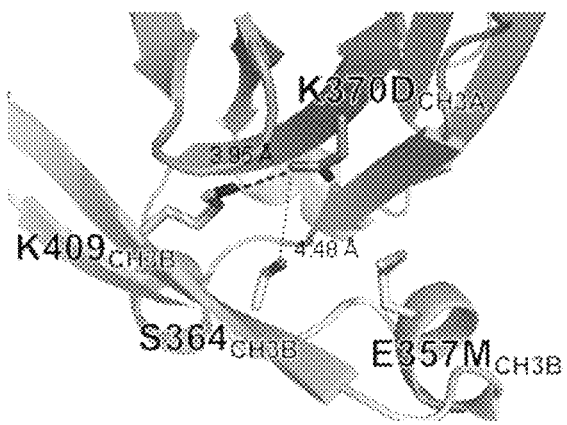
A146 heterodimer
(CH3A-CH3B)
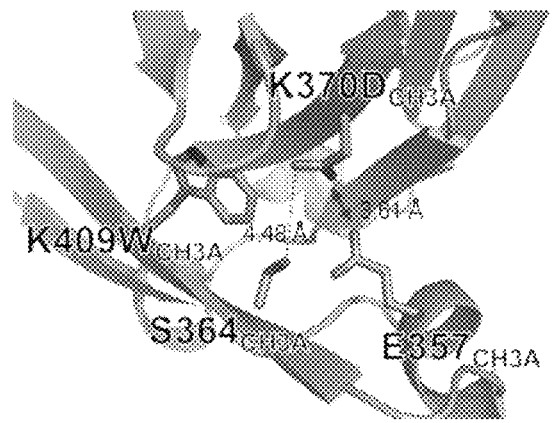
A146 homodimer
(CH3A-CH3A)
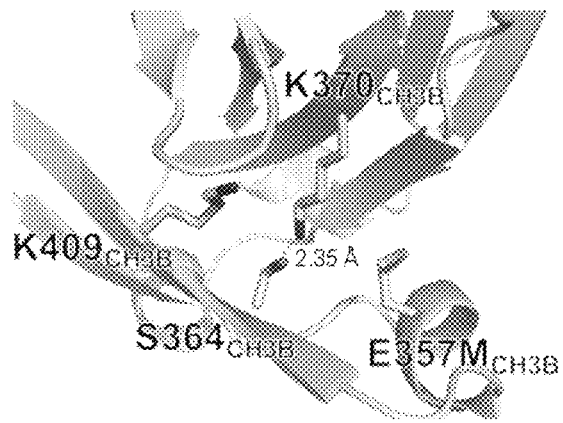
A146 homodimer
(CH3B-CH3B)

[Fig. 14A]
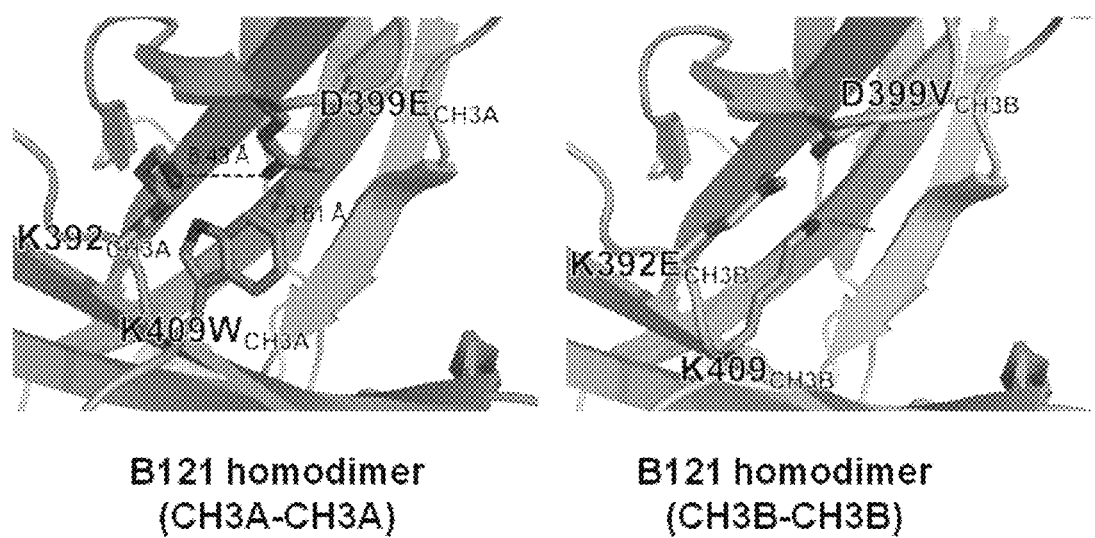

[Fig. 14B]
······· Distance
⟶ Unpaired charged residue
⟶ Steric clash
······· Hydrogen bond
---- π-π interaction
---- Electrostatic / cation-π interaction
— — Disulfide bond
⟷ Electrostatic / anion-π repulsion
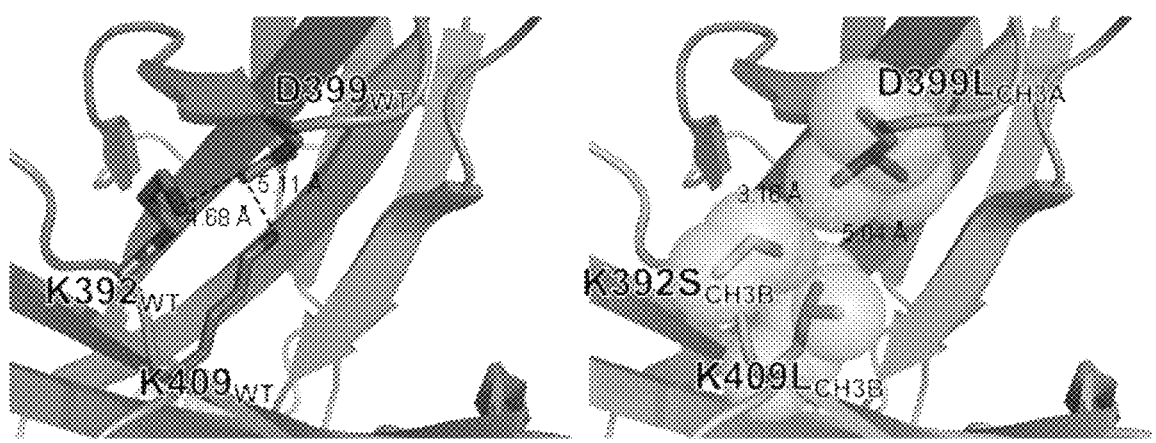
Wild type　　　　　　　B135 heterodimer
　　　　　　　　　　　　(CH3A-CH3B)
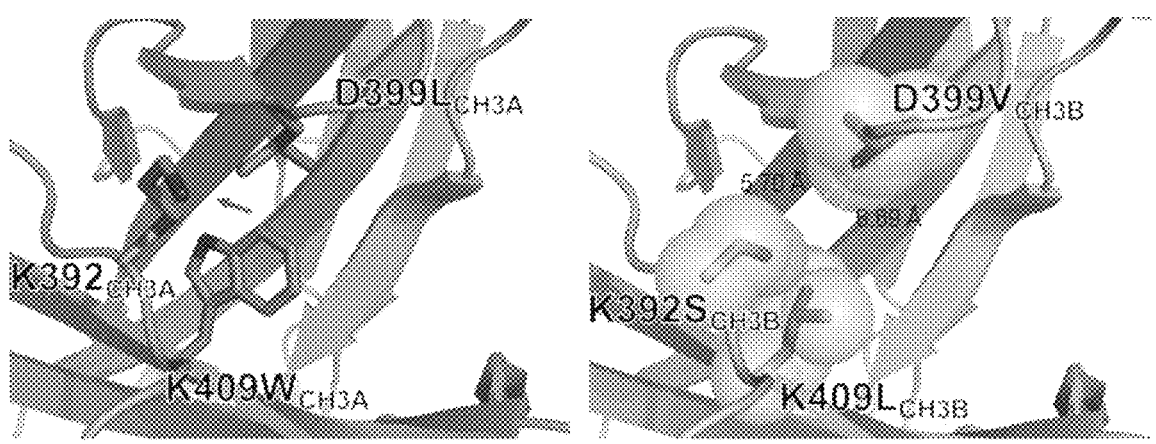
B135 homodimer　　　B135 homodimer
(CH3A-CH3A)　　　　(CH3B-CH3B)

[Fig. 15]
- Distance
- Unpaired charged residue
- Steric clash
- Hydrogen bond
- π-π interaction
- Electrostatic / cation-π interaction
- Disulfide bond
- Electrostatic / anion-π repulsion
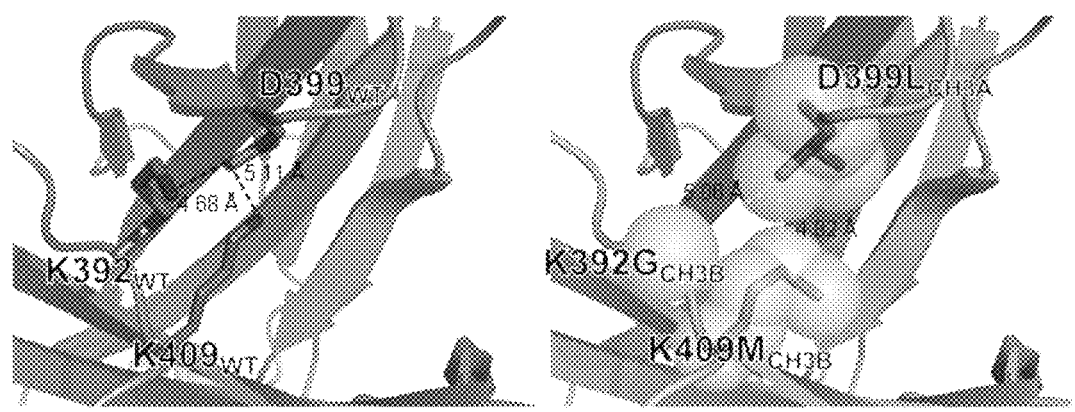
Wild type
B168 heterodimer
(CH3A-CH3B)
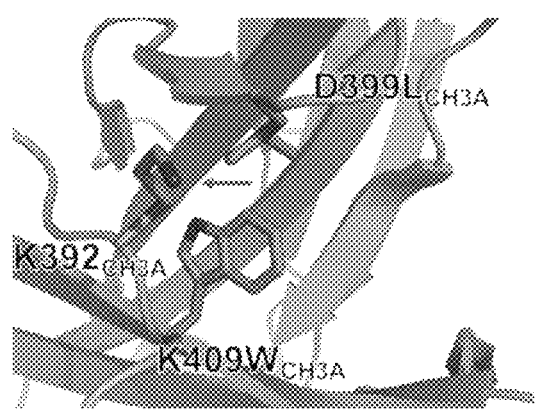 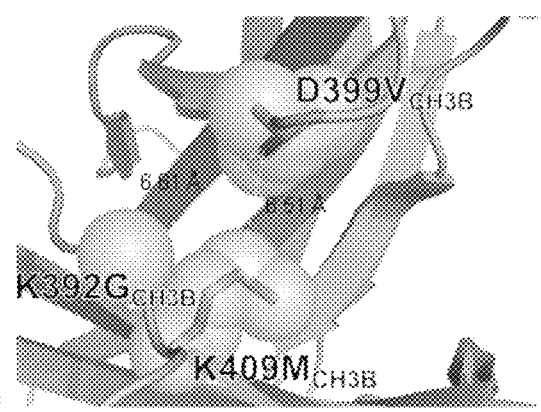
B168 homodimer
(CH3A-CH3A)
B168 homodimer
(CH3B-CH3B)

[Fig. 16]
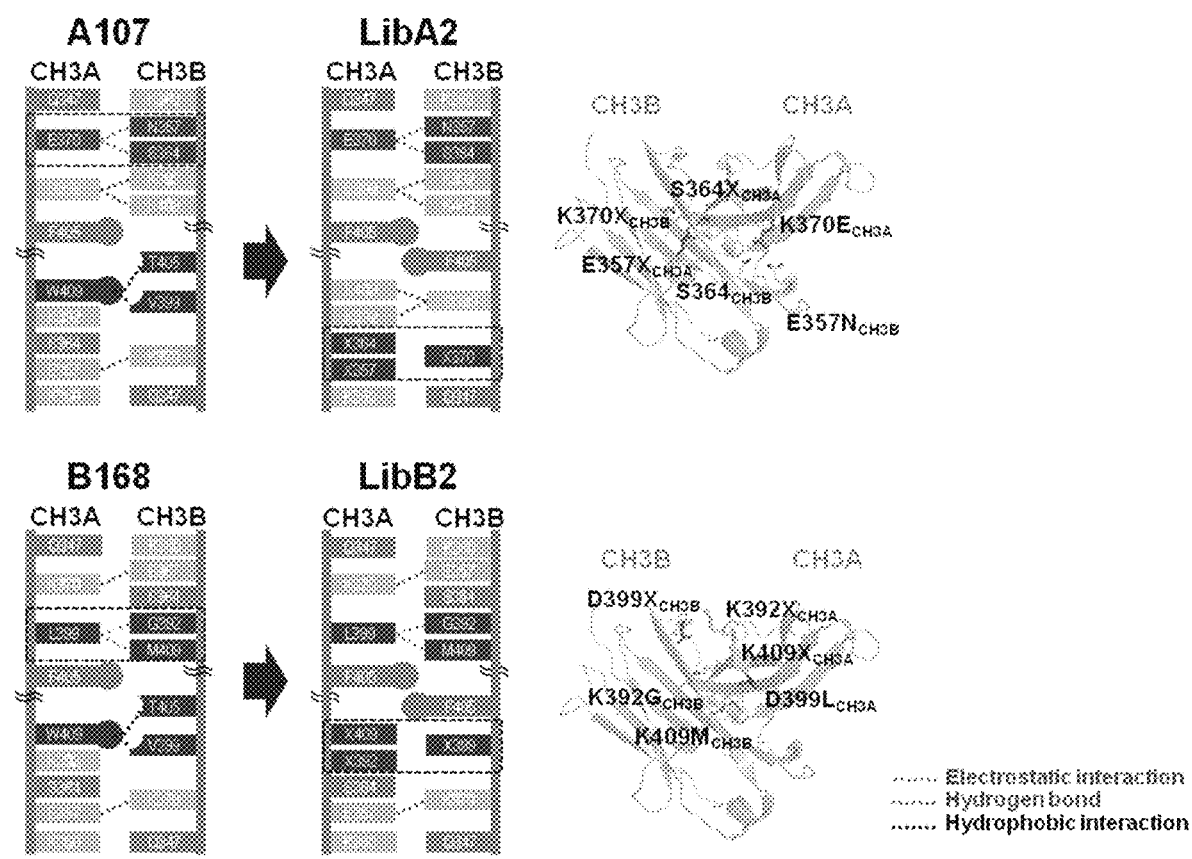

[Fig. 17A]
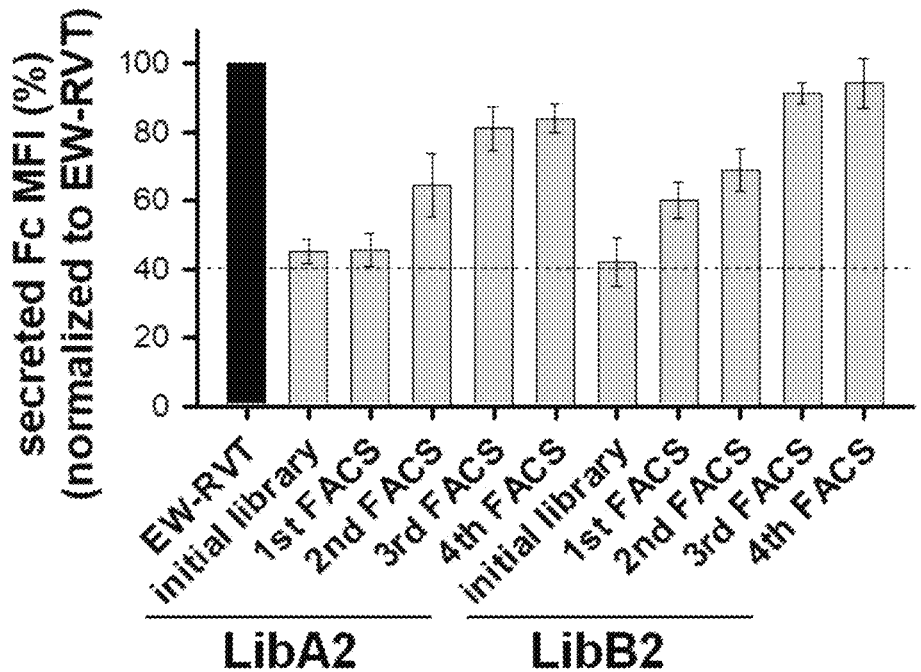
[Fig. 17B]
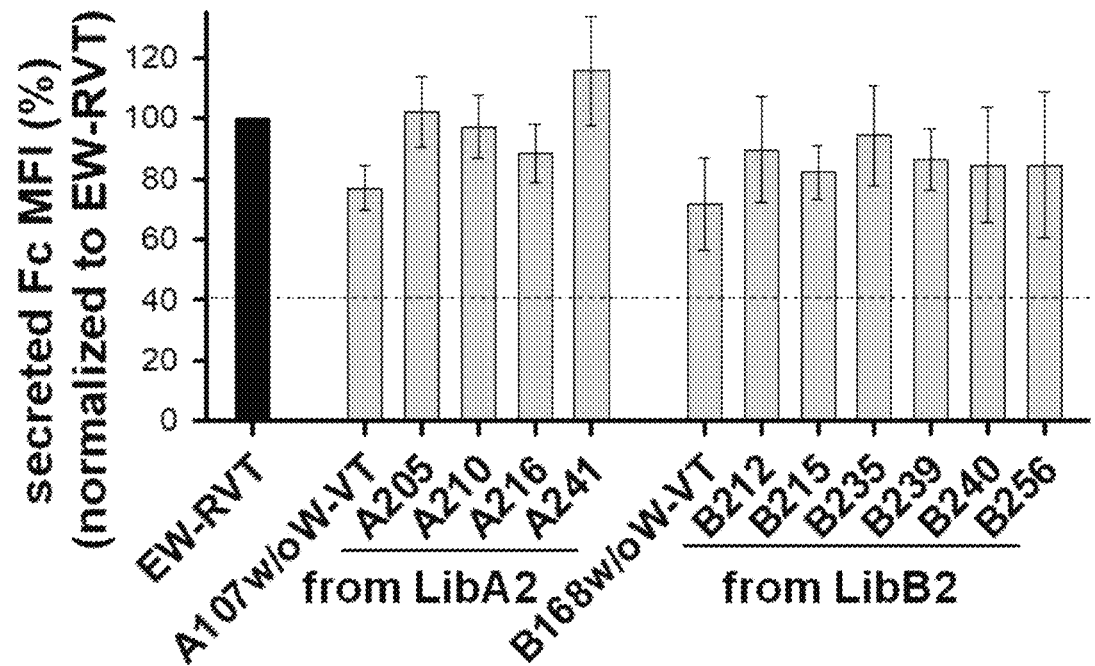

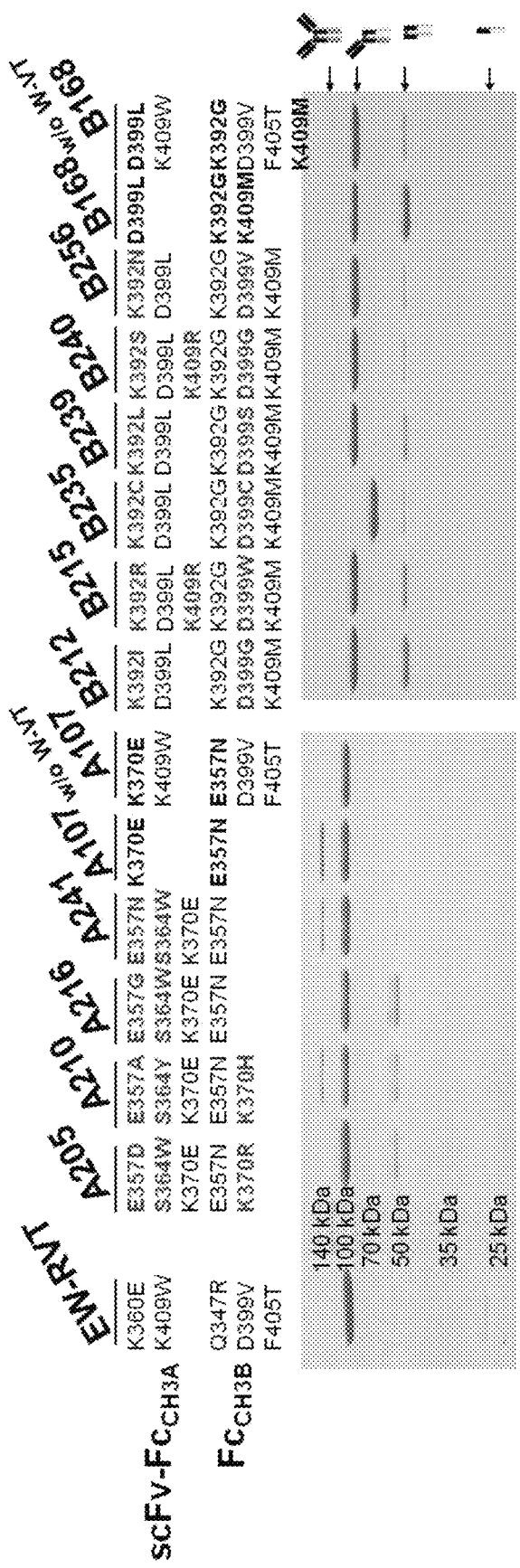
[Fig. 18A]

[Fig. 18B]
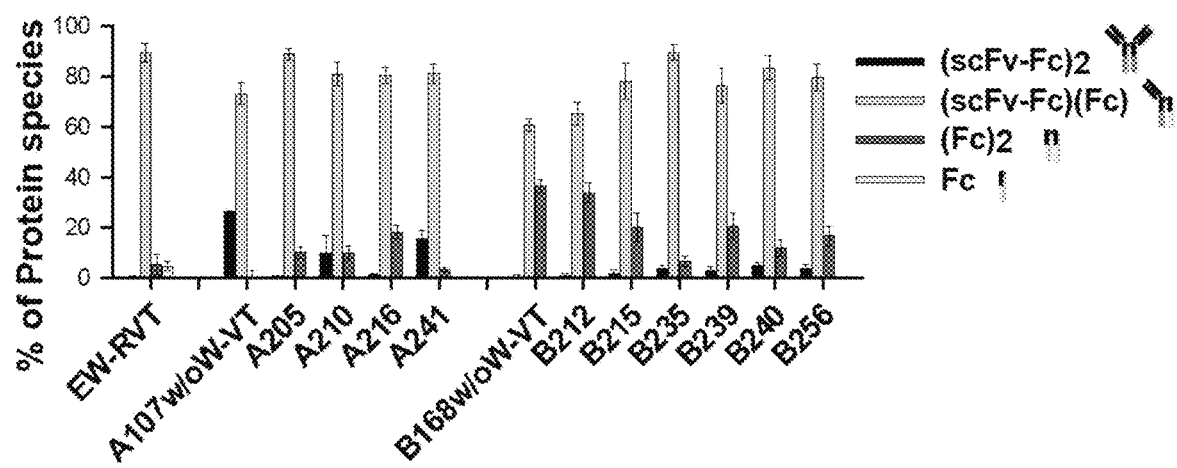

[Fig. 19]
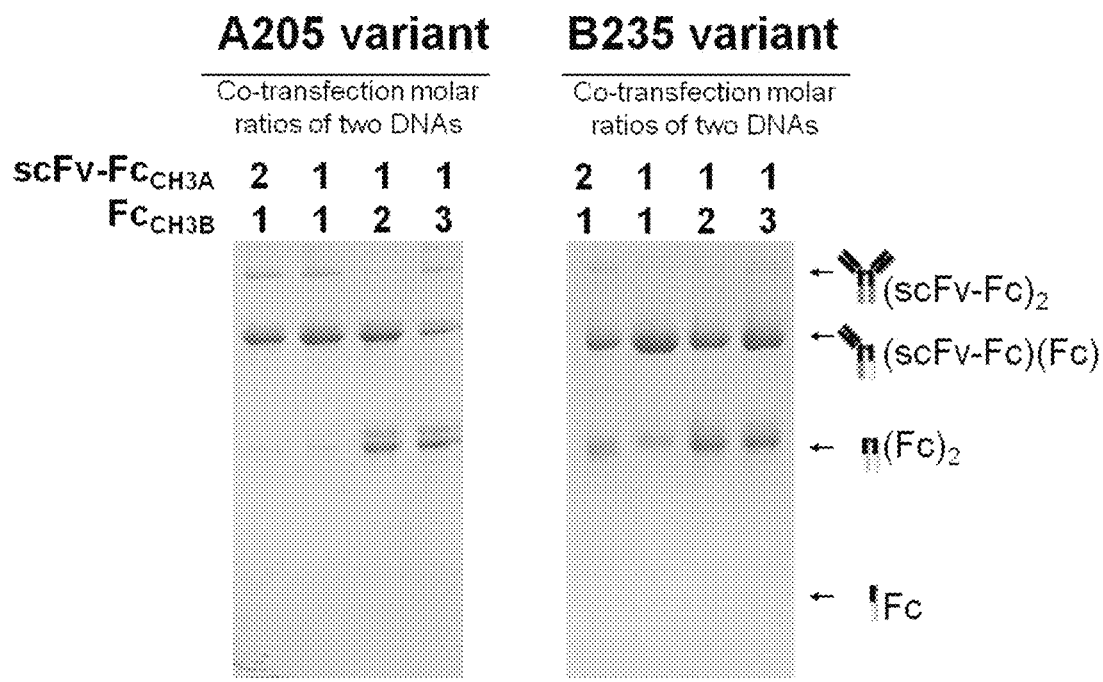

[Fig. 20A]
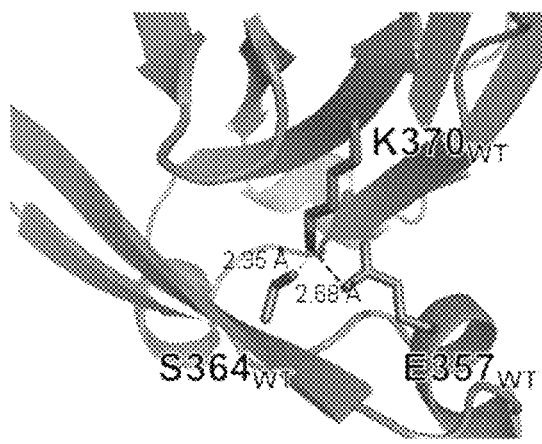
Wild type
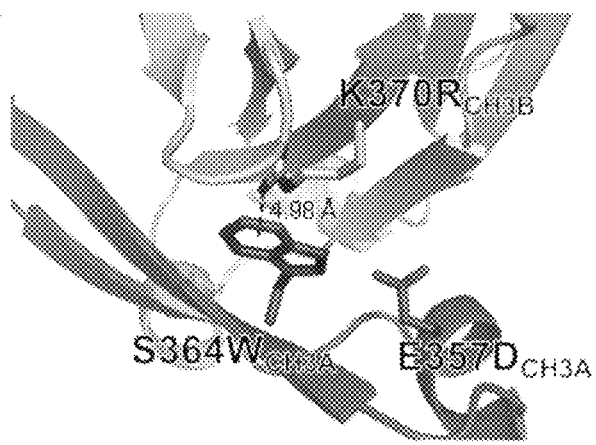
A205 heterodimer
(CH3A-CH3B)
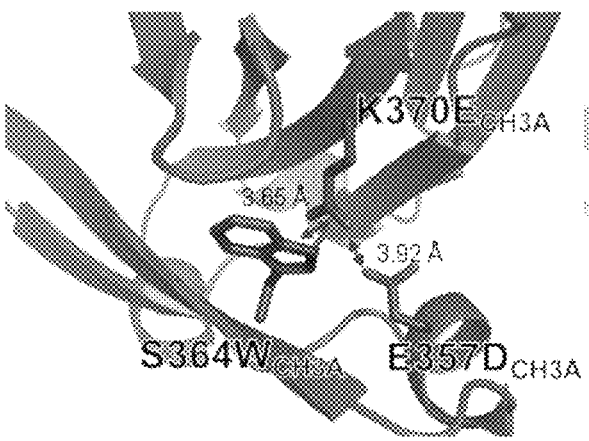
A205 homodimer
(CH3A-CH3A)
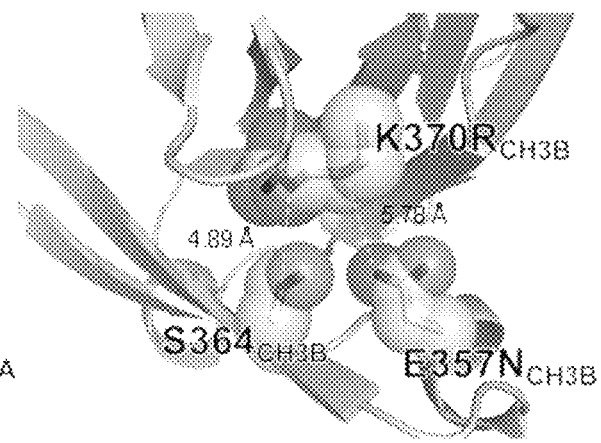
A205 homodimer
(CH3B-CH3B)

[Fig. 20B]
...... Distance
⎯→ Unpaired charged residue
⎯→ Steric clash
...... Hydrogen bond
━ ━ π-π interaction
-·-·- Electrostatic / cation-π interaction
— — Disulfide bond
⎯→ Electrostatic / anion-π repulsion
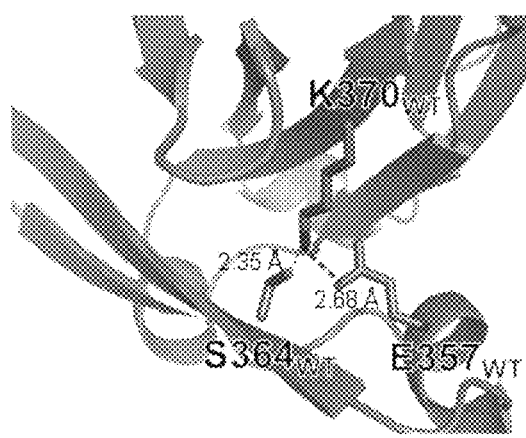
Wild type
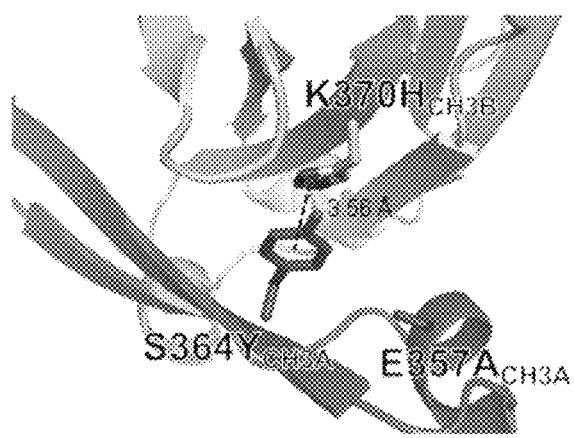
A210 heterodimer
(CH3A-CH3B)
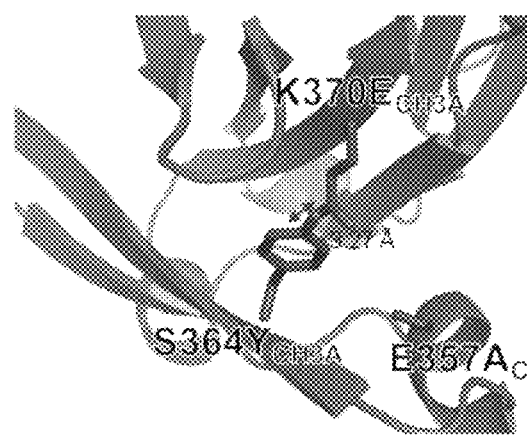
A210 homodimer
(CH3A-CH3A)
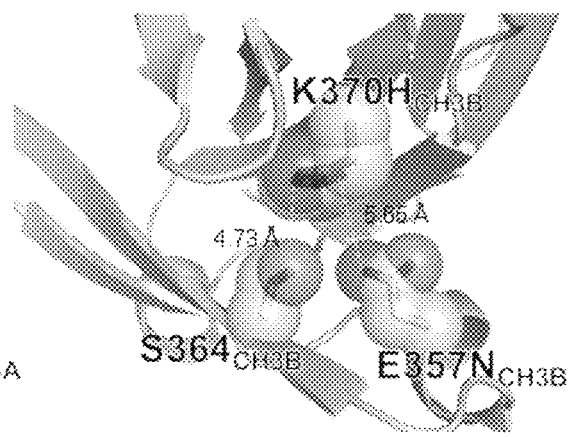
A210 homodimer
(CH3B-CH3B)

[Fig. 21A]
- - - - Distance
⟶ Unpaired charged residue
⟶ Steric clash
······· Hydrogen bond
- - - π-π interaction
- - - - Electrostatic / cation-π interaction
— — Disulfide bond
⟶ Electrostatic / anion-π repulsion
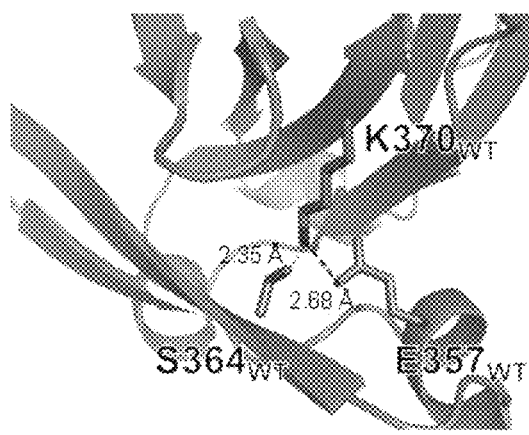
Wild type
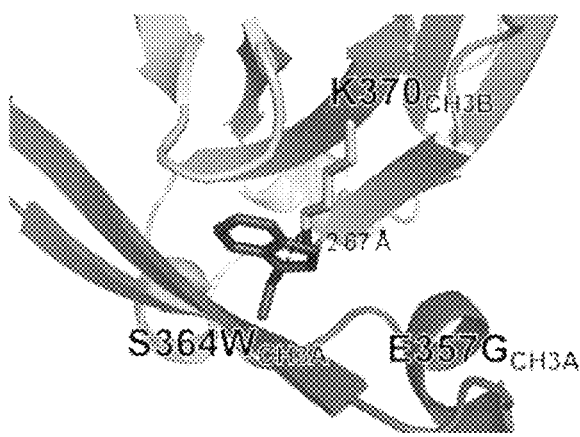
A216 heterodimer
(CH3A-CH3B)
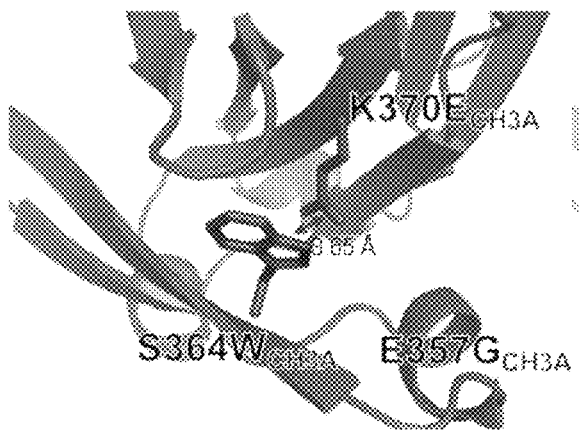
A216 homodimer
(CH3A-CH3A)
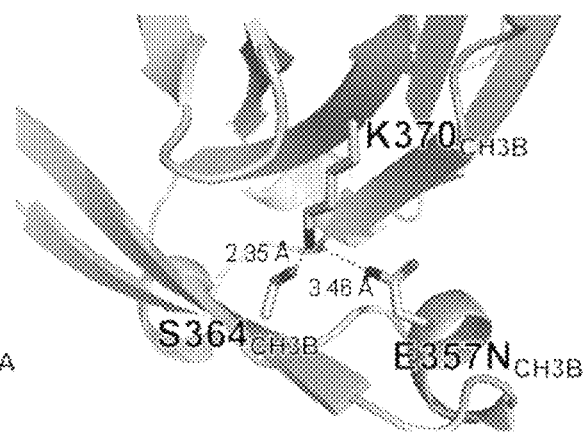
A216 homodimer
(CH3B-CH3B)

[Fig. 21B]
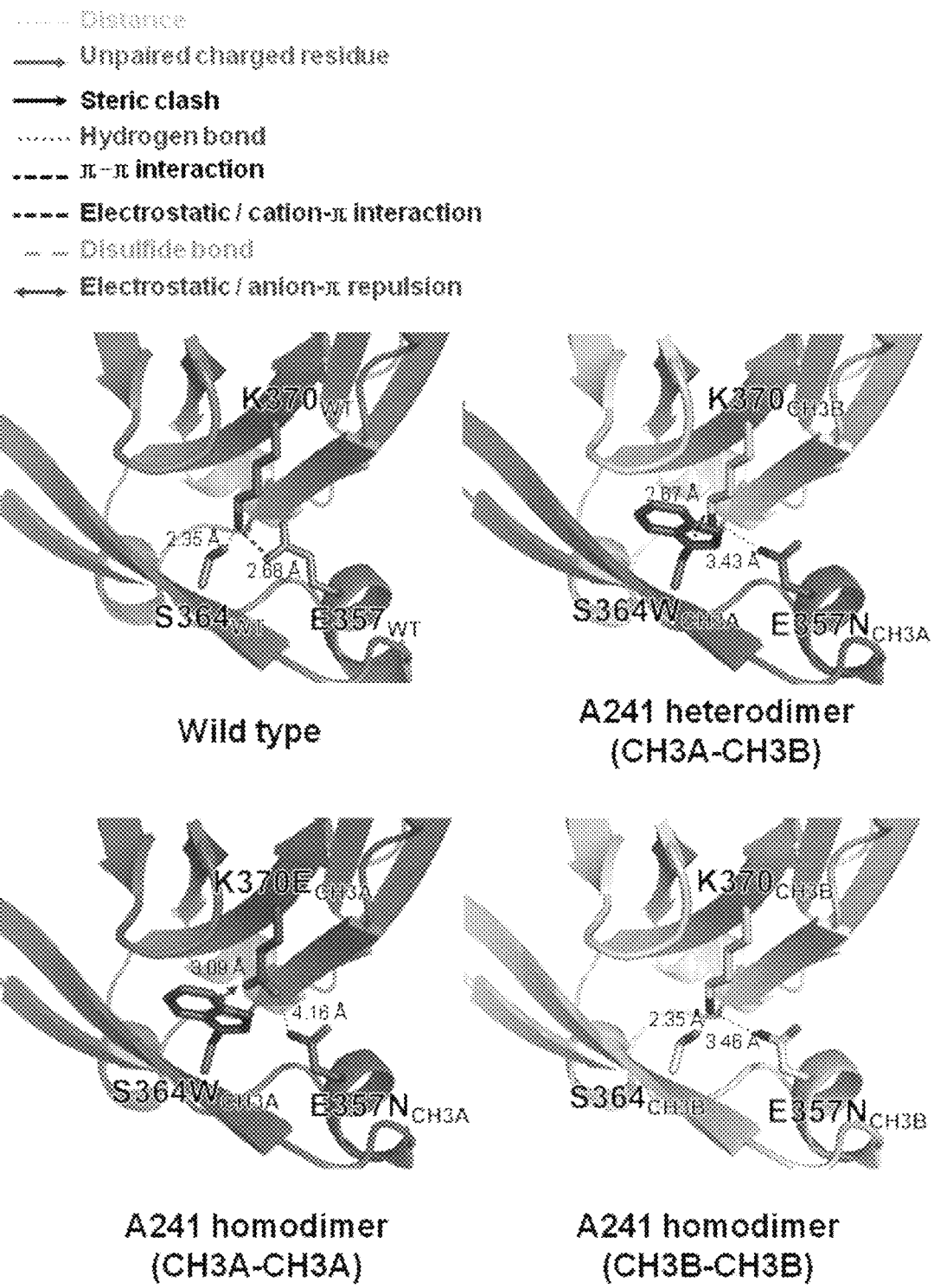

[Fig. 22A]
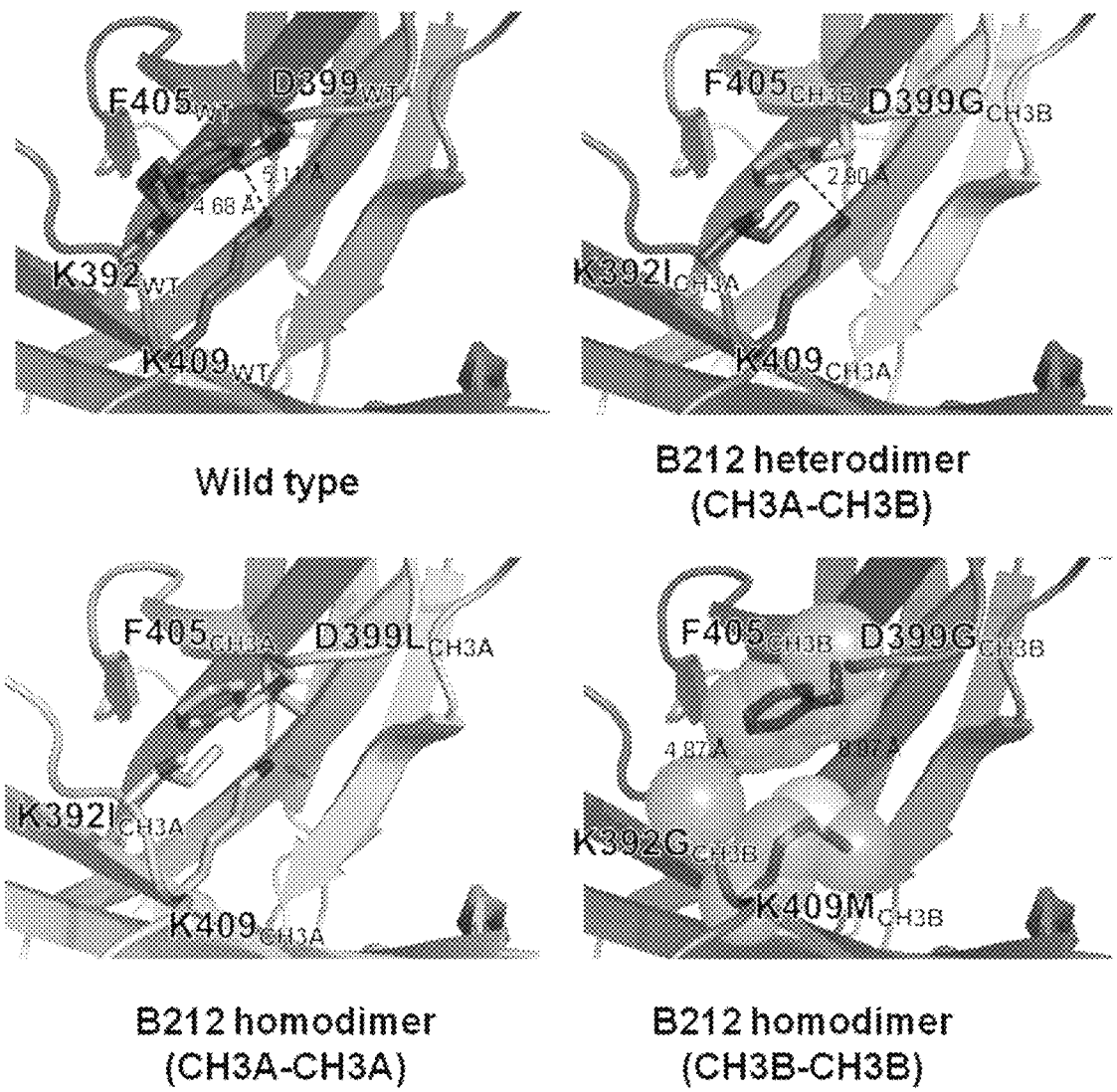

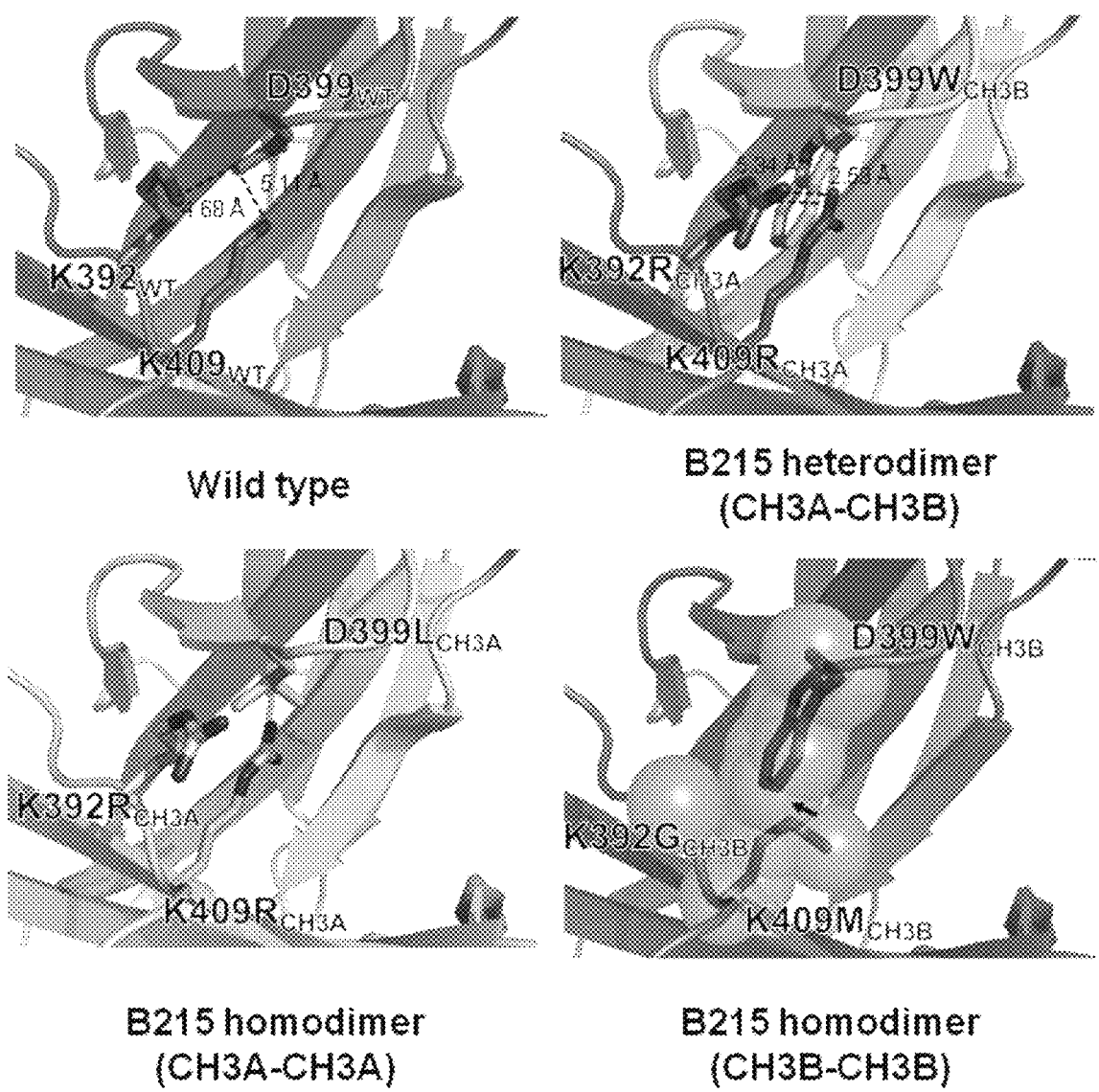

[Fig. 23A]
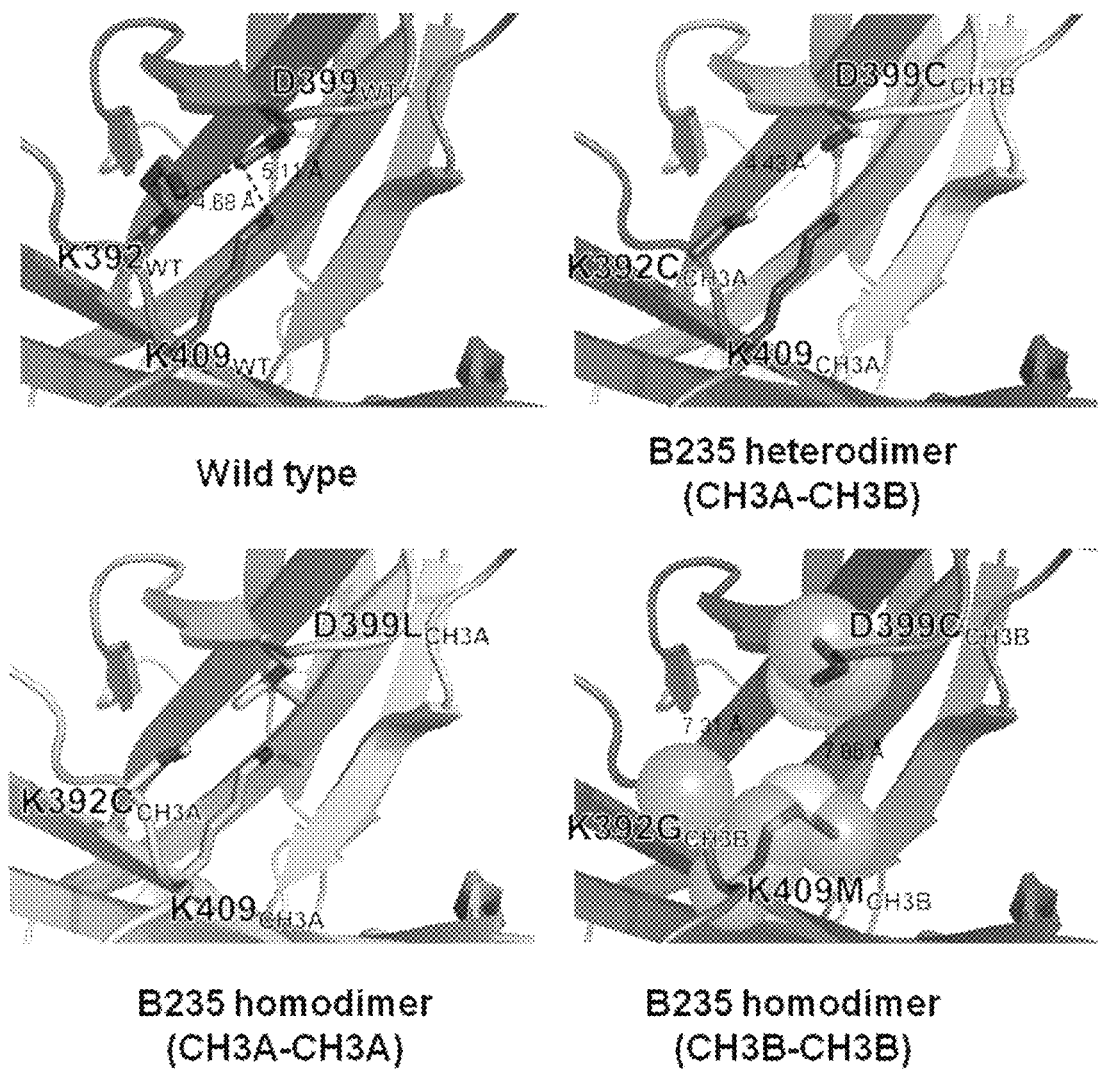

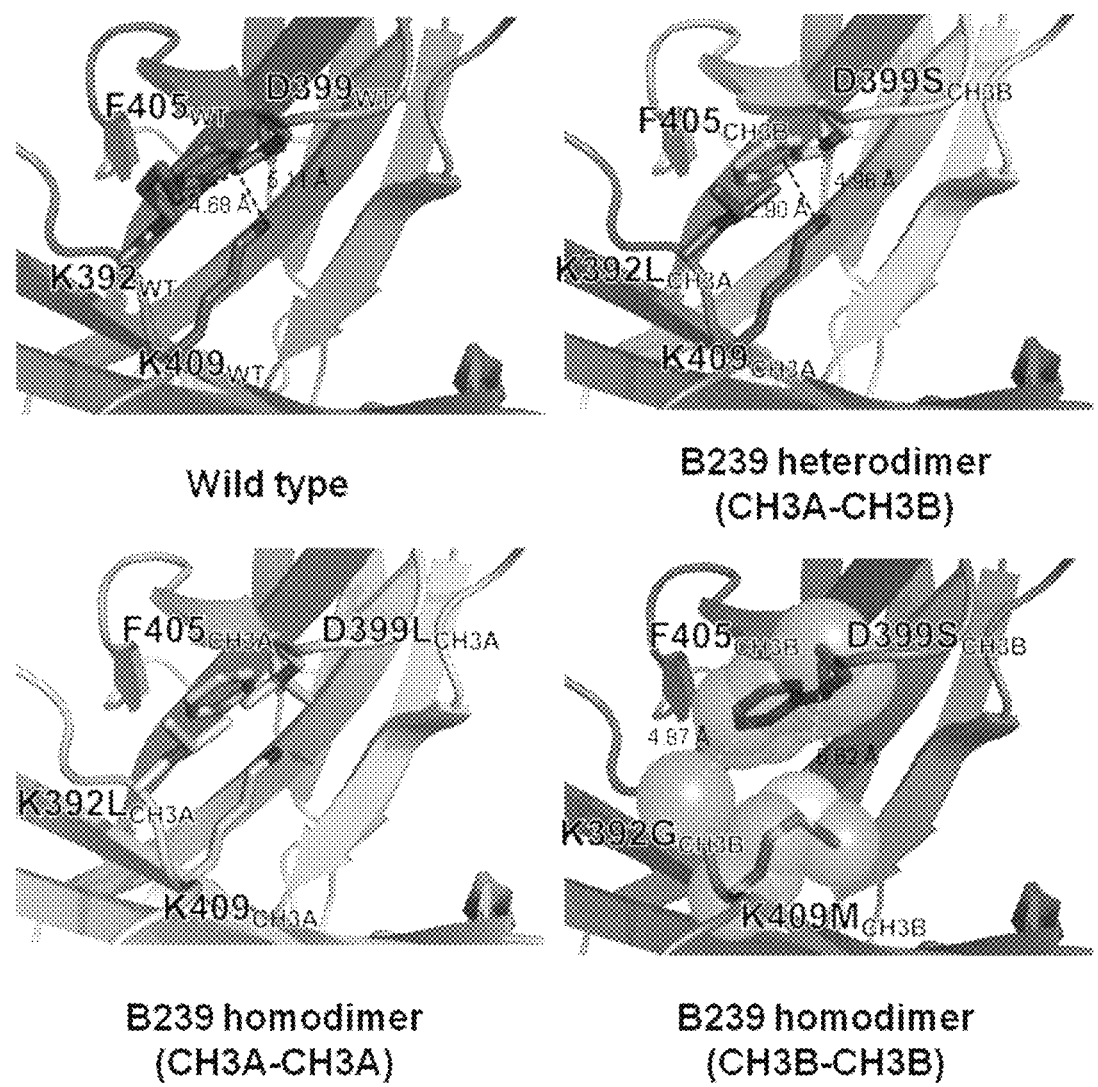
[Fig. 23B]

[Fig. 24A]
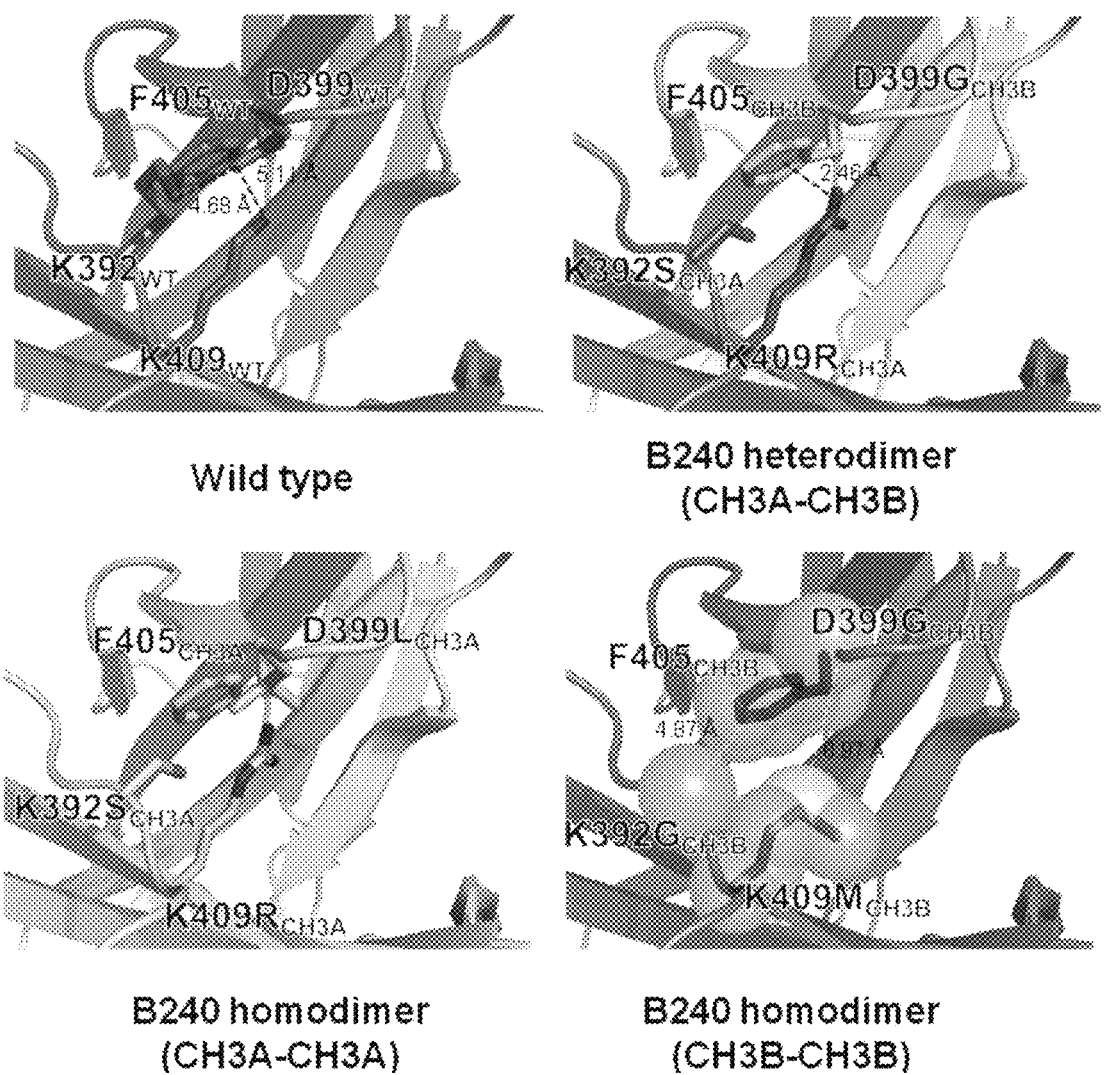

[Fig. 24B]
- ⋯ Distance
- → Unpaired charged residue
- ⟶ Steric clash
- ⋯⋯ Hydrogen bond
- ▬▬ π-π interaction
- ▬▬ Electrostatic / cation-π interaction
- — — Disulfide bond
- ⟵ Electrostatic / anion-π repulsion
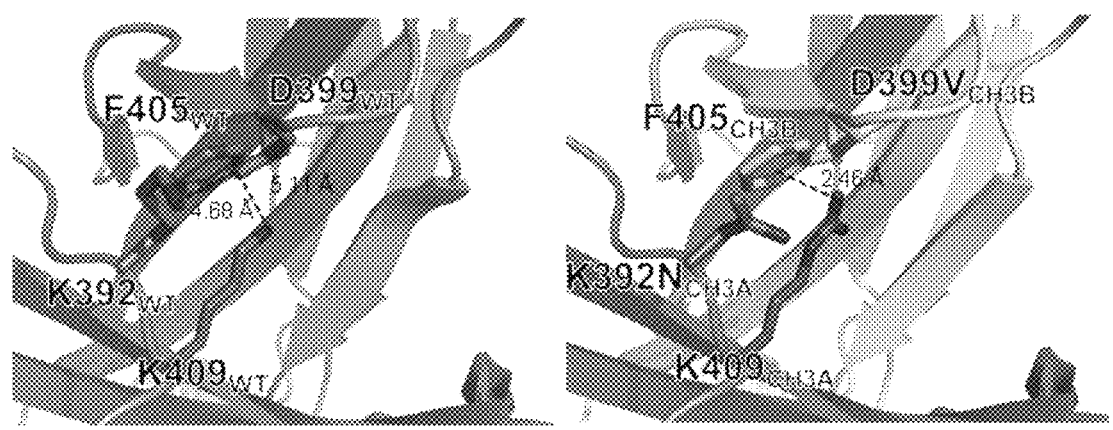
Wild type | B256 heterodimer (CH3A-CH3B)
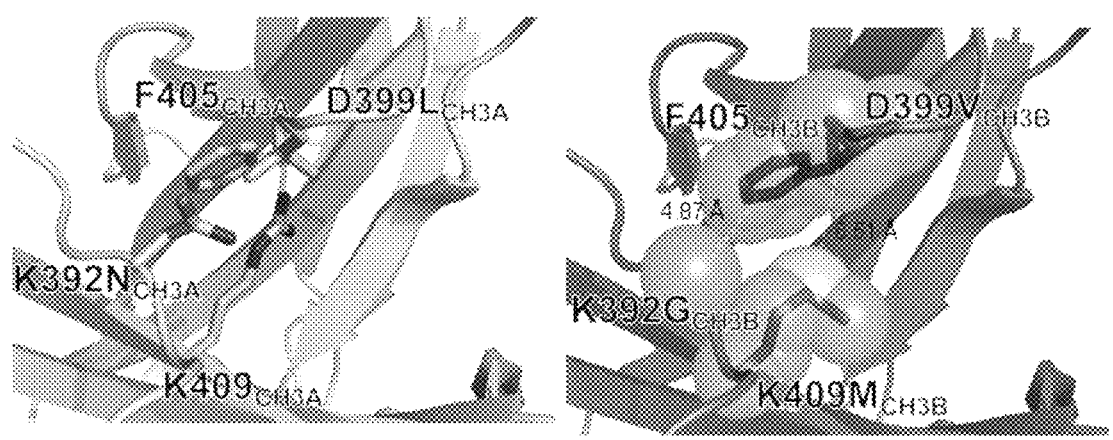
B256 homodimer (CH3A-CH3A) | B256 homodimer (CH3B-CH3B)

[Fig. 25]
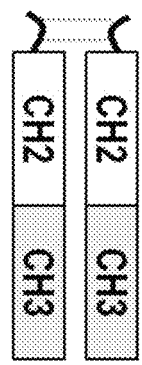 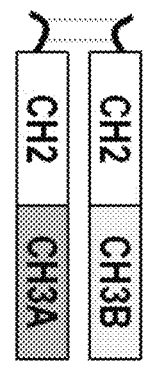
Fc-WT          Fc<sub>CH3A</sub>/Fc<sub>CH3B</sub>
               heterodimer

[Fig. 26]
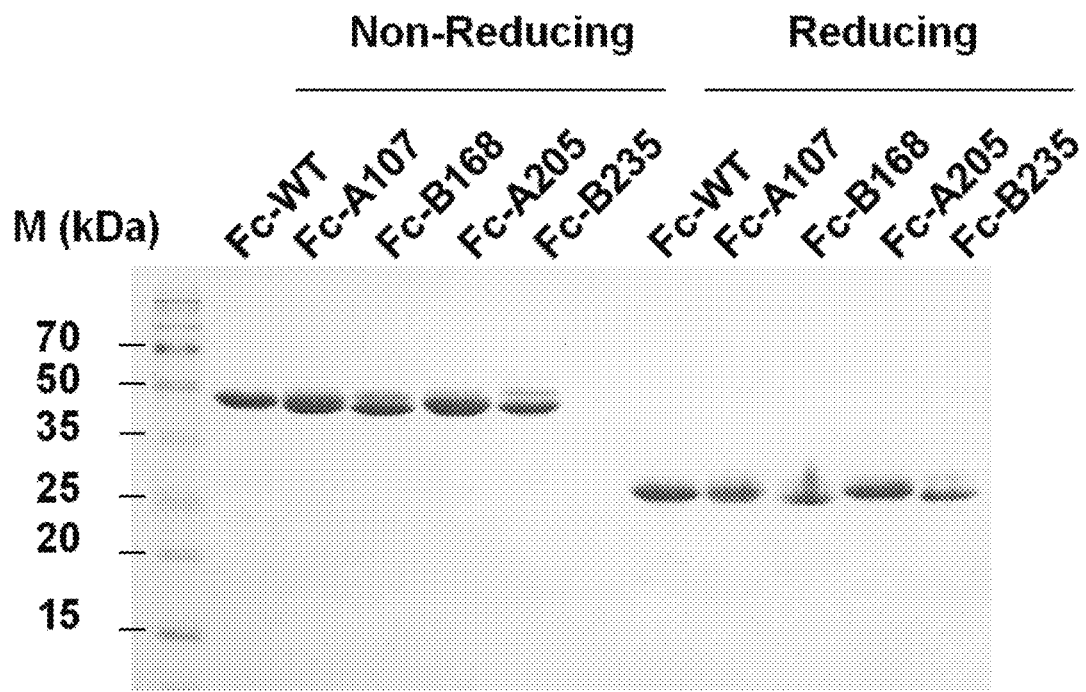
[Fig. 27]
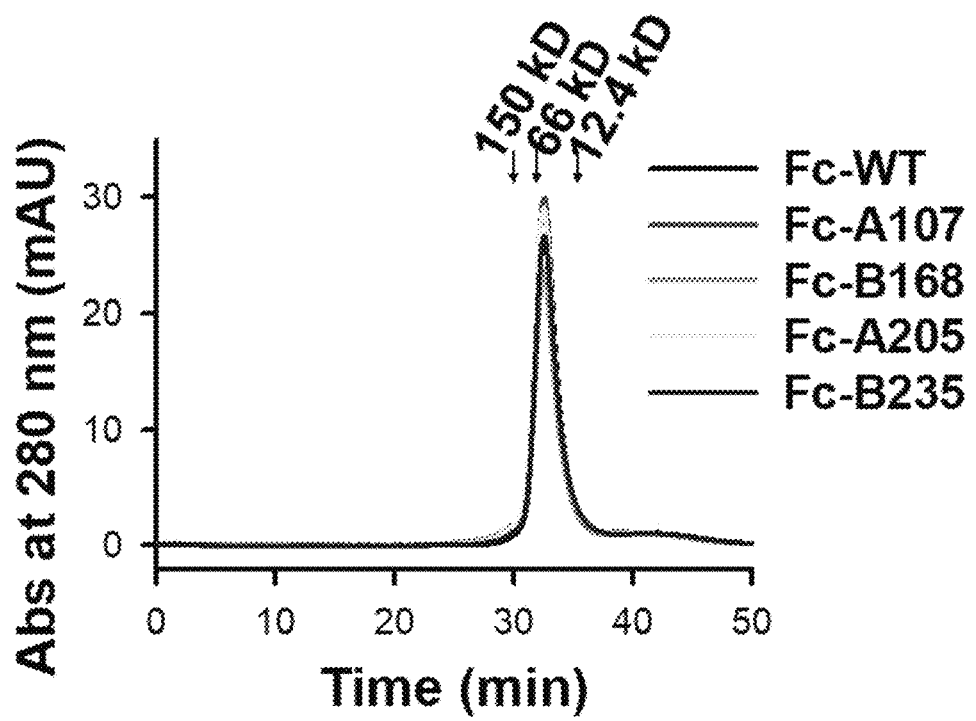

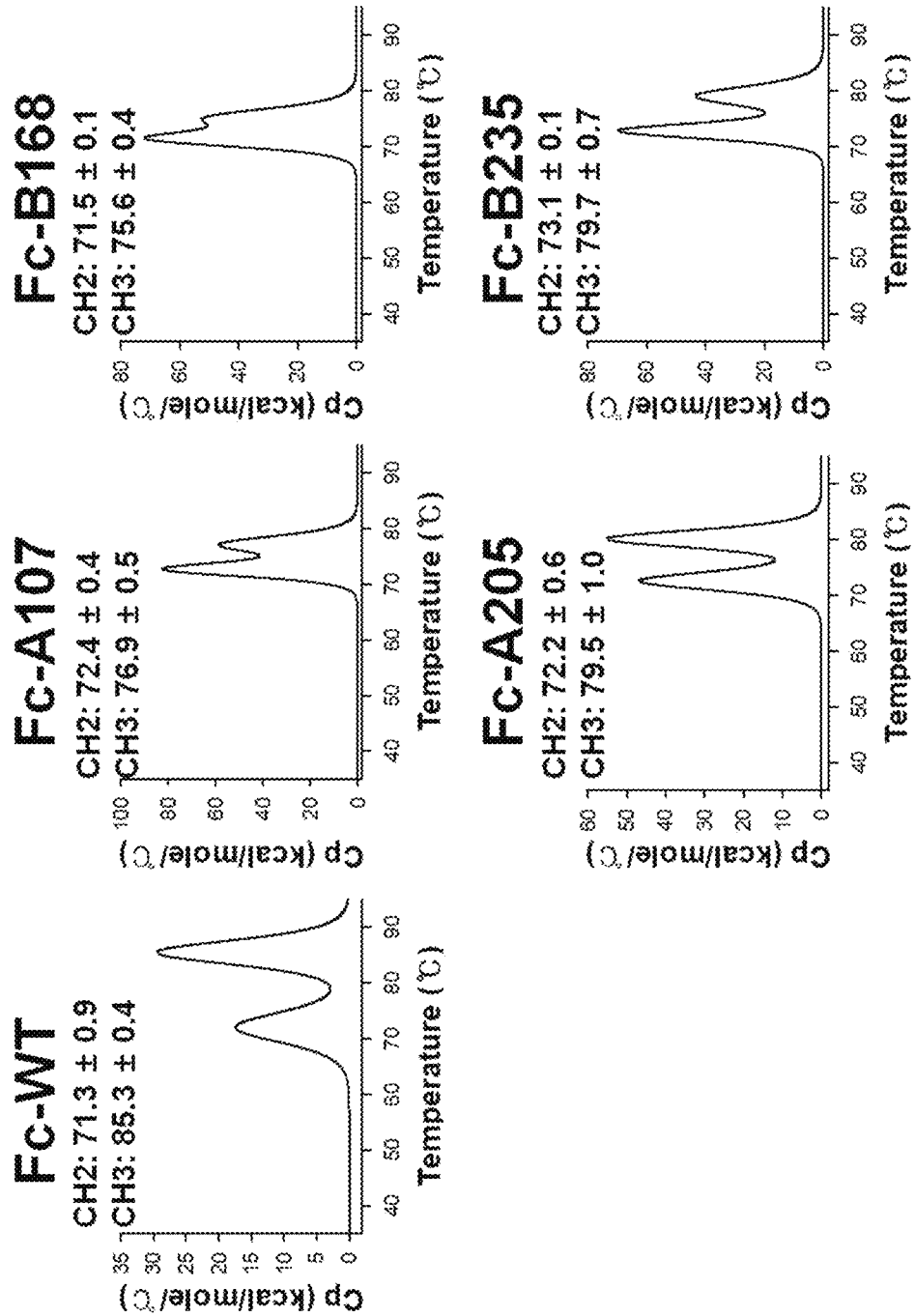
[Fig. 28]

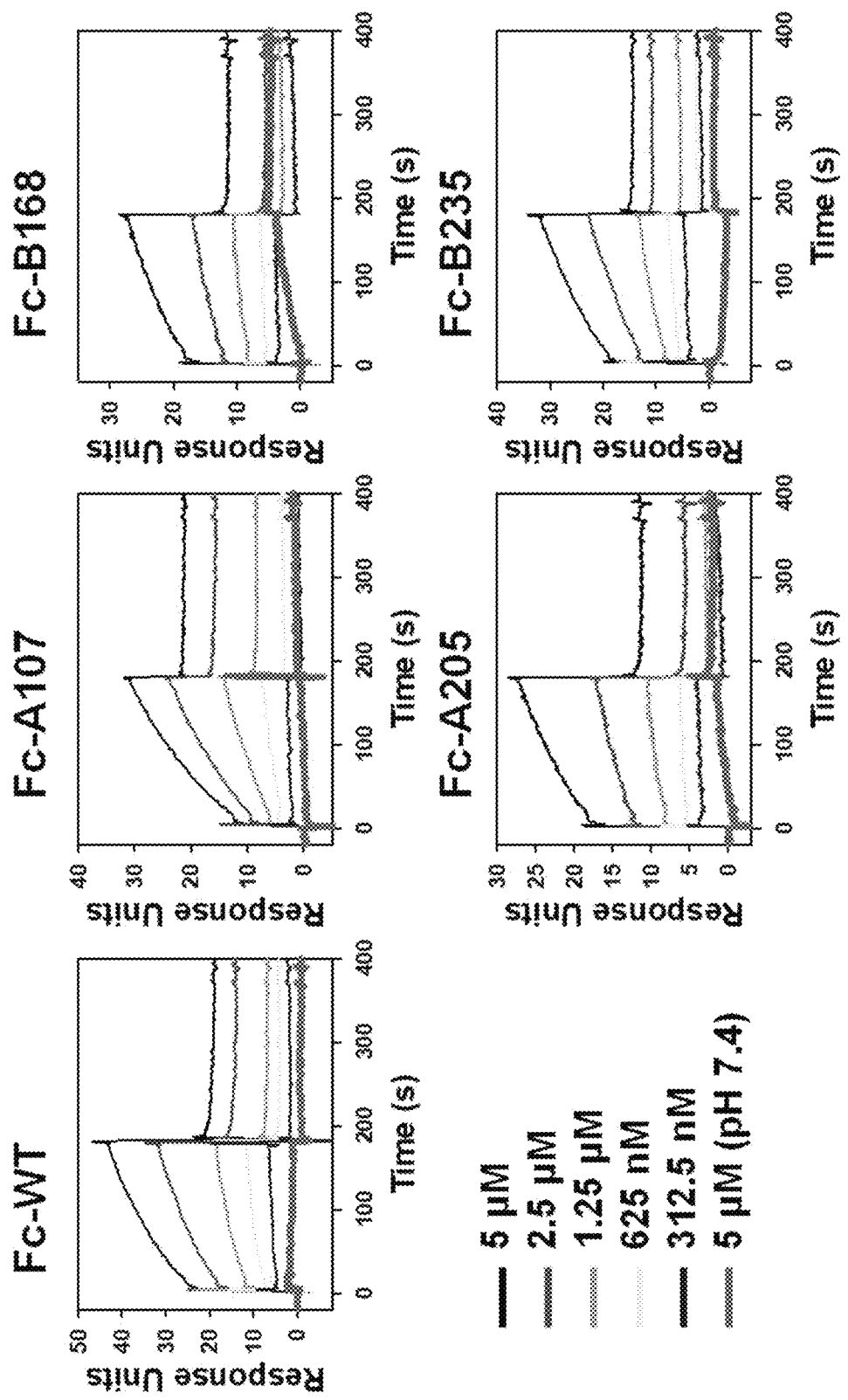
[Fig. 29]

SEQUENCE LISTING

```
<160> NUMBER OF SEQ ID NOS: 132

<210> SEQ ID NO 1
<211> LENGTH: 107
<212> TYPE: PRT
<213> ORGANISM: Artificial Sequence
<220> FEATURE:
<223> OTHER INFORMATION: Wild type CH3A

<400> SEQUENCE: 1

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: W-VT CH3A

<400> SEQUENCE: 2

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Trp Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 3
<211> LENGTH: 107
<212> TYPE: PRT
<213> ORGANISM: Artificial Sequence
<220> FEATURE:
<223> OTHER INFORMATION: W-VT CH3B

<400> SEQUENCE: 3

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Val Ser Asp Gly Ser Phe
    50                  55                  60

Thr Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 4
<211> LENGTH: 107
<212> TYPE: PRT
<213> ORGANISM: Artificial Sequence
<220> FEATURE:
<223> OTHER INFORMATION: EW-RVT CH3A

<400> SEQUENCE: 4

```
Gly Gln Pro Arg Glu Pro Gln Val Tyr Thr Leu Pro Pro Ser Arg Asp
1               5                   10                  15

Glu Leu Thr Glu Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Trp Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 5
<211> LENGTH: 107
<212> TYPE: PRT
<213> ORGANISM: Artificial Sequence
<220> FEATURE:
<223> OTHER INFORMATION: EW-RVT CH3B

<400> SEQUENCE: 5

```
Gly Gln Pro Arg Glu Pro Arg Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30
```

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Val Ser Asp Gly Ser Phe
 50                  55                  60

Thr Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: A107 CH3A

<400> SEQUENCE: 6

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Glu Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Trp Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: A107 CH3B

<400> SEQUENCE: 7

Gly Gln Pro Arg Glu Pro Gln Val Tyr Thr Leu Pro Pro Ser Arg Asp
 1               5                  10                  15

Asn Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Val Ser Asp Gly Ser Phe
 50                  55                  60

Thr Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 8

```
<211> LENGTH: 107
<212> TYPE: PRT
<213> ORGANISM: Artificial Sequence
<220> FEATURE:
<223> OTHER INFORMATION: A108 CH3A

<400> SEQUENCE: 8

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Glu Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Trp Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: A108 CH3B

<400> SEQUENCE: 9

Gly Gln Pro Arg Glu Pro Gln Val Tyr Thr Leu Pro Pro Ser Arg Asp
1               5                   10                  15

Ile Leu Thr Lys Asn Gln Val Thr Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Val Ser Asp Gly Ser Phe
    50                  55                  60

Thr Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: A109 CH3A

<400> SEQUENCE: 10

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Met Gly Phe
            20                  25                  30

Tyr Pro Ser Asp Ile Ala Val Glu Trp Glu Ser Asn Gly Gln Pro Glu
        35                  40                  45
```

```
Asn Asn Tyr Lys Thr Thr Pro Pro Val Leu Asp Ser Asp Gly Ser Phe
 50                  55                  60

Phe Leu Tyr Ser Trp Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 11
<211> LENGTH: 107
<212> TYPE: PRT
<213> ORGANISM: Artificial Sequence
<220> FEATURE:
<223> OTHER INFORMATION: A109 CH3B

<400> SEQUENCE: 11

Gly Gln Pro Arg Glu Pro Gln Val Tyr Thr Leu Pro Pro Ser Arg Asp
 1               5                  10                  15

Met Leu Thr Lys Asn Gln Val Trp Leu Thr Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Val Ser Asp Gly Ser Phe
 50                  55                  60

Thr Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 12
<211> LENGTH: 107
<212> TYPE: PRT
<213> ORGANISM: Artificial Sequence
<220> FEATURE:
<223> OTHER INFORMATION: A146 CH3A

<400> SEQUENCE: 12

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Asp Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
 50                  55                  60

Phe Leu Tyr Ser Trp Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 13
<211> LENGTH: 107
<212> TYPE: PRT
<213> ORGANISM: Artificial Sequence
```

-continued

```
<220> FEATURE:
<223> OTHER INFORMATION: A146 CH3B

<400> SEQUENCE: 13

Gly Gln Pro Arg Glu Pro Gln Val Tyr Thr Leu Pro Pro Ser Arg Asp
1               5                   10                  15

Met Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Val Ser Asp Gly Ser Phe
    50                  55                  60

Thr Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: B121 CH3A

<400> SEQUENCE: 14

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Glu Ser Asp Gly Ser Phe
    50                  55                  60

Phe Leu Tyr Ser Trp Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: B121 CH3B

<400> SEQUENCE: 15

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Glu Thr Thr Pro Pro Val Leu Val Ser Asp Gly Ser Phe
    50                  55                  60
```

Thr Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
            85                  90                  95

Thr Gln Lys Ser Leu Ser Leu Ser Pro Gly Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: B135 CH3A

<400> SEQUENCE: 16

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Leu Ser Asp Gly Ser Phe
    50                  55                  60

Phe Leu Tyr Ser Trp Leu Thr Val Asp Lys Ser Arg Trp Gln Gln Gly
65                  70                  75                  80

Asn Val Phe Ser Cys Ser Val Met His Glu Ala Leu His Asn His Tyr
            85                  90                  95

Thr Gln Lys Ser Leu Ser Leu Ser Pro Gly Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: B135 CH3B

<400> SEQUENCE: 17

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Ser Thr Thr Pro Pro Val Leu Val Ser Asp Gly Ser Phe
    50                  55                  60

Thr Leu Tyr Ser Leu Leu Thr Val Asp Lys Ser Arg Trp Gln Gln Gly
65                  70                  75                  80

Asn Val Phe Ser Cys Ser Val Met His Glu Ala Leu His Asn His Tyr
            85                  90                  95

Thr Gln Lys Ser Leu Ser Leu Ser Pro Gly Lys
            100                 105

<210> SEQ ID NO 18
<211> LENGTH: 107
<212> TYPE: PRT
<213> ORGANISM: Artificial Sequence
<220> FEATURE:
<223> OTHER INFORMATION: B168 CH3A

<400> SEQUENCE: 18

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Leu Ser Asp Gly Ser Phe
    50                  55                  60

Phe Leu Tyr Ser Trp Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: B168 CH3B

<400> SEQUENCE: 19

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Gly Thr Thr Pro Pro Val Leu Val Ser Asp Gly Ser Phe
    50                  55                  60

Thr Leu Tyr Ser Met Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: A205 CH3A

<400> SEQUENCE: 20

Gly Gln Pro Arg Glu Pro Gln Val Tyr Thr Leu Pro Pro Ser Arg Asp
1               5                   10                  15

Asp Leu Thr Lys Asn Gln Val Trp Leu Thr Cys Leu Val Glu Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 21
<211> LENGTH: 107
<212> TYPE: PRT
<213> ORGANISM: Artificial Sequence
<220> FEATURE:
<223> OTHER INFORMATION: A205 CH3B

<400> SEQUENCE: 21

Gly Gln Pro Arg Glu Pro Gln Val Tyr Thr Leu Pro Pro Ser Arg Asp
1               5                   10                  15

Asn Leu Thr Lys Asn Gln Val Ser Leu Thr Cys Leu Val Arg Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: A210 CH3A

<400> SEQUENCE: 22

Gly Gln Pro Arg Glu Pro Gln Val Tyr Thr Leu Pro Pro Ser Arg Asp
1               5                   10                  15

Ala Leu Thr Lys Asn Gln Val Tyr Leu Thr Cys Leu Val Glu Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: A210 CH3B

<400> SEQUENCE: 23

Gly Gln Pro Arg Glu Pro Gln Val Tyr Thr Leu Pro Pro Ser Arg Asp

```
                1               5                   10                  15
Asn Leu Thr Lys Asn Gln Val Ser Leu Thr Cys Leu Val His Gly Phe
                20                  25                  30

Tyr Pro Ser Asp Ile Ala Val Glu Trp Glu Ser Asn Gly Gln Pro Glu
                35                  40                  45

Asn Asn Tyr Lys Thr Thr Pro Pro Val Leu Asp Ser Asp Gly Ser Phe
                50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105

<210> SEQ ID NO 24
<211> LENGTH: 107
<212> TYPE: PRT
<213> ORGANISM: Artificial Sequence
<220> FEATURE:
<223> OTHER INFORMATION: A216 CH3A

<400> SEQUENCE: 24

Gly Gln Pro Arg Glu Pro Gln Val Tyr Thr Leu Pro Pro Ser Arg Asp
1               5                   10                  15

Gly Leu Thr Lys Asn Gln Val Trp Leu Thr Cys Leu Val Glu Gly Phe
                20                  25                  30

Tyr Pro Ser Asp Ile Ala Val Glu Trp Glu Ser Asn Gly Gln Pro Glu
                35                  40                  45

Asn Asn Tyr Lys Thr Thr Pro Pro Val Leu Asp Ser Asp Gly Ser Phe
                50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105

<210> SEQ ID NO 25
<211> LENGTH: 107
<212> TYPE: PRT
<213> ORGANISM: Artificial Sequence
<220> FEATURE:
<223> OTHER INFORMATION: A216 CH3B

<400> SEQUENCE: 25

Gly Gln Pro Arg Glu Pro Gln Val Tyr Thr Leu Pro Pro Ser Arg Asp
1               5                   10                  15

Asn Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
                35                  40                  45

Asn Asn Tyr Lys Thr Thr Pro Pro Val Leu Asp Ser Asp Gly Ser Phe
                50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95
```

Thr Gln Lys Ser Leu Ser Leu Ser Pro Gly Lys
            100                 105

<210> SEQ ID NO 26
<211> LENGTH: 107
<212> TYPE: PRT
<213> ORGANISM: Artificial Sequence
<220> FEATURE:
<223> OTHER INFORMATION: A241 CH3A

<400> SEQUENCE: 26

Gly Gln Pro Arg Glu Pro Gln Val Tyr Thr Leu Pro Pro Ser Arg Asp
1               5                   10                  15

Asn Leu Thr Lys Asn Gln Val Trp Leu Thr Cys Leu Val Glu Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 27
<211> LENGTH: 107
<212> TYPE: PRT
<213> ORGANISM: Artificial Sequence
<220> FEATURE:
<223> OTHER INFORMATION: A241 CH3B

<400> SEQUENCE: 27

Gly Gln Pro Arg Glu Pro Gln Val Tyr Thr Leu Pro Pro Ser Arg Asp
1               5                   10                  15

Asn Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 28
<211> LENGTH: 107
<212> TYPE: PRT
<213> ORGANISM: Artificial Sequence
<220> FEATURE:
<223> OTHER INFORMATION: B212 CH3A

<400> SEQUENCE: 28

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe

```
                20                  25                  30

Tyr Pro Ser Asp Ile Ala Val Glu Trp Glu Ser Asn Gly Gln Pro Glu
            35                  40                  45

Asn Asn Tyr Ile Thr Thr Pro Pro Val Leu Leu Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 29
<211> LENGTH: 107
<212> TYPE: PRT
<213> ORGANISM: Artificial Sequence
<220> FEATURE:
<223> OTHER INFORMATION: B212 CH3B

<400> SEQUENCE: 29

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Gly Thr Thr Pro Pro Val Leu Gly Ser Asp Gly Ser Phe
        50                  55                  60

Phe Leu Tyr Ser Met Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 30
<211> LENGTH: 107
<212> TYPE: PRT
<213> ORGANISM: Artificial Sequence
<220> FEATURE:
<223> OTHER INFORMATION: B215 CH3A

<400> SEQUENCE: 30

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Arg Thr Thr Pro Pro Val Leu Leu Ser Asp Gly Ser Phe
        50                  55                  60

Phe Leu Tyr Ser Arg Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 31
<211> LENGTH: 107
<212> TYPE: PRT
<213> ORGANISM: Artificial Sequence
<220> FEATURE:
<223> OTHER INFORMATION: B215 CH3B

<400> SEQUENCE: 31

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Gly Thr Thr Pro Pro Val Leu Trp Ser Asp Gly Ser Phe
    50                  55                  60

Phe Leu Tyr Ser Met Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: B235 CH3A

<400> SEQUENCE: 32

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Cys Thr Thr Pro Pro Val Leu Leu Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 33
<211> LENGTH: 107
<212> TYPE: PRT
<213> ORGANISM: Artificial Sequence
<220> FEATURE:
<223> OTHER INFORMATION: B235 CH3B

<400> SEQUENCE: 33

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu

```
                35                  40                  45
Asn Asn Tyr Gly Thr Thr Pro Pro Val Leu Cys Ser Asp Gly Ser Phe
 50                  55                  60
Phe Leu Tyr Ser Met Leu Thr Val Asp Lys Ser Arg Trp Gln Gln Gly
 65                  70                  75                  80
Asn Val Phe Ser Cys Ser Val Met His Glu Ala Leu His Asn His Tyr
                 85                  90                  95
Thr Gln Lys Ser Leu Ser Leu Ser Pro Gly Lys
                100                 105
```

<210> SEQ ID NO 34
<211> LENGTH: 223
<212> TYPE: PRT
<213> ORGANISM: Artificial Sequence
<220> FEATURE:
<223> OTHER INFORMATION: B239 CH3A

<400> SEQUENCE: 34

```
Thr Cys Pro Pro Cys Pro Ala Pro Glu Leu Leu Gly Gly Pro Ser Val
 1               5                  10                  15
Phe Leu Phe Pro Pro Lys Pro Lys Asp Thr Leu Met Ile Ser Arg Thr
                20                  25                  30
Pro Glu Val Thr Cys Val Val Val Asp Val Ser His Glu Asp Pro Glu
                35                  40                  45
Val Lys Phe Asn Trp Tyr Val Asp Gly Val Glu Val His Asn Ala Lys
 50                  55                  60
Thr Lys Pro Arg Glu Glu Gln Tyr Asn Ser Thr Tyr Arg Val Val Ser
 65                  70                  75                  80
Val Leu Thr Val Leu His Gln Asp Trp Leu Asn Gly Lys Glu Tyr Lys
                 85                  90                  95
Cys Lys Val Ser Asn Lys Ala Leu Pro Ala Pro Ile Glu Lys Thr Ile
                100                 105                 110
Ser Lys Ala Lys Gly Gln Pro Arg Glu Pro Gln Val Tyr Thr Leu Pro
                115                 120                 125
Pro Ser Arg Asp Glu Leu Thr Lys Asn Gln Val Ser Leu Thr Cys Leu
                130                 135                 140
Val Lys Gly Phe Tyr Pro Ser Asp Ile Ala Val Glu Trp Glu Ser Asn
145                 150                 155                 160
Gly Gln Pro Glu Asn Asn Tyr Leu Thr Thr Pro Pro Val Leu Leu Ser
                165                 170                 175
Asp Gly Ser Phe Phe Leu Tyr Ser Lys Leu Thr Val Asp Lys Ser Arg
                180                 185                 190
Trp Gln Gln Gly Asn Val Phe Ser Cys Ser Val Met His Glu Ala Leu
                195                 200                 205
His Asn His Tyr Thr Gln Lys Ser Leu Ser Leu Ser Pro Gly Lys
                210                 215                 220
```

<210> SEQ ID NO 35
<211> LENGTH: 223
<212> TYPE: PRT
<213> ORGANISM: Artificial Sequence
<220> FEATURE:
<223> OTHER INFORMATION: B239 CH3B

<400> SEQUENCE: 35

```
Thr Cys Pro Pro Cys Pro Ala Pro Glu Leu Leu Gly Gly Pro Ser Val
 1               5                  10                  15
```

Phe Leu Phe Pro Pro Lys Pro Lys Asp Thr Leu Met Ile Ser Arg Thr
                20                  25                  30

Pro Glu Val Thr Cys Val Val Asp Val Ser His Glu Asp Pro Glu
            35                  40                  45

Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Gly Thr Thr Pro Pro Val Leu Ser Ser
                165                 170                 175

Asp Gly Ser Phe Phe Leu Tyr Ser Met Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 36
<211> LENGTH: 107
<212> TYPE: PRT
<213> ORGANISM: Artificial Sequence
<220> FEATURE:
<223> OTHER INFORMATION: B240 CH3A

<400> SEQUENCE: 36

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Ser Thr Thr Pro Pro Val Leu Leu Ser Asp Gly Ser Phe
 50                  55                  60

Phe Leu Tyr Ser Arg Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 37
<211> LENGTH: 107
<212> TYPE: PRT
<213> ORGANISM: Artificial Sequence
<220> FEATURE:
<223> OTHER INFORMATION: B240 CH3B

<400> SEQUENCE: 37

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Gly Thr Thr Pro Pro Val Leu Gly Ser Asp Gly Ser Phe
    50                  55                  60

Phe Leu Tyr Ser Met Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 38
<211> LENGTH: 107
<212> TYPE: PRT
<213> ORGANISM: Artificial Sequence
<220> FEATURE:
<223> OTHER INFORMATION: B256 CH3A

<400> SEQUENCE: 38

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Asn Thr Thr Pro Pro Val Leu Leu Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 39
<211> LENGTH: 107
<212> TYPE: PRT
<213> ORGANISM: Artificial Sequence
<220> FEATURE:
<223> OTHER INFORMATION: B256 CH3B

<400> SEQUENCE: 39

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Gly Thr Thr Pro Pro Val Leu Val Ser Asp Gly Ser Phe
    50                  55                  60

Phe Leu Tyr Ser Met Leu Thr Val Asp Lys Ser Arg Trp Gln Gln Gly
65                  70                  75                  80

Asn Val Phe Ser Cys Ser Val Met His Glu Ala Leu His Asn His Tyr

```
                85                  90                  95

Thr Gln Lys Ser Leu Ser Leu Ser Pro Gly Lys
            100                 105

<210> SEQ ID NO 40
<211> LENGTH: 107
<212> TYPE: PRT
<213> ORGANISM: Artificial Sequence
<220> FEATURE:
<223> OTHER INFORMATION: A107w/oW-VT CH3A

<400> SEQUENCE: 40

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Glu Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 41
<211> LENGTH: 107
<212> TYPE: PRT
<213> ORGANISM: Artificial Sequence
<220> FEATURE:
<223> OTHER INFORMATION: A107w/oW-VT CH3B

<400> SEQUENCE: 41

Gly Gln Pro Arg Glu Pro Gln Val Tyr Thr Leu Pro Pro Ser Arg Asp
1               5                   10                  15

Asn Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 42
<211> LENGTH: 107
<212> TYPE: PRT
<213> ORGANISM: Artificial Sequence
<220> FEATURE:
<223> OTHER INFORMATION: A109w/oW-VT CH3A

<400> SEQUENCE: 42

Gly Gln Pro Arg Glu Pro Gln Val Tyr Thr Leu Pro Pro Ser Arg Asp
1               5                   10                  15
```

Glu Leu Thr Lys Asn Gln Val Ser Leu Thr Cys Leu Val Met Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 43
<211> LENGTH: 107
<212> TYPE: PRT
<213> ORGANISM: Artificial Sequence
<220> FEATURE:
<223> OTHER INFORMATION: A109w/oW-VT CH3B

<400> SEQUENCE: 43

Gly Gln Pro Arg Glu Pro Gln Val Tyr Thr Leu Pro Pro Ser Arg Asp
1               5                   10                  15

Met Leu Thr Lys Asn Gln Val Trp Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 44
<211> LENGTH: 107
<212> TYPE: PRT
<213> ORGANISM: Artificial Sequence
<220> FEATURE:
<223> OTHER INFORMATION: A146w/oW-VT CH3A

<400> SEQUENCE: 44

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Asp Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys

<210> SEQ ID NO 45
<211> LENGTH: 107
<212> TYPE: PRT
<213> ORGANISM: Artificial Sequence
<220> FEATURE:
<223> OTHER INFORMATION: A146w/oW-VT CH3B

<400> SEQUENCE: 45

Gly Gln Pro Arg Glu Pro Gln Val Tyr Thr Leu Pro Pro Ser Arg Asp
1               5                   10                  15

Met Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 46
<211> LENGTH: 107
<212> TYPE: PRT
<213> ORGANISM: Artificial Sequence
<220> FEATURE:
<223> OTHER INFORMATION: B168w/oW-VT CH3A

<400> SEQUENCE: 46

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Leu Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 47
<211> LENGTH: 107
<212> TYPE: PRT
<213> ORGANISM: Artificial Sequence
<220> FEATURE:
<223> OTHER INFORMATION: B168w/oW-VT CH3B

<400> SEQUENCE: 47

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Gly Thr Thr Pro Pro Val Leu Asp Ser Asp Gly Ser Phe
 50                  55                  60

Phe Leu Tyr Ser Met Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 48
<211> LENGTH: 107
<212> TYPE: PRT
<213> ORGANISM: Artificial Sequence
<220> FEATURE:
<223> OTHER INFORMATION: KiH (Genentech) CH3A

<400> SEQUENCE: 48

Gly Gln Pro Arg Glu Pro Gln Val Tyr Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 49
<211> LENGTH: 107
<212> TYPE: PRT
<213> ORGANISM: Artificial Sequence
<220> FEATURE:
<223> OTHER INFORMATION: KiH (Genentech) CH3B

<400> SEQUENCE: 49

Gly Gln Pro Arg Glu Pro Gln Val Tyr Thr Leu Pro Pro Ser Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

```
<210> SEQ ID NO 50
<211> LENGTH: 107
<212> TYPE: PRT
<213> ORGANISM: Artificial Sequence
<220> FEATURE:
<223> OTHER INFORMATION: Hole-Hole (Genentech) CH3A

<400> SEQUENCE: 50

Gly Gln Pro Arg Glu Pro Gln Val Tyr Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 51
<211> LENGTH: 223
<212> TYPE: PRT
<213> ORGANISM: Artificial Sequence
<220> FEATURE:
<223> OTHER INFORMATION: Wild type Fc (CH3A included)

<400> SEQUENCE: 51

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205
```

His Asn His Tyr Thr Gln Lys Ser Leu Ser Leu Ser Pro Gly Lys
    210                 215                 220

<210> SEQ ID NO 52
<211> LENGTH: 223
<212> TYPE: PRT
<213> ORGANISM: Artificial Sequence
<220> FEATURE:
<223> OTHER INFORMATION: W-VT Fc (CH3A included)

<400> SEQUENCE: 52

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Trp Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 53
<211> LENGTH: 223
<212> TYPE: PRT
<213> ORGANISM: Artificial Sequence
<220> FEATURE:
<223> OTHER INFORMATION: W-VT Fc (CH3B included)

<400> SEQUENCE: 53

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
            85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Val Ser
            165                 170                 175

Asp Gly Ser Phe Thr Leu Tyr Ser Lys Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
            210                 215                 220

<210> SEQ ID NO 54
<211> LENGTH: 223
<212> TYPE: PRT
<213> ORGANISM: Artificial Sequence
<220> FEATURE:
<223> OTHER INFORMATION: EW-RVT Fc (CH3A included)

<400> SEQUENCE: 54

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
            85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Glu Leu Thr Glu Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
            165                 170                 175

Asp Gly Ser Phe Phe Leu Tyr Ser Trp Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
            210                 215                 220

<210> SEQ ID NO 55
<211> LENGTH: 223
<212> TYPE: PRT
<213> ORGANISM: Artificial Sequence
<220> FEATURE:
<223> OTHER INFORMATION: EW-RVT Fc (CH3B included)

<400> SEQUENCE: 55

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Arg Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Val Ser
                165                 170                 175

Asp Gly Ser Phe Thr Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 56
<211> LENGTH: 223
<212> TYPE: PRT
<213> ORGANISM: Artificial Sequence
<220> FEATURE:
<223> OTHER INFORMATION: A107 Fc (CH3A included)

<400> SEQUENCE: 56

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
```

```
                    85                  90                  95
Cys Lys Val Ser Asn Lys Ala Leu Pro Ala Pro Ile Glu Lys Thr Ile
                100                 105                 110
Ser Lys Ala Lys Gly Gln Pro Arg Glu Pro Gln Val Tyr Thr Leu Pro
                115                 120                 125
Pro Ser Arg Asp Glu Leu Thr Lys Asn Gln Val Ser Leu Thr Cys Leu
            130                 135                 140
Val Glu Gly Phe Tyr Pro Ser Asp Ile Ala Val Glu Trp Glu Ser Asn
145                 150                 155                 160
Gly Gln Pro Glu Asn Asn Tyr Lys Thr Thr Pro Pro Val Leu Asp Ser
                165                 170                 175
Asp Gly Ser Phe Phe Leu Tyr Ser Trp Leu Thr Val Asp Lys Ser Arg
            180                 185                 190
Trp Gln Gln Gly Asn Val Phe Ser Cys Ser Val Met His Glu Ala Leu
                195                 200                 205
His Asn His Tyr Thr Gln Lys Ser Leu Ser Leu Ser Pro Gly Lys
            210                 215                 220

<210> SEQ ID NO 57
<211> LENGTH: 223
<212> TYPE: PRT
<213> ORGANISM: Artificial Sequence
<220> FEATURE:
<223> OTHER INFORMATION: A107 Fc (CH3B included)

<400> SEQUENCE: 57

Thr Cys Pro Pro Cys Pro Ala Pro Glu Leu Leu Gly Gly Pro Ser Val
1               5                   10                  15
Phe Leu Phe Pro Pro Lys Pro Lys Asp Thr Leu Met Ile Ser Arg Thr
                20                  25                  30
Pro Glu Val Thr Cys Val Val Val Asp Val Ser His Glu Asp Pro Glu
            35                  40                  45
Val Lys Phe Asn Trp Tyr Val Asp Gly Val Glu Val His Asn Ala Lys
50                  55                  60
Thr Lys Pro Arg Glu Glu Gln Tyr Asn Ser Thr Tyr Arg Val Val Ser
65                  70                  75                  80
Val Leu Thr Val Leu His Gln Asp Trp Leu Asn Gly Lys Glu Tyr Lys
                85                  90                  95
Cys Lys Val Ser Asn Lys Ala Leu Pro Ala Pro Ile Glu Lys Thr Ile
                100                 105                 110
Ser Lys Ala Lys Gly Gln Pro Arg Glu Pro Gln Val Tyr Thr Leu Pro
                115                 120                 125
Pro Ser Arg Asp Asn Leu Thr Lys Asn Gln Val Ser Leu Thr Cys Leu
            130                 135                 140
Val Lys Gly Phe Tyr Pro Ser Asp Ile Ala Val Glu Trp Glu Ser Asn
145                 150                 155                 160
Gly Gln Pro Glu Asn Asn Tyr Lys Thr Thr Pro Pro Val Leu Val Ser
                165                 170                 175
Asp Gly Ser Phe Thr Leu Tyr Ser Lys Leu Thr Val Asp Lys Ser Arg
            180                 185                 190
Trp Gln Gln Gly Asn Val Phe Ser Cys Ser Val Met His Glu Ala Leu
                195                 200                 205
His Asn His Tyr Thr Gln Lys Ser Leu Ser Leu Ser Pro Gly Lys
            210                 215                 220
```

```
<210> SEQ ID NO 58
<211> LENGTH: 223
<212> TYPE: PRT
<213> ORGANISM: Artificial Sequence
<220> FEATURE:
<223> OTHER INFORMATION: A108 Fc (CH3A included)

<400> SEQUENCE: 58

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Glu Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Trp Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 59
<211> LENGTH: 223
<212> TYPE: PRT
<213> ORGANISM: Artificial Sequence
<220> FEATURE:
<223> OTHER INFORMATION: A108 Fc (CH3B included)

<400> SEQUENCE: 59

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95
```

-continued

```
Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Ile Leu Thr Lys Asn Gln Val Thr Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Val Ser
                165                 170                 175

Asp Gly Ser Phe Thr Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 60
<211> LENGTH: 223
<212> TYPE: PRT
<213> ORGANISM: Artificial Sequence
<220> FEATURE:
<223> OTHER INFORMATION: A109 Fc (CH3A included)

<400> SEQUENCE: 60

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
            85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Met Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Trp Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 61
<211> LENGTH: 223

```
<212> TYPE: PRT
<213> ORGANISM: Artificial Sequence
<220> FEATURE:
<223> OTHER INFORMATION: A109 Fc (CH3B included)

<400> SEQUENCE: 61
```

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
            35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Met Leu Thr Lys Asn Gln Val Trp Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Val Ser
                165                 170                 175

Asp Gly Ser Phe Thr Leu Tyr Ser Lys Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
            210                 215                 220

```
<210> SEQ ID NO 62
<211> LENGTH: 223
<212> TYPE: PRT
<213> ORGANISM: Artificial Sequence
<220> FEATURE:
<223> OTHER INFORMATION: A146 Fc (CH3A included)

<400> SEQUENCE: 62
```

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
            35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
        130                 135                 140

Val Asp Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Trp Leu Thr Val Asp Lys Ser Arg
                180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
        210                 215                 220

<210> SEQ ID NO 63
<211> LENGTH: 223
<212> TYPE: PRT
<213> ORGANISM: Artificial Sequence
<220> FEATURE:
<223> OTHER INFORMATION: A146 Fc (CH3B included)

<400> SEQUENCE: 63

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Met Leu Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Val Ser
                165                 170                 175

Asp Gly Ser Phe Thr Leu Tyr Ser Lys Leu Thr Val Asp Lys Ser Arg
                180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
        210                 215                 220

<210> SEQ ID NO 64
<211> LENGTH: 223
<212> TYPE: PRT
<213> ORGANISM: Artificial Sequence
<220> FEATURE:
<223> OTHER INFORMATION: B121 Fc (CH3A included)

<400> SEQUENCE: 64

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Glu Ser
                165                 170                 175

Asp Gly Ser Phe Phe Leu Tyr Ser Trp Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 65
<211> LENGTH: 223
<212> TYPE: PRT
<213> ORGANISM: Artificial Sequence
<220> FEATURE:
<223> OTHER INFORMATION: B121 Fc (CH3B included)

<400> SEQUENCE: 65

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro

```
            115                 120                 125
Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Glu Thr Thr Pro Pro Val Leu Val Ser
                165                 170                 175

Asp Gly Ser Phe Thr Leu Tyr Ser Lys Leu Thr Val Asp Lys Ser Arg
            180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
    210                 215                 220

<210> SEQ ID NO 66
<211> LENGTH: 223
<212> TYPE: PRT
<213> ORGANISM: Artificial Sequence
<220> FEATURE:
<223> OTHER INFORMATION: B135 Fc (CH3A included)

<400> SEQUENCE: 66

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Leu Ser
                165                 170                 175

Asp Gly Ser Phe Phe Leu Tyr Ser Trp Leu Thr Val Asp Lys Ser Arg
            180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
    210                 215                 220

<210> SEQ ID NO 67
<211> LENGTH: 223
<212> TYPE: PRT
<213> ORGANISM: Artificial Sequence
<220> FEATURE:
<223> OTHER INFORMATION: B135 Fc (CH3B included)
```

<400> SEQUENCE: 67

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
                35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Ser Thr Thr Pro Pro Val Leu Val Ser
                165                 170                 175

Asp Gly Ser Phe Thr Leu Tyr Ser Leu Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
            210                 215                 220
```

<210> SEQ ID NO 68
<211> LENGTH: 223
<212> TYPE: PRT
<213> ORGANISM: Artificial Sequence
<220> FEATURE:
<223> OTHER INFORMATION: B168 Fc (CH3A included)

<400> SEQUENCE: 68

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
                35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
            115                 120                 125
```

```
Pro Ser Arg Asp Glu Leu Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Leu Ser
                165                 170                 175

Asp Gly Ser Phe Phe Leu Tyr Ser Trp Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
    210                 215                 220
```

<210> SEQ ID NO 69
<211> LENGTH: 223
<212> TYPE: PRT
<213> ORGANISM: Artificial Sequence
<220> FEATURE:
<223> OTHER INFORMATION: B168 Fc (CH3B included)

<400> SEQUENCE: 69

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Gly Thr Thr Pro Pro Val Leu Val Ser
                165                 170                 175

Asp Gly Ser Phe Thr Leu Tyr Ser Met Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
    210                 215                 220
```

<210> SEQ ID NO 70
<211> LENGTH: 223
<212> TYPE: PRT
<213> ORGANISM: Artificial Sequence
<220> FEATURE:
<223> OTHER INFORMATION: A205 Fc (CH3A included)

<400> SEQUENCE: 70

Thr Cys Pro Pro Cys Pro Ala Pro Glu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
            35                  40                  45

Val Lys Phe Asn Trp Tyr Val Asp Gly Val Glu Val His Asn Ala Lys
50                  55                      60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Arg Asp Asp Leu Thr Lys Asn Gln Val Trp Leu Thr Cys Leu
            130                 135                 140

Val Glu Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
            210                 215                 220

<210> SEQ ID NO 71
<211> LENGTH: 223
<212> TYPE: PRT
<213> ORGANISM: Artificial Sequence
<220> FEATURE:
<223> OTHER INFORMATION: A205 Fc (CH3 included)

<400> SEQUENCE: 71

Thr Cys Pro Pro Cys Pro Ala Pro Glu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
            35                  40                  45

Val Lys Phe Asn Trp Tyr Val Asp Gly Val Glu Val His Asn Ala Lys
50                  55                      60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Arg Asp Asn Leu Thr Lys Asn Gln Val Ser Leu Thr Cys Leu
            130                 135                 140

Val Arg Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 72
<211> LENGTH: 223
<212> TYPE: PRT
<213> ORGANISM: Artificial Sequence
<220> FEATURE:
<223> OTHER INFORMATION: A210 Fc (CH3A included)

<400> SEQUENCE: 72

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Asp Val Ser His Glu Asp Pro Glu
            35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Ala Leu Thr Lys Asn Gln Val Tyr Leu Thr Cys Leu
    130                 135                 140

Val Glu Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 73
<211> LENGTH: 223
<212> TYPE: PRT
<213> ORGANISM: Artificial Sequence
<220> FEATURE:
<223> OTHER INFORMATION: A210 Fc (CH3B included)

<400> SEQUENCE: 73

Thr Cys Pro Pro Cys Pro Ala Pro Glu Leu Leu Gly Gly Pro Ser Val

```
                1               5                  10                 15
            Phe Leu Phe Pro Pro Lys Pro Lys Asp Thr Leu Met Ile Ser Arg Thr
                            20                 25                 30

Pro Glu Val Thr Cys Val Val Val Asp Val Ser His Glu Asp Pro Glu
                        35                 40                 45

Val Lys Phe Asn Trp Tyr Val Asp Gly Val Glu Val His Asn Ala Lys
                    50                 55                 60

Thr Lys Pro Arg Glu Glu Gln Tyr Asn Ser Thr Tyr Arg Val Val Ser
            65                 70                 75                 80

Val Leu Thr Val Leu His Gln Asp Trp Leu Asn Gly Lys Glu Tyr Lys
                            85                 90                 95

Cys Lys Val Ser Asn Lys Ala Leu Pro Ala Pro Ile Glu Lys Thr Ile
                            100                105                110

Ser Lys Ala Lys Gly Gln Pro Arg Glu Pro Gln Val Tyr Thr Leu Pro
                            115                120                125

Pro Ser Arg Asp Asn Leu Thr Lys Asn Gln Val Ser Leu Thr Cys Leu
                        130                135                140

Val His Gly Phe Tyr Pro Ser Asp Ile Ala Val Glu Trp Glu Ser Asn
            145                150                155                160

Gly Gln Pro Glu Asn Asn Tyr Lys Thr Thr Pro Pro Val Leu Asp Ser
                            165                170                175

Asp Gly Ser Phe Phe Leu Tyr Ser Lys Leu Thr Val Asp Lys Ser Arg
                            180                185                190

Trp Gln Gln Gly Asn Val Phe Ser Cys Ser Val Met His Glu Ala Leu
                            195                200                205

His Asn His Tyr Thr Gln Lys Ser Leu Ser Leu Ser Pro Gly Lys
                            210                215                220

<210> SEQ ID NO 74
<211> LENGTH: 223
<212> TYPE: PRT
<213> ORGANISM: Artificial Sequence
<220> FEATURE:
<223> OTHER INFORMATION: A216 Fc (CH3A included)

<400> SEQUENCE: 74

Thr Cys Pro Pro Cys Pro Ala Pro Glu Leu Leu Gly Gly Pro Ser Val
            1               5                  10                 15

Phe Leu Phe Pro Pro Lys Pro Lys Asp Thr Leu Met Ile Ser Arg Thr
                            20                 25                 30

Pro Glu Val Thr Cys Val Val Val Asp Val Ser His Glu Asp Pro Glu
                        35                 40                 45

Val Lys Phe Asn Trp Tyr Val Asp Gly Val Glu Val His Asn Ala Lys
                    50                 55                 60

Thr Lys Pro Arg Glu Glu Gln Tyr Asn Ser Thr Tyr Arg Val Val Ser
            65                 70                 75                 80

Val Leu Thr Val Leu His Gln Asp Trp Leu Asn Gly Lys Glu Tyr Lys
                            85                 90                 95

Cys Lys Val Ser Asn Lys Ala Leu Pro Ala Pro Ile Glu Lys Thr Ile
                            100                105                110

Ser Lys Ala Lys Gly Gln Pro Arg Glu Pro Gln Val Tyr Thr Leu Pro
                            115                120                125

Pro Ser Arg Asp Gly Leu Thr Lys Asn Gln Val Trp Leu Thr Cys Leu
                        130                135                140

Val Glu Gly Phe Tyr Pro Ser Asp Ile Ala Val Glu Trp Glu Ser Asn
```

```
              145                 150                 155                 160
Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
    210                 215                 220

<210> SEQ ID NO 75
<211> LENGTH: 223
<212> TYPE: PRT
<213> ORGANISM: Artificial Sequence
<220> FEATURE:
<223> OTHER INFORMATION: A216 Fc (CH3B included)

<400> SEQUENCE: 75

Thr Cys Pro Pro Cys Pro Ala Pro Glu Leu Leu Gly Gly Pro Ser Val
1               5                  10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
        50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Asn Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
    210                 215                 220

<210> SEQ ID NO 76
<211> LENGTH: 223
<212> TYPE: PRT
<213> ORGANISM: Artificial Sequence
<220> FEATURE:
<223> OTHER INFORMATION: A241 Fc (CH3A included)

<400> SEQUENCE: 76

Thr Cys Pro Pro Cys Pro Ala Pro Glu Leu Leu Gly Gly Pro Ser Val
1               5                  10                  15
```

```
Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Arg Asp Asn Leu Thr Lys Asn Gln Val Trp Leu Thr Cys Leu
        130                 135                 140

Val Glu Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
        210                 215                 220

<210> SEQ ID NO 77
<211> LENGTH: 223
<212> TYPE: PRT
<213> ORGANISM: Artificial Sequence
<220> FEATURE:
<223> OTHER INFORMATION: A241 Fc (CH3B included)

<400> SEQUENCE: 77

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Arg Asp Asn Leu Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160
```

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 78
<211> LENGTH: 223
<212> TYPE: PRT
<213> ORGANISM: Artificial Sequence
<220> FEATURE:
<223> OTHER INFORMATION: B212 Fc (CH3A included)

<400> SEQUENCE: 78

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Ile Thr Thr Pro Pro Val Leu Leu Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 79
<211> LENGTH: 223
<212> TYPE: PRT
<213> ORGANISM: Artificial Sequence
<220> FEATURE:
<223> OTHER INFORMATION: B212 Fc (CH3B included)

<400> SEQUENCE: 79

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

```
Pro Glu Val Thr Cys Val Val Asp Val Ser His Glu Asp Pro Glu
         35                  40                  45

Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
                115                 120                 125

Pro Ser Arg Asp Glu Leu Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Gly Thr Thr Pro Pro Val Leu Gly Ser
                165                 170                 175

Asp Gly Ser Phe Phe Leu Tyr Ser Met Leu Thr Val Asp Lys Ser Arg
                180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
                210                 215                 220

<210> SEQ ID NO 80
<211> LENGTH: 223
<212> TYPE: PRT
<213> ORGANISM: Artificial Sequence
<220> FEATURE:
<223> OTHER INFORMATION: B215 Fc (CH3A included)

<400> SEQUENCE: 80

Thr Cys Pro Pro Cys Pro Ala Pro Glu Leu Leu Gly Gly Pro Ser Val
 1               5                  10                  15

Phe Leu Phe Pro Pro Lys Pro Lys Asp Thr Leu Met Ile Ser Arg Thr
                 20                  25                  30

Pro Glu Val Thr Cys Val Val Asp Val Ser His Glu Asp Pro Glu
         35                  40                  45

Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
                115                 120                 125

Pro Ser Arg Asp Glu Leu Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Arg Thr Thr Pro Pro Val Leu Leu Ser
                165                 170                 175
```

-continued

```
Asp Gly Ser Phe Phe Leu Tyr Ser Arg Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
            210                 215                 220

<210> SEQ ID NO 81
<211> LENGTH: 223
<212> TYPE: PRT
<213> ORGANISM: Artificial Sequence
<220> FEATURE:
<223> OTHER INFORMATION: B215 Fc (CH3B included)

<400> SEQUENCE: 81

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Gly Thr Thr Pro Pro Val Leu Trp Ser
                165                 170                 175

Asp Gly Ser Phe Phe Leu Tyr Ser Met Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
            210                 215                 220

<210> SEQ ID NO 82
<211> LENGTH: 223
<212> TYPE: PRT
<213> ORGANISM: Artificial Sequence
<220> FEATURE:
<223> OTHER INFORMATION: B235 Fc (CH3A included)

<400> SEQUENCE: 82

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
```

```
            35                  40                  45
Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
                115                 120                 125

Pro Ser Arg Asp Glu Leu Thr Lys Asn Gln Val Ser Leu Thr Cys Leu
                130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Cys Thr Thr Pro Pro Val Leu Leu Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
                210                 215                 220

<210> SEQ ID NO 83
<211> LENGTH: 223
<212> TYPE: PRT
<213> ORGANISM: Artificial Sequence
<220> FEATURE:
<223> OTHER INFORMATION: B235 Fc (CH3B included)

<400> SEQUENCE: 83

Thr Cys Pro Pro Cys Pro Ala Pro Glu Leu Leu Gly Gly Pro Ser Val
 1               5                  10                  15

Phe Leu Phe Pro Pro Lys Pro Lys Asp Thr Leu Met Ile Ser Arg Thr
                 20                  25                  30

Pro Glu Val Thr Cys Val Val Val Asp Val Ser His Glu Asp Pro Glu
                 35                  40                  45

Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
                115                 120                 125

Pro Ser Arg Asp Glu Leu Thr Lys Asn Gln Val Ser Leu Thr Cys Leu
                130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Gly Thr Thr Pro Pro Val Leu Cys Ser
                165                 170                 175

Asp Gly Ser Phe Phe Leu Tyr Ser Met Leu Thr Val Asp Lys Ser Arg
```

```
                180             185                 190
Trp Gln Gln Gly Asn Val Phe Ser Cys Ser Val Met His Glu Ala Leu
            195                 200             205

His Asn His Tyr Thr Gln Lys Ser Leu Ser Leu Ser Pro Gly Lys
        210                 215             220

<210> SEQ ID NO 84
<211> LENGTH: 223
<212> TYPE: PRT
<213> ORGANISM: Artificial Sequence
<220> FEATURE:
<223> OTHER INFORMATION: B239 Fc (CH3A included)

<400> SEQUENCE: 84

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Leu Thr Thr Pro Pro Val Leu Leu Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 85
<211> LENGTH: 223
<212> TYPE: PRT
<213> ORGANISM: Artificial Sequence
<220> FEATURE:
<223> OTHER INFORMATION: B239 Fc (CH3B included)

<400> SEQUENCE: 85

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45
```

```
Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
                115                 120                 125

Pro Ser Arg Asp Glu Leu Thr Lys Asn Gln Val Ser Leu Thr Cys Leu
            130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Gly Thr Thr Pro Pro Val Leu Ser Ser
                165                 170                 175

Asp Gly Ser Phe Phe Leu Tyr Ser Met Leu Thr Val Asp Lys Ser Arg
                180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
            210                 215                 220

<210> SEQ ID NO 86
<211> LENGTH: 223
<212> TYPE: PRT
<213> ORGANISM: Artificial Sequence
<220> FEATURE:
<223> OTHER INFORMATION: B240 Fc (CH3A included)

<400> SEQUENCE: 86

Thr Cys Pro Pro Cys Pro Ala Pro Glu Leu Leu Gly Gly Pro Ser Val
 1               5                  10                  15

Phe Leu Phe Pro Pro Lys Pro Lys Asp Thr Leu Met Ile Ser Arg Thr
                 20                  25                  30

Pro Glu Val Thr Cys Val Val Asp Val Ser His Glu Asp Pro Glu
             35                  40                  45

Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
                115                 120                 125

Pro Ser Arg Asp Glu Leu Thr Lys Asn Gln Val Ser Leu Thr Cys Leu
            130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Ser Thr Thr Pro Pro Val Leu Leu Ser
                165                 170                 175

Asp Gly Ser Phe Phe Leu Tyr Ser Arg Leu Thr Val Asp Lys Ser Arg
                180                 185                 190
```

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 87
<211> LENGTH: 223
<212> TYPE: PRT
<213> ORGANISM: Artificial Sequence
<220> FEATURE:
<223> OTHER INFORMATION: B240 Fc (CH3B included)

<400> SEQUENCE: 87

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Gly Thr Thr Pro Pro Val Leu Gly Ser
                165                 170                 175

Asp Gly Ser Phe Phe Leu Tyr Ser Met Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 88
<211> LENGTH: 223
<212> TYPE: PRT
<213> ORGANISM: Artificial Sequence
<220> FEATURE:
<223> OTHER INFORMATION: B256 Fc (CH3A included)

<400> SEQUENCE: 88

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

```
Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
             85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Asn Thr Thr Pro Pro Val Leu Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
        210                 215                 220

<210> SEQ ID NO 89
<211> LENGTH: 223
<212> TYPE: PRT
<213> ORGANISM: Artificial Sequence
<220> FEATURE:
<223> OTHER INFORMATION: B256 Fc (CH3B included)

<400> SEQUENCE: 89

Thr Cys Pro Pro Cys Pro Ala Pro Glu Leu Leu Gly Gly Pro Ser Val
  1               5                  10                  15

Phe Leu Phe Pro Pro Lys Pro Lys Asp Thr Leu Met Ile Ser Arg Thr
             20                  25                  30

Pro Glu Val Thr Cys Val Val Val Asp Val Ser His Glu Asp Pro Glu
         35                  40                  45

Val Lys Phe Asn Trp Tyr Val Asp Gly Val Glu Val His Asn Ala Lys
     50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
             85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Gly Thr Thr Pro Pro Val Leu Val Ser
                165                 170                 175

Asp Gly Ser Phe Phe Leu Tyr Ser Met Leu Thr Val Asp Lys Ser Arg
                180                 185                 190

Trp Gln Gln Gly Asn Val Phe Ser Cys Ser Val Met His Glu Ala Leu
            195                 200                 205
```

His Asn His Tyr Thr Gln Lys Ser Leu Ser Leu Ser Pro Gly Lys
    210                 215                 220

<210> SEQ ID NO 90
<211> LENGTH: 223
<212> TYPE: PRT
<213> ORGANISM: Artificial Sequence
<220> FEATURE:
<223> OTHER INFORMATION: A107w/oW-VT Fc (CH3A included)

<400> SEQUENCE: 90

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Glu Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 91
<211> LENGTH: 223
<212> TYPE: PRT
<213> ORGANISM: Artificial Sequence
<220> FEATURE:
<223> OTHER INFORMATION: A107w/oW-VT Fc (CH3B included)

<400> SEQUENCE: 91

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser

```
            65                  70                  75                  80
Val Leu Thr Val Leu His Gln Asp Trp Leu Asn Gly Lys Glu Tyr Lys
                    85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
                115                 120                 125

Pro Ser Arg Asp Asn Leu Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
        210                 215                 220

<210> SEQ ID NO 92
<211> LENGTH: 223
<212> TYPE: PRT
<213> ORGANISM: Artificial Sequence
<220> FEATURE:
<223> OTHER INFORMATION: A109w/oW-VT Fc (CH3A included)

<400> SEQUENCE: 92

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
                115                 120                 125

Pro Ser Arg Asp Glu Leu Thr Lys Asn Gln Val Ser Leu Thr Cys Leu
        130                 135                 140

Val Met Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
```

<210> SEQ ID NO 93
<211> LENGTH: 223
<212> TYPE: PRT
<213> ORGANISM: Artificial Sequence
<220> FEATURE:
<223> OTHER INFORMATION: A109w/oW-VT Fc (CH3B included)

<400> SEQUENCE: 93

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Met Leu Thr Lys Asn Gln Val Trp Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 94
<211> LENGTH: 223
<212> TYPE: PRT
<213> ORGANISM: Artificial Sequence
<220> FEATURE:
<223> OTHER INFORMATION: A146w/oW-VT Fc (CH3A included)

<400> SEQUENCE: 94

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80
```

```
Val Leu Thr Val Leu His Gln Asp Trp Leu Asn Gly Lys Glu Tyr Lys
             85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Thr Cys Leu
130                 135                 140

Val Asp Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
            165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
            210                 215                 220

<210> SEQ ID NO 95
<211> LENGTH: 223
<212> TYPE: PRT
<213> ORGANISM: Artificial Sequence
<220> FEATURE:
<223> OTHER INFORMATION: A146w/oW-VT Fc (CH3B included)

<400> SEQUENCE: 95

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
        50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
             85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Met Leu Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
            165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
            210                 215                 220
```

<210> SEQ ID NO 96
<211> LENGTH: 223
<212> TYPE: PRT
<213> ORGANISM: Artificial Sequence
<220> FEATURE:
<223> OTHER INFORMATION: B168w/oW-VT Fc (CH3A included)

<400> SEQUENCE: 96

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Leu Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 97
<211> LENGTH: 223
<212> TYPE: PRT
<213> ORGANISM: Artificial Sequence
<220> FEATURE:
<223> OTHER INFORMATION: B168w/oW-VT Fc (CH3B included)

<400> SEQUENCE: 97

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95
```

```
Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Thr Cys Leu
            130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Gly Thr Thr Pro Pro Val Leu Asp Ser
                165                 170                 175

Asp Gly Ser Phe Phe Leu Tyr Ser Met Leu Thr Val Asp Lys Ser Arg
                180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
            210                 215                 220

<210> SEQ ID NO 98
<211> LENGTH: 223
<212> TYPE: PRT
<213> ORGANISM: Artificial Sequence
<220> FEATURE:
<223> OTHER INFORMATION: KiH (Genentech) Fc (CH3A included)

<400> SEQUENCE: 98

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Ser Cys Ala
            130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Val Ser Lys Leu Thr Val Asp Lys Ser Arg
                180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
            210                 215                 220

<210> SEQ ID NO 99
```

```
<211> LENGTH: 223
<212> TYPE: PRT
<213> ORGANISM: Artificial Sequence
<220> FEATURE:
<223> OTHER INFORMATION: KiH (Genentech) Fc (CH3B included)

<400> SEQUENCE: 99

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Trp Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 100
<211> LENGTH: 223
<212> TYPE: PRT
<213> ORGANISM: Artificial Sequence
<220> FEATURE:
<223> OTHER INFORMATION: Hole-Hole (Genentech) Fc (CH3A included)

<400> SEQUENCE: 100

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
```

```
            100                 105                 110
Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Ser Cys Ala
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Val Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 101
<211> LENGTH: 22
<212> TYPE: DNA
<213> ORGANISM: Artificial Sequence
<220> FEATURE:
<223> OTHER INFORMATION: Primer

<400> SEQUENCE: 101
gttccagact acgctctgca gg                                          22

<210> SEQ ID NO 102
<211> LENGTH: 20
<212> TYPE: DNA
<213> ORGANISM: Artificial Sequence
<220> FEATURE:
<223> OTHER INFORMATION: Primer

<400> SEQUENCE: 102
gaccaggcag gtcaggctga                                             20

<210> SEQ ID NO 103
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (22)..(22)
<223> OTHER INFORMATION: n is a, c, g, or t

<400> SEQUENCE: 103
tcagcctgac ctgcctggtc dnbggcttct atcccagcga catcg                 45

<210> SEQ ID NO 104
<211> LENGTH: 35
<212> TYPE: DNA
<213> ORGANISM: Artificial Sequence
<220> FEATURE:
<223> OTHER INFORMATION: Primer

<400> SEQUENCE: 104
tcgattttgt tacatctaca ctgttgttat cagat                            35

<210> SEQ ID NO 105
<211> LENGTH: 26
<212> TYPE: DNA
```

```
<213> ORGANISM: Artificial Sequence
<220> FEATURE:
<223> OTHER INFORMATION: Primer

<400> SEQUENCE: 105
ctcaaccggt tatttctact accgtc                                              26

<210> SEQ ID NO 106
<211> LENGTH: 18
<212> TYPE: DNA
<213> ORGANISM: Artificial Sequence
<220> FEATURE:
<223> OTHER INFORMATION: Primer

<400> SEQUENCE: 106
atcccgggat gggggcag                                                       18

<210> SEQ ID NO 107
<211> LENGTH: 63
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t

<400> SEQUENCE: 107
ctgcccccat cccgggatdn bctgaccaag aaccaggtcd nbctgacctg cctggtcaaa         60
ggc                                                                       63

<210> SEQ ID NO 108
<211> LENGTH: 33
<212> TYPE: DNA
<213> ORGANISM: Artificial Sequence
<220> FEATURE:
<223> OTHER INFORMATION: Primer

<400> SEQUENCE: 108
gaacaaagtc gattttgtta catctacact gtt                                      33

<210> SEQ ID NO 109
<211> LENGTH: 22
<212> TYPE: DNA
<213> ORGANISM: Artificial Sequence
<220> FEATURE:
<223> OTHER INFORMATION: Primer

<400> SEQUENCE: 109
gttccagact acgctctgca gg                                                  22

<210> SEQ ID NO 110
<211> LENGTH: 18
<212> TYPE: DNA
<213> ORGANISM: Artificial Sequence
<220> FEATURE:
<223> OTHER INFORMATION: Primer

<400> SEQUENCE: 110
cagcacggga ggcgtggt                                                       18
```

```
<210> SEQ ID NO 111
<211> LENGTH: 42
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (20)..(20)
<223> OTHER INFORMATION: n is a, c, g, or t

<400> SEQUENCE: 111
accacgcctc ccgtgctgdn btccgacggc tccttcttcc tc                              42

<210> SEQ ID NO 112
<211> LENGTH: 35
<212> TYPE: DNA
<213> ORGANISM: Artificial Sequence
<220> FEATURE:
<223> OTHER INFORMATION: Primer

<400> SEQUENCE: 112
tcgattttgt tacatctaca ctgttgttat cagat                                     35

<210> SEQ ID NO 113
<211> LENGTH: 26
<212> TYPE: DNA
<213> ORGANISM: Artificial Sequence
<220> FEATURE:
<223> OTHER INFORMATION: Primer

<400> SEQUENCE: 113
ctcaaccggt tatttctact accgtc                                               26

<210> SEQ ID NO 114
<211> LENGTH: 58
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (36)..(36)
<223> OTHER INFORMATION: n is a, c, g, or t

<400> SEQUENCE: 114
aggagccgtc ggacaccagc acgggaggcg tggtvnhgta gttgttctcc ggctgccc            58

<210> SEQ ID NO 115
<211> LENGTH: 57
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (35)..(35)
<223> OTHER INFORMATION: n is a, c, g, or t

<400> SEQUENCE: 115
ctggtgtccg acggctcctt caccctctac agcdnbctca ccgtggacaa gagcagg             57

<210> SEQ ID NO 116
<211> LENGTH: 33
<212> TYPE: DNA
<213> ORGANISM: Artificial Sequence
<220> FEATURE:
<223> OTHER INFORMATION: Primer
```

<400> SEQUENCE: 116
gaacaaagtc gattttgtta catctacact gtt                33

<210> SEQ ID NO 117
<211> LENGTH: 22
<212> TYPE: DNA
<213> ORGANISM: Artificial Sequence
<220> FEATURE:
<223> OTHER INFORMATION: Primer

<400> SEQUENCE: 117
gttccagact acgctctgca gg                22

<210> SEQ ID NO 118
<211> LENGTH: 18
<212> TYPE: DNA
<213> ORGANISM: Artificial Sequence
<220> FEATURE:
<223> OTHER INFORMATION: Primer

<400> SEQUENCE: 118
atcccgggat gggggcag                18

<210> SEQ ID NO 119
<211> LENGTH: 63
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 119
ctgcccccat cccgggatnn kctgaccaag aaccaggtcn nkctgacctg cctggtcgag     60
ggc                63

<210> SEQ ID NO 120
<211> LENGTH: 35
<212> TYPE: DNA
<213> ORGANISM: Artificial Sequence
<220> FEATURE:
<223> OTHER INFORMATION: Primer

<400> SEQUENCE: 120
tcgattttgt tacatctaca ctgttgttat cagat                35

<210> SEQ ID NO 121
<211> LENGTH: 26
<212> TYPE: DNA
<213> ORGANISM: Artificial Sequence
<220> FEATURE:
<223> OTHER INFORMATION: Primer

<400> SEQUENCE: 121
ctcaaccggt tatttctact accgtc                26

<210> SEQ ID NO 122
<211> LENGTH: 20
<212> TYPE: DNA
<213> ORGANISM: Artificial Sequence

```
<220> FEATURE:
<223> OTHER INFORMATION: Primer

<400> SEQUENCE: 122
gaccaggcag gtcaggctga                                                    20

<210> SEQ ID NO 123
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (21)..(22)
<223> OTHER INFORMATION: n is a, c, g, or t

<400> SEQUENCE: 123
tcagcctgac ctgcctggtc nnkggcttct atcccagcga catcg                        45

<210> SEQ ID NO 124
<211> LENGTH: 33
<212> TYPE: DNA
<213> ORGANISM: Artificial Sequence
<220> FEATURE:
<223> OTHER INFORMATION: Primer

<400> SEQUENCE: 124
gaacaaagtc gattttgtta catctacact gtt                                     33

<210> SEQ ID NO 125
<211> LENGTH: 22
<212> TYPE: DNA
<213> ORGANISM: Artificial Sequence
<220> FEATURE:
<223> OTHER INFORMATION: Primer

<400> SEQUENCE: 125
gttccagact acgctctgca gg                                                 22

<210> SEQ ID NO 126
<211> LENGTH: 58
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (36)..(37)
<223> OTHER INFORMATION: n is a, c, g, or t

<400> SEQUENCE: 126
aggagccgtc ggacaacagc acgggaggcg tggtmnngta gttgttctcc ggctgccc          58

<210> SEQ ID NO 127
<211> LENGTH: 57
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (34)..(35)
<223> OTHER INFORMATION: n is a, c, g, or t

<400> SEQUENCE: 127
ctgttgtccg acggctcctt cttcctctac agcnnkctca ccgtggacaa gagcagg           57
```

```
<210> SEQ ID NO 128
<211> LENGTH: 35
<212> TYPE: DNA
<213> ORGANISM: Artificial Sequence
<220> FEATURE:
<223> OTHER INFORMATION: Primer

<400> SEQUENCE: 128
tcgattttgt tacatctaca ctgttgttat cagat                              35

<210> SEQ ID NO 129
<211> LENGTH: 26
<212> TYPE: DNA
<213> ORGANISM: Artificial Sequence
<220> FEATURE:
<223> OTHER INFORMATION: Primer

<400> SEQUENCE: 129
ctcaaccggt tatttctact accgtc                                         26

<210> SEQ ID NO 130
<211> LENGTH: 18
<212> TYPE: DNA
<213> ORGANISM: Artificial Sequence
<220> FEATURE:
<223> OTHER INFORMATION: Primer

<400> SEQUENCE: 130
cagcacggga ggcgtggt                                                  18

<210> SEQ ID NO 131
<211> LENGTH: 42
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (19)..(20)
<223> OTHER INFORMATION: n is a, c, g, or t

<400> SEQUENCE: 131
accacgcctc ccgtgctgnn ktccgacggc tccttcttcc tc                       42

<210> SEQ ID NO 132
<211> LENGTH: 33
<212> TYPE: DNA
<213> ORGANISM: Artificial Sequence
<220> FEATURE:
<223> OTHER INFORMATION: Primer

<400> SEQUENCE: 132
gaacaaagtc gattttgtta catctacact gtt                                 33
```

METHOD FOR PRODUCING ANTIBODY CH3 DOMAIN HETERODIMERIC MUTANT PAIR USING YEAST MATING AND CH3 MUTANT PAIR PRODUCED THEREBY

CROSS REFERENCE TO RELATED APPLICATIONS

This application is a National Stage of International Application No. PCT/KR2016/011396 filed Oct. 12, 2016, claiming priority based on Korean Patent Application No. 10-2015-0142181 filed Oct. 12, 2015.

TECHNICAL FIELD

The present disclosure relates to a method for evaluating a formation of a heterodimer of an antibody CH3 domain using yeast surface display and yeast mating, and a method for producing a heterodimeric heavy chain constant region (heterodimeric Fc) library of a human antibody (immunoglobulin G, IgG) using the same.

Further, the present disclosure also relates to a library and a method for screening a CH3 domain mutant pair in which a formation of a heterodimeric heavy chain constant region is preferred through the library.

In addition, the present disclosure relates to a CH3 domain mutant pair in which formation of a heterodimeric heavy chain constant region is preferred, a heterodimeric heavy chain constant region pair comprising the CH3 mutant pair, a bispecific antibody, and a fusion protein.

The present disclosure also relates to a pharmaceutical composition including the heterodimer, a heterodimeric heavy chain constant region pair comprising the same, a bispecific antibody, and a fusion protein.

BACKGROUND ART

After the facts that diphtheria and tetanus are prevented by administering non-lethal doses of serum from experimental animals into which diphtheria and tetanus are administered to other animals were discovered at the end of the 19th century, concept of serum treatment, that is, antibody treatment, gradually began to be used in clinical practice. However, early antibody treatment has very limited practicality due to problems such as contamination, etc., of high-purity antibodies and blood-borne infectious agents. The problem with this traditional antibody treatment has come to a new turning point since a hybridoma fusion technique developed in 1975 enables mass production of a pure form of a rodent-derived monoclonal antibody at relatively low cost.

However, the use of the traditional antibody treatment in clinical practice has been limited due to various disadvantages and side effects such as short half-life caused when a mouse-derived monoclonal antibody is administered to human, an immune response to anti-mouse antibody, reduction in efficacy, and fatal allergic response, etc.

In the 1980s, the emergence of gene recombination technique, which was a starting point of bio-revolution, enabled production of a humanized antibody that humanized a mouse monoclonal antibody through gene manipulation, and minimization of various immunological side effects that occurred at the time of administration to a patient, and thus there was provided a basis for a therapeutic antibody to be positively utilized in clinical practice. Meanwhile, since the mid-1990s, a phage display technique or a source technique capable of producing a fully human monoclonal antibody using a transgenic mouse has been developed. Currently, many pharmaceutical companies in Korea and abroad are vigorously researching and investing in the development of new drugs using antibodies. Currently, about 40 antibody drugs are marketed globally with approval of the US Food and Drug Administration, and more than 300 therapeutic antibodies demonstrate importance of antibodies in the pharmaceutical industry in clinical trials. Meanwhile, in recent years, preclinical and clinical trial results that combination treatment of an antibody having target selectivity and a chemotherapeutic agent having no target specificity has resulted in inhibition of side effects and improvement of therapeutic effects, have been derived, and thus usefulness of the antibodies in anti-cancer treatment will be further expanded.

Meanwhile, currently new antibody drugs have been developed for cancer, autoimmune diseases, etc., as main targets. In particular, in the case of a solid tumor, IgG or a pure antibody-type new antibody drug does not show a satisfactory therapeutic effect, and high cost of antibody production, etc., are obstacles to developing the new antibody drug. Thus, development of a new antibody drug in the form of recombinant protein having improved biological efficacy over existing antibodies, has been steadily attempted. One of the attempts may be particularly a bispecific antibody in which one antibody is able to bind to at least two target molecules, which has started in the mid-1980s to be utilized for cancer treatment.

Antibodies (immunoglobulin G (IgG), IgM, IgD, IgE, and IgA) present in nature are present in a form in which two light chains having the same amino acid sequence are assembled with two heavy chains having the same amino acid sequence. Here, formation of a homodimer between two identical heavy chains is induced through non-covalent interaction between last domains of a constant region (Fc, crystallizable fragment) of an antibody (i.e., a CH3 domain for IgG, a CH4 domain for IgM, a CH3 domain for IgD, CH2 and CH4 domains for IgE, and a CH3 domain for IgA), and then a disulfide bond between hinge regions is induced to form the homodimer between the rigid heavy chains. Specifically, the assembly of the heavy chains and the light chains in human IgG1 is induced by the disulfide bond between 5th Cys in a heavy chain hinge region and 107th Cys in a kappa light chain. The number of amino acids in the antibody chain is based on EU numbering (Cunningham, Pflumm et al., 1969).

Here, the term "non-covalent interaction" refers to an interaction having weak binding force when an atom or a molecule forms an aggregate by an interaction other than a covalent bond, and includes electrostatic interaction, hydrophobic interaction, hydrogen bonding interaction, cation-n interaction, and Van Der Waals interaction. In addition, the term "electrostatic interaction" refers to a bond that depends on electrical attraction between ions having opposite charges, the term "hydrophobic interaction" refers to a bond according to tendency of hydrophobic molecules to stabilize thermodynamically while avoiding interaction with polar solvents, the term "hydrogen bonding" refers to an interaction between dipoles generated between polar covalent bond molecules formed by hydrogen with fluorine, oxygen or nitrogen, and the term "cation-n interaction" refers to an interaction between a molecule having a positive charge and a molecule including an electron-rich aromatic ring. In addition, the term "Van Der Waals interaction" refers to a bond formed by an action of attraction and repulsion between mutually polarized molecules due to Van Der Waals force. In addition, the term "homodimer" refers to a dimer of an antibody domain having the same amino acid sequence or a part or all of an antibody including the same, and specifically, refers to a dimer between CH3 domains of a heavy chain constant region of a human antibody or an antibody heavy chain constant region dimer including the same CH3 domain.

Therefore, a monoclonal antibody (mAb) present in nature has a property of binding in a bivalent form to one kind of antigen. The bispecific antibody, on the other hand, refers to an antibody having one monomolecular form, and being capable of simultaneously or alternatively binding two antigens. The bispecific antibody is known in the art as engineered protein such as a bispecific antibody or a multispecific antibody capable of binding to two or more antigens, and may be produced by using cell fusion, chemical conjugation, recombinant DNA techniques.

Conventional bispecific antibodies are produced by a quadroma technique using somatic fusion of two different hybridoma cell lines expressing a murine monoclonal antibody having desired specificity (Milstein and Cuello, 1983). However, in this technique, two different light chains are randomly paired in a quadratic cell line to produce various antibodies up to about 10, and thus there is disadvantage that it is very difficult to separate and purify only one desired bispecific antibody from the antibody mixture. Therefore, in order to obtain only the desired bispecific antibody due to by-products forming wrong pairs and a reduced production yield, complicated purification processes are required (Morrison et al., 2007).

As one solution to solve this problem, a bispecific antibody in which a light chain antigen-binding region fragment and a heavy chain antigen-binding region fragment are linked by various chains and expressed as single constructs was developed, which includes forms such as a single chain diabody, tandem single chain antibody fragment (scFv), etc. (Holliger and Hudson, 2005). In addition, a bispecific antibody in a form similar to Ig fused with an additional antigen-binding antibody fragment at the N-terminus or C-terminus of the heavy or light chain of the antibody was also produced (Miller, Meng et al., 2003; Lu, Zhang et al., 2004).

However, the bispecific antibody based on this antibody fragment combination has problems of reduction in expression amount due to low stability, aggregation of antibody, and thus increased immunogenicity (Chan and Carter, 2010). Further, the bispecific antibody based only on the antibody fragment combination lacks the antibody's heavy chain constant region (Fc), which causes problems in that there are no increased stability, increased size, a long serum half-life due to binding to a Fc receptor (neonatal Fc receptor, FcRn), advantages of conservation of binding regions (protein A and protein G) in the purification process, antibody-dependent cellular cytotoxicity, and complement-dependent cellular cytotoxicity associated with the heavy chain constant region (Chan and Carter, 2010).

Therefore, it is ideally required to develop a bispecific antibody having a structure very similar to a naturally occurring antibody (IgG, IgM, IgA, IgD, or IgE) and having a minimal deviation in sequence.

To solve this problem, development of a bispecific antibody using a heterodimeric heavy chain constant region has been attempted. This technique induces mutations in a CH3 domain of two different antibody heavy chains by genetic manipulation, resulting in induction of the two heavy chains to form the heterodimer (U.S. Pat. No. 7,695,936 B2; Korean Patent No. 10-1522954).

In the case of a wild-type IgG antibody, the homodimer of the CH3 domain is known to be formed by residues (L351, T366, L368, Y407) that induce hydrophobic interaction located in the center of a CH3 domain interaction surface (hydrophobic core) and residues (E357, K370, K392, D399, K409) that induce symmetric electrostatic interaction around the residues (Gunasekaran et al., 2010; Choi et al., 2013).

Thus, most of CH3 domain mutants that have been known to induce heterodimer formation have been produced by introducing an asymmetric mutant pair based on structure-based rational design of the antibody into the CH3 domain interaction surface (Spreter Von Kreudenstein et al., 2014).

One of the methods is to use a knob-into-hole technique. In the knob-into-hole technique, with respect to residues located in the hydrophobic core of the CH3 domain interacting surface, when hydrophobic amino acid residues having a large sized side chain are substituted with hydrophobic amino acids having a small side chain to make a hole structure on one-side CH3 domain (T366S, L368A, Y407V), and hydrophobic amino acid residues having a small sized side chain are substituted with a hydrophobic amino acid having a large sized side chain to make a knob structure on the other CH3 domain (T366W), and then a heavy chain constant region into which a mutant pair is introduced is co-expressed, space-complementary hydrophobic bonding is formed to prefer the heterodimer formation (Ridgway et al., 1996). HA-TF (Moore G L et al., 2011), ZW1 (Von Kreudenstein et al., 2013), and SEEDBody (Davis J H et al., 2010) have been reported as CH3 domain mutants produced using a strategy similar thereto.

Another method for promoting the formation of heterodimer is to induce a mutation in the charged amino acids present on the CH3 domain interaction surface, wherein specifically, a mutant is induced with a positively charged side chain amino acid on one side CH3 domain, and with a negatively charged side chain amino acid on the other side CH3 domain, and thus formation of the homodimer may be inhibited by electrostatic repulsion and formation of the heterodimer may be promoted by electrostatic attraction. DD-KK (Gunasekaran et al., 2010) and EEE-RRR (Strop P et al., 2012) have been reported as CH3 domain mutants produced using this strategy.

Still another method for promoting the formation of heterodimer is to preserve the hydrophobic core of the CH3 domain interaction surface and to induce mutation in the charged amino acid, thereby forming a space-complementary hydrophobic interaction ($K409W_{CH3A}$-$D399V$/$F405T_{CH3B}$), and forming an additional long-distance electrostatic interaction ($K360E_{CH3A}$-$Q347R_{CH3B}$) at the edge of the CH3 domain interaction surface (Choi et al., 2013; Korean Patent No. 10-1522954).

However, the thermodynamic stability and expression yield of the heterodimeric heavy chain constant region including the CH3 domain mutant pair developed above are lower than those of the wild type antibody.

Therefore, there is a need for development of the heterodimeric heavy chain constant region that exhibits a heterodimer formation yield as high as possible and has similar or improved thermodynamic stability and expression yield as compared to those of the wild type antibody. However, so far, no reports have been made to satisfy this need.

In addition, since as a strategy for promoting the heterodimer formation up to now, a space-complementary hydrophobic bond or an electrostatic bond was introduced into the CH3 domain interaction surface by using the structure-based rational design of antibody, there is a need for development of the CH3 domain mutant having a new class of non-covalent bonding.

Therefore, the present inventor created a system for evaluating a formation ability of a heterodimeric heavy chain constant region using a yeast cell surface expression system, constructed a human antibody heterodimeric heavy chain constant region library by using the system, and selected a CH3 domain mutant having high formation ability of the heterodimer through high speed selection. In addition, the present inventor found that in the selected CH3 domain mutants, the formation of heterodimer was preferred by a new kind of non-covalent bonding such as hydrogen bonding and cation-n bonding, and completed the present disclosure.

(Non-Patent Document 1) Atwell, S., J. B. Ridgway, et al. (1997). "Stable Heterodimers from Remodeling the Domain Interface of a Homodimer Using a Phage Display Library." J Mol Biol 270(1): 26-35.

(Non-Patent Document 2) Baek et al. (2014) "Construction of a Large Synthetic Human Fab Antibody Library on Yeast Cell Surface by Optimized Yeast Mating." J Microbiol. Biotechnol. 24:408-420.

(Non-Patent Document 3) Chan, A. C. and P. J. Carter (2010). "Therapeutic Antibodies for Autoimmunity and Inflammation." Nat. Rev. Immunol. 10(5): 301-316.

(Non-Patent Document 4) Choi et al. (2013) "A Heterodimeric Fc-Based Bispecific Antibody Simultaneously Targeting VEGFR-2 and Met Exhibits Potent Anti-Tumor Activity." Mol. Cancer Ther. 12:2748-2759.

(Non-Patent Document 5) Choi et al. (2015) "Crystal Structures of Immunoglobulin Fc Heterodimers Reveal the Molecular Basis for Heterodimer Formation." Mol Immunol 65:377-383.

(Non-Patent Document 6) Cunningham, B. A., M. N. Pflumm, et al. (1969). "Subgroups of Amino Acid Sequences in the Variable Regions of Immunoglobulin Heavy Chains." Proc. Natl. Acad. Sci. USA 64(3): 997-1003.

(Non-Patent Document 7) Davis, J. H., C. Aperlo, et al. (2010). "SEEDbodies: Fusion Proteins Based on Strand-Exchange Engineered Domain (SEED) CH3 Heterodimers in an Fc Analogue Platform for Asymmetric Binders or Immunofusions and Bispecific Antibodies." Protein Eng. Des. Sel. 23(4): 195-202.

(Non-Patent Document 8) Feng Y. et al. (2011). "Design, Expression and Characterization of a Soluble Single-Chain Functional Human Neonatal Fc Receptor." Protein Expression and Purification 79(1):66-71.

(Non-Patent Document 9) Gunasekaran, K., M. Pentony, et al. (2010). "Enhancing Antibody Fc Heterodimer Formation Through Electrostatic Steering Effects: Applications to Bispecific Molecules and Monovalent IgG." J. Biol. Chem. 285(25): 19637-19646.

(Non-Patent Document 10) Holliger, P. and P. J. Hudson (2005). "Engineered antibody fragments and the rise of single domains." Nat. Biotechnol. 23(9): 1126-1136.

(Non-Patent Document 11) Kim et al. (2007). "Comparative Analyses of Complex Formation and Binding Sites Between Human Tumor Necrosis Factor-Alpha and Its Three Antagonists Elucidate Their Different Neutralizing Mechanisms." J Mol Biol 374:1374-88

(Non-Patent Document 12) Lu, D., H. Zhang, et al. (2004). "Simultaneous Blockade of Both the Epidermal Growth Factor Receptor and the Insulin-Like Growth Factor Receptor Signaling Pathways in Cancer Cells with a Fully Human Recombinant Bispecific Antibody." J Biol Chem 279(4): 2856-2865.

(Non-Patent Document 13) Miller, K., G. Meng, et al. (2003). "Design, Construction, and in Vitro Analyses of Multivalent Antibodies." J. Immunol. 170(9): 4854-4861.

(Non-Patent Document 14) Milstein, Cuello et al. (1983). "Hybrid Hybridomas and Their Use in Immunohistochemistry." Nature 305:537-540.

(Non-Patent Document 15) Moore, G. L., C. Bautista, et al. (2011). "A Novel Bispecific Antibody Format Enables Simultaneous Bivalent and Monovalent Co-Engagement of Distinct Target Antigens." MAbs 3(6): 546-557.

(Non-Patent Document 16) Ridgway, J. B., L. G. Presta, et al. (1996). "'Knobs-Into-Holes' Engineering of Antibody CH3 Domains for Heavy Chain Heterodimerization." Protein Eng. 9(7): 617-621.

(Non-Patent Document 17) Strop, P et al. (2012) "Generating Bispecific Human Igg1 and Igg2 Antibodies from Any Antibody Pair." J Mol Biol 420:204-219.

(Non-Patent Document 18) Spreter Von Kreudenstein et al. (2014) "Protein Engineering and the Use of Molecular Modeling and Simulation: The Case of Heterodimeric Fc Engineering." Methods 65:77-94.

(Non-Patent Document 19) Von Kreudenstein et al. (2013) "Improving Biophysical Properties of a Bispecific Antibody Scaffold to Aid Developability: Quality by Molecular Design." mAbs 5:646-654.

SUMMARY

The present disclosure has been made to develop a technique for stably enhancing a formation yield of a heterodimeric heavy chain constant region of a human antibody to 90% or more as described above. An object of the present disclosure is to provide a heterodimeric heavy chain constant region library and a method for evaluating heterodimer formation of an antibody CH3 domain through yeast mating.

Another object of the present disclosure is to provide a method for producing a CH3 domain mutant pair in which formation of a heterodimeric heavy chain constant region is preferred (heterodimeric CH3).

Still another object of the present disclosure is to provide a CH3 domain mutant pair in which a heterodimer formation yield is enhanced, selected through a heterodimeric heavy chain constant region library by the above evaluation method.

Still another object of the present disclosure is to provide a bispecific antibody or an antibody constant region fusion protein that shows expression, a production yield, and thermodynamic stability that are similar to or improved as compared to those of the original wild-type antibody by expressing and producing a protein including the heterodimeric heavy chain constant region pair in a cell.

In addition, still another aspect of the present disclosure is to provide an antibody or an antibody constant region fusion protein in which an intrinsic function of a heavy chain constant region possessed by the wild type antibody, i.e., a binding ability to FcRn (neonatal Fc receptor) is maintained to have a long serum half-life in blood, to maintain an effector function, and to conserve binding sites (protein A and protein G) in a purification process by expressing and producing a protein including the heterodimeric heavy chain constant region pair in a cell.

In order to achieve the foregoing objects, the present disclosure provides method for evaluating a formation of a heterodimer of an antibody CH3 domain including:

(1) preparing a yeast cell surface expression vector comprising a first CH3 domain and a yeast extracellular secretion vector comprising a second CH3 domain;

(2) transfecting yeasts having different mating types with the vector of step (1), respectively, to obtain transfected yeasts;

(3) mating the two transfected yeasts with different mating type obtained in the step (2); and (4) detecting a second CH3 domain cloned in the yeast extracellular secretion vector on a surface of the mated yeast of step (3).

DESCRIPTION OF DRAWINGS

FIG. 1 is a schematic diagram showing a strategy for expressing a human antibody heterodimeric heavy chain constant region on a surface of a yeast cell using yeast mating.

FIG. 2 is a schematic diagram showing a yeast cell surface expression vector used in a yeast cell surface expression system of the heterodimeric heavy chain constant region.

FIG. 3 is a schematic diagram showing a yeast extracellular cell secretion vector used in the yeast cell surface expression system of the heterodimeric heavy chain constant region.

FIG. 4A is a histogram showing a PE signal value obtained by detecting secreted $Fc_{CH3B}$ immobilized on a surface of a diploid yeast cell expressing a CH3 domain mutant pair having different formation yields of the heterodimeric heavy chain constant region, and FIG. 4B shows data obtained by comparing mean fluorescence intensity at a positive peak of the histogram with a PE signal value of EW-RVT CH3 domain mutant pair and performing quantification (normalization of the mean fluorescence sensitivity of EW-RVT to 100%).

FIG. 5 is a schematic diagram showing a library construction strategy for obtaining a CH3 domain mutant pair having a high heterodimer formation yield by introducing a mutation into a CH3 domain interaction surface.

FIG. 6A shows data obtained by comparison between mean fluorescence intensity measured from a PE signal value obtained by detecting secreted $Fc_{CH3B}$ immobilized on a surface of the yeast cell after suspending LibA1 and LibB1 libraries, and a PE signal value of the EW-RVT CH3 domain mutant pair (normalization of the mean fluorescence sensitivity of EW-RVT to 100%).

FIG. 6B shows data obtained by comparison between mean fluorescence intensity measured from a PE signal value obtained by detecting secreted $Fc_{CH3B}$ of four individual clones (A107, A108, A109, and A146) selected from the LibA1 library and three individual clones (B121, B135, and B168) selected from the LibB1 library, and a PE signal value of the EW-RVT CH3 domain mutant pair (normalization of the mean fluorescence sensitivity of EW-RVT to 100%).

FIG. 7 is a schematic diagram showing a scFv-$Fc_{CH3A}$/$Fc_{CH3B}$ co-expression system.

FIG. 8 shows data obtained by purifying scFv-$Fc_{CH3A}$/$Fc_{CH3B}$ heterodimer protein including four individual clones (A107, A108, A109, and A146) selected from the LibA1 library and three individual clones (B121, B135, and B168) selected from the LibB1 library, and analyzing 5 µg of the protein on SDS-PAGE under 12% non-reducing conditions.

FIG. 9 shows data obtained by purifying scFv-$Fc_{CH3A}$/$Fc_{CH3B}$ heterodimer protein in which molar ratios of pcDNA3.1(+)-scFv-$Fc_{CH3A}$ and pcDNA3.1 (+)-$Fc_{CH3B}$ plasmids added at transfection for the A107 and B168 mutant pairs are different, and analyzing the protein on SDS-PAGE under non-reducing conditions.

FIG. 10 shows data obtained by purifying scFv-$Fc_{CH3A}$/$Fc_{CH3B}$ heterodimer protein including four kinds of mutant pairs ($A107_{w/oW-VT}$, $A109_{w/oW-VT}$, $A146_{w/oW-VT}$, and $B168_{w/oW-VT}$) in which the W-VT mutation site is substituted with a wild-type amino acid and control groups W-VT and EW-RVT, and analyzing 5 µg of the protein on SDS-PAGE under 12% non-reducing conditions.

FIG. 11 shows quantitative data showing a heterodimer formation yield obtained by repeatedly expressing and purifying the scFv-$Fc_{CH3A}$/$Fc_{CH3B}$ heterodimer described in FIG. 8 and FIG. 10, and analyzing each band density on the SDS-PAGE.

FIG. 12A shows the CH3 domain interaction surface of the mutant including the A107 mutant pair which is predicted through modeling. K370E and K409W mutants were introduced into one CH3 domain and E357N, D399V and F405T mutants were introduced into the other CH3 domain.

FIG. 12B shows the CH3 domain interaction surface of the mutant including the A108 mutant pair which is predicted through modeling. K370E and K409W mutants were introduced into one CH3 domain and E357I, S364T, D399V, and F405T mutants were introduced into the other CH3 domain.

FIG. 13A shows the CH3 domain interaction surface of the mutant including the A109 mutant pair which is predicted through modeling. K370M and K409W mutants were introduced into one CH3 domain and E357M, S364W, D399V, and F405T mutants were introduced into the other CH3 domain.

FIG. 13B shows the CH3 domain interaction surface of the mutant including the A146 mutant pair which is predicted through modeling. K370D and K409W mutants were introduced into one CH3 domain and E357M, D399V, and F405T mutants were introduced into the other CH3 domain.

FIG. 14A shows the CH3 domain interaction surface of the mutant including the B121 mutant pair which is predicted through modeling. D399E, and K409W mutants were introduced into one CH3 domain and K392E, D399V, and F405T mutants were introduced into the other CH3 domain.

FIG. 14B shows the CH3 domain interaction surface of the mutant including the B135 mutant pair which is predicted through modeling. D399L and K409W mutants were introduced into one CH3 domain and K392S, K409L, D399V, and F405T mutants were introduced into the other CH3 domain.

FIG. 15 shows the CH3 domain interaction surface of the mutant including the B168 mutant pair which is predicted through modeling. D399L and K409W mutants were introduced into one CH3 domain and K392G, K409M, D399V, and F405T mutants were introduced into the other CH3 domain.

FIG. 16 is a schematic diagram showing LibA2 library and LibB2 library construction strategy based on $A107_{w/oW-VT}$ and $B168_{w/oW-VT}$ mutant pairs.

FIG. 17A shows data obtained by comparison between mean fluorescence intensity measured from a PE signal value obtained by detecting secreted $Fc_{CH3B}$ immobilized on a surface of the yeast cell after suspending LibA2 and LibB2 libraries, and a PE signal value of the EW-RVT CH3 domain mutant pair (normalization of the mean fluorescence sensitivity of EW-RVT to 100%).

FIG. 17B shows data obtained by comparison between mean fluorescence intensity of a PE signal value obtained by detecting secreted $Fc_{CH3B}$ of four individual clones (A205, A210, A216, and A241) selected from the LibA2 library and six individual clones (B212, B215, B235, B239, B240, and B256) selected from the LibB2 library, and a PE signal value of the EW-RVT CH3 domain mutant pair (normalization of the mean fluorescence sensitivity of EW-RVT to 100%).

FIG. 18A shows data obtained by purifying scFv-$Fc_{CH3A}$/$Fc_{CH3B}$ heterodimer protein including 10 mutant pairs selected from the LibA2 library and the LibB2 library and control groups (EW-RVT, $A107_{w/oW-VT}$, A107, $B168_{w/oW-VT}$, and B168), and analyzing 5 µg of the protein on SDS-PAGE under 12% non-reducing conditions.

FIG. 18B shows quantitative data showing the heterodimer formation yield obtained by repeatedly expressing and purifying the scFv-$Fc_{CH3A}$/$Fc_{CH3B}$ heterodimer described in FIG. 18A, and analyzing each band density on the SDS-PAGE.

FIG. 19 shows data obtained by purifying scFv-$Fc_{CH3A}$/$Fc_{CH3B}$ heterodimer protein in which molar ratios of pcDNA3.1(+)-scFv-$Fc_{CH3A}$ and pcDNA3.1(+)-$Fc_{CH3B}$ plasmids added at transfection for the A205 and B235 variant pairs are different, and analyzing the protein on SDS-PAGE under non-reducing conditions.

FIG. 20A shows the CH3 domain interaction surface of the mutant including the A205 variant pair which is predicted through modeling. E357D, S364W, and K370E mutants were introduced into one CH3 domain and E357N and K370R mutants were introduced into the other CH3 domain.

FIG. 20B shows the CH3 domain interaction surface of the mutant including the A210 mutant pair which is predicted through modeling. E357A, S364Y, and K370E mutants were introduced into one CH3 domain and E357N and K370H mutants were introduced into the other CH3 domain.

FIG. 21A shows the CH3 domain interaction surface of the mutant including the A216 mutant pair which is predicted through modeling. E357G, S364W, and K370E mutants were introduced into one CH3 domain and E357N mutant were introduced into the other CH3 domain.

FIG. 21B shows the CH3 domain interaction surface of the mutant including the A241 mutant pair which is predicted through modeling. E357N, S364W, and K370E mutants were introduced into one CH3 domain and E357N mutant were introduced into the other CH3 domain.

FIG. 22A shows the CH3 domain interaction surface of the mutant including the B212 mutant pair which is predicted through modeling. K392I and D399L mutants were introduced into one CH3 domain and D399G, K392G, and K409M mutants were introduced into the other CH3 domain.

FIG. 22B shows the CH3 domain interaction surface of the mutant including the B215 mutant pair which is predicted through modeling. K392R, K409R, and D399L mutants were introduced into one CH3 domain and D399W, K392G, and K409M mutants were introduced into the other CH3 domain.

FIG. 23A shows the CH3 domain interaction surface of the mutant including the B235 variant pair which is predicted through modeling. K392C, and D399L mutants were introduced into one CH3 domain and D399C, K392G, and K409M mutants were introduced into the other CH3 domain.

FIG. 23B shows the CH3 domain interaction surface of the mutant including the B239 mutant pair which is predicted through modeling. K392L, and D399L mutants were introduced into one CH3 domain and D399S, K392G, and K409M mutants were introduced into the other CH3 domain.

FIG. 24A shows the CH3 domain interaction surface of the mutant including the B240 mutant pair which is predicted through modeling. K392S, K409R, and D399L mutants were introduced into one CH3 domain and D399G, K392G, and K409M mutants were introduced into the other CH3 domain.

FIG. 24B shows the CH3 domain interaction surface of the mutant including the B256 mutant pair which is predicted through modeling. K392N, and D399L mutants were introduced into one CH3 domain and D399V, K392G, and K409M mutants were introduced into the other CH3 domain.

FIG. 25 shows data obtained by modeling the heavy chain constant region dimer, $Fc_{CH3A}$-$Fc_{CH3B}$ used for evaluation of thermal stability and evaluation of FcRn binding capacity.

FIG. 26 shows data obtained by producing heavy chain constant region dimers (Fc-A107, Fc-B168, Fc-A205, and Fc-B235) including a wild type heavy chain constant region and a mutant pair selected from the library, respectively, and analyzing the dimers on SDS-PAGE under 12% non-reducing conditions and reducing conditions.

FIG. 27 shows results of HPLC analysis of the heavy chain constant region mutant produced in FIG. 26 using a size exclusion chromatography column.

FIG. 28 shows differential scanning calorimetry analysis result of the wild-type heavy chain constant region and the heavy chain constant region mutant produced in FIG. 26 and the maximum heat capacity temperature of the CH2 domain and the CH3 domain.

FIG. 29 shows results of analysis of the binding ability of wild-type heavy chain constant region and heavy chain constant region mutant produced in FIG. 26 to FcRn using SPR.

BEST MODE

Hereinafter, the present disclosure will be described in detail.

As used herein, the term "heterodimer" refers to a dimer consisting of two antibody domains having different amino acid sequences or a part or all of an antibody including the same, and specifically, a dimer consisting of a dimer of a CH3 domain pair having different sequences of a heavy chain constant region of a human antibody or a part or all of an antibody including a CH3 domain pair having different sequences.

In addition, the term "heterodimeric heavy chain constant region (heterodimeric Fc)" refers to a dimer between heavy chain constant regions (hinge-CH2-CH3) including CH3A and CH3B having different amino acid sequences, respectively.

Further, the term "heterodimeric heavy chain constant region formation yield" refers to a ratio of a heavy chain constant region formed by a heterodimer in the sum of an entire heavy chain constant region dimer (homodimer, heterodimer) or a monomer when a heavy chain constant region pair including a CH3 domain mutant pair is simultaneously transformed into HEK293F animal cells and expressed and purified, as a percentage.

In an embodiment of the present disclosure, the present inventor made a great effort to enhance a formation yield of a heterodimeric heavy chain constant region between a pair of heavy chain constant regions in which a CH3 mutant pair is fused to C-terminus of the hinge-CH2, i.e., between hinge-CH2-CH3A and hinge-CH2-CH3B by modifying an amino acid residue contributing to an interaction between CH3 domains, thereby inducing formation of a pair in which a first CH3 domain (CH3A) and a second CH3 domain (CH3B) is capable of interacting selectively to each other through noncovalent bonds (CH3A:CH3B), from which confirmed that the amino acid substitution at a specific position on each CH3 domain promoted the formation yield of the heterodimeric heavy chain constant region.

Specifically, in an embodiment of the present disclosure, a system for quantitatively evaluating the heterodimer formation yield was constructed in order to select the CH3 domain mutant pair forming the heterodimer at a high yield by using directed evolution.

In an embodiment of the present disclosure, a human antibody heterodimeric heavy chain constant region was expressed on a surface of a yeast cell using yeast mating, and a heavy chain (displayed $Fc_{CH3A}$) including the CH3A domain was constructed in a yeast cell surface expression vector, and a heavy chain (secreted $Fc_{CH3B}$) including the CH3B domain was constructed in a yeast extracellular secretion vector, transformed into yeast strains JAR200 (MATα, Trp$^+$, Ura$^-$) and YVH10 (MATα, Trp$^-$, Ura$^+$) having different mating types, and selective-cultured. These two stains were subjected to yeast mating to select only a diploid. The selected diploid induced expression of the displayed $Fc_{CH3A}$ and the secreted $Fc_{CH3B}$. Here, the secreted $Fc_{CH3B}$ that is secreted extracellularly is combined with the displayed $Fc_{CH3A}$ expressed on the surface of the yeast cell through non-covalent binding, such that the heterodimeric heavy chain constant region is formed on the surface of the yeast cell.

The yeast cell surface expression system of the heterodimeric heavy chain constant region described above may be used to evaluate the heterodimer formation yield of the heavy chain constant region expressed by the diploid. Specifically, when the formation of the heterodimeric heavy chain constant region expressed by the diploid is dominant over the homodimer formation, the secreted $Fc_{CH3B}$ that is extracellularly secreted in the yeast is combined with the displayed $Fc_{CH3A}$ expressed on the surface of the yeast cell and immobilized to the cell surface, and thus the secreted $Fc_{CH3B}$ is detected on the yeast cell surface. On the other hand, when the homodimer formation of the heavy chain constant region expressed by diploid is dominant over the heterodimer formation, the secreted $Fc_{CH3B}$ is not immobilized on the yeast cell surface but is released into the medium, and thus it is not detected on the yeast cell surface. Therefore, a detection level of the secreted $Fc_{CH3B}$ immobilized on the yeast cell surface may be used to compare the heterodimer yield of the heavy chain constant region expressed by the diploid.

In an embodiment of the present disclosure, in order to confirm the above-described system for evaluating the heterodimer formation yield, a pair of CH3 domain mutants having different heterodimeric heavy chain constant region formation yields was used to construct a diploid by using the above described method, and then a detection level of the secreted $Fc_{CH3B}$ immobilized on the yeast cell surface was measured, and it was confirmed that there was a correlation between a detection degree of the secreted $Fc_{CH3B}$ on the yeast cell surface and the formation yield of the heterodimeric heavy chain constant region, which means that the formation yield of the heterodimeric heavy chain constant region is able to be evaluated by using the yeast cell surface expression system of the heterodimeric heavy chain constant region.

In another embodiment of the present disclosure, a heterodimeric heavy chain constant region mutant pair combination library in which a mutation is introduced into a CH3 domain interaction surface, was constructed. Specifically, the heterodimeric heavy chain constant region mutant pair combination library in which hydrophobic core regions (L351, T366, L368, and Y407) affecting stability of the Fc protein are conserved and a mutated pair is introduced into two pairs of electrostatic binding pairs (K370-E357/S364 and D399-K392/K409) located at edges of the hydrophobic core regions, was constructed. These two electrostatic attractive forces are known to contribute to the formation of the dimer of wild-type Fc (Gunasekaran et al., 2010; Choi et al., 2013). Thus, by substituting the above-described electrostatic attractive moiety with a moiety inducing selective interaction between the CH3A domain and the CH3B domain, the formation yield of the heterodimeric heavy chain constant region was intended to be enhanced.

In addition, the first CH3 domain and the second CH3 domain may be included in the vector in the form of the heavy chain constant region including the CH3 domain.

Further, the vector includes the hinge-CH2-CH3 portion of the human antibody heavy chain (moiety 225-447, EU number), and the Cys of the hinge portion (THTCPPCP) may be substituted with Ser (THTSPPSP) to avoid homodimer formation. Further, in order to prevent excessive glycosylation during yeast expression, Asn297, the N-glycosylated portion of the heavy chain constant region, may be replaced with Gln (Asn297Gln).

In a method for evaluating heterodimer formation of the antibody CH3 domain, the heterodimer of the antibody CH3 domain may include the following mutation:

(A1) substitution of an amino acid at position K370 of a first CH3 domain; and
substitution of an amino acid at position E357 and/or position S364 of a second CH3 domain; or
(B1) substitution of an amino acid at position D399 of a first CH3 domain; and
substitution of an amino acid at position K392 and/or position K409 of a second CH3 domain.

In addition, the method for evaluating the heterodimer formation of the antibody CH3 domain may be used for screening of a mutant in which heterodimeric heavy chain formation is preferred, selection of the mutant, evaluating a formation yield of heterodimeric heavy chain, and preparation of a library of the mutant in which the heterodimeric heavy chain formation is preferred.

In addition, an aspect of the present disclosure provides a heterodimer library of an antibody CH3 domain including the following mutation:

(A1) substitution of an amino acid at position K370 of a first CH3 domain; and
substitution of an amino acid at position E357 and/or position S364 of a second CH3 domain; or
(B1) substitution of an amino acid at position D399 of a first CH3 domain; and
substitution of an amino acid at position K392 and/or position K409 of a second CH3 domain.

Preferably, in the (A1) mutation,
K370 may be substituted with glutamic acid (E), methionine (M) or aspartic acid (D);
E357 may be substituted with asparagine (N), isoleucine (I), or methionine (M); and S364 may be substituted with threonine (T) or tryptophan (W).

More preferably, in the (A1) mutation, (A1-1) K370 may be substituted with glutamic acid (E), and E357 may be substituted with asparagine (N);

(A1-2) K370 may be substituted with glutamic acid (E), E357 may be substituted with isoleucine (I), and S364 may be substituted with threonine (T);

(A1-3) K370 may be substituted with methionine (M), E357 may be substituted with methionine (M), and S364 may be substituted with tryptophan (W); or (A1-4) K370 may be substituted with an aspartic acid (D), and E357 may be substituted with methionine (M).

Preferably, in the (B1) mutation,

D399 may be substituted with glutamic acid (E) or leucine (L);

K392 may be substituted with glutamic acid (E), serine (S) or glycine (G); and

K409 may be substituted with leucine (L) or methionine (M).

More preferably, in the (B1) mutation, (B1-1) D399 may be substituted with glutamic acid (E), and K392 may be substituted with glutamic acid (E);

(B1-2) D399 may be substituted with leucine (L), K392 may be substituted with serine (S), and K409 may be substituted with leucine (L); or (B1-3) D399 may be substituted with leucine (L), K392 may be substituted with glycine (G), and K409 may be substituted with methionine (M).

The heterodimer library of the antibody CH3 domain may further include:

a mutation in which K409 of the first CH3 domain is substituted with tryptophan (W), D399 of the second CH3 domain is substituted with valine (V), and F405 is substituted with threonine (T).

Further, in another embodiment of the present disclosure, an additional secondary library was constructed to improve the heterodimer formation yield of the selected mutant pair in the heterodimeric heavy chain constant region mutant pair combination library. Specifically, a mutant was introduced into the electrostatic pair (E357/S364-K370 and K392/K409-D399) present at symmetrical position of the mutation site of the selected mutant, thereby constructing a library. Therefore, the heterodimer formation yield of the selected mutant was intended to be additionally enhanced by introducing the mutation into the moiety interacting with the mutant pair introduced from the existing library at the time of forming the homodimer.

Accordingly, the heterodimer library of the antibody CH3 domain may further include the following mutation:

(A2) substitution of amino acids at position E370 and position S364 of the first CH3 domain, or substitution of the amino acid at position E357 of the second CH3 domain.

Further, preferably, in the A2 mutation,

E370 may be substituted with aspartic acid (D), alanine (A), glycine (G), or asparagine (N);

S364 may be substituted with tryptophan (W) or tyrosine (Y); and

E357 may be substituted with asparagine (N).

Further, more preferably, in the A2 mutation, (A2-1) E370 may be substituted with aspartic acid (D), S364 may be substituted with tryptophan (W), and E357 may be substituted with asparagine (N);

(A2-2) E370 may be substituted with alanine (A), S364 may be substituted with tyrosine (Y), and E357 may be substituted with asparagine (N);

(A2-3) E370 may be substituted with glycine (G), and S364 may be substituted with tryptophan (W); or (A2-4) E370 may be substituted with asparagine (N), and S364 may be substituted with tryptophan (W).

In addition, the heterodimer of the antibody CH3 domain may further include the following mutation:

(B2) substitution of an amino acid at position K392 and/or K409 of the first CH3 domain; and substitution of the amino acid at position D399 of the second CH3 domain.

Preferably, in the B2 mutation,

K392 may be substituted with isoleucine (I), arginine (R), cysteine (C), leucine (L), serine (S), or asparagine (N);

K409 may be substituted with arginine (R); and

D399 may be substituted with glycine (G), tryptophan (W), cysteine (C), serine (S), or valine (V).

More preferably, in the B2 mutation, (B2-1) K392 may be substituted with isoleucine (I), and D399 may be substituted with glycine (G);

(B2-2) K392 may be substituted with arginine (R), K409 may be substituted with arginine (R), and D399 may be substituted with tryptophan (W);

(B2-3) K392 may be substituted with cysteine (C), and D399 may be substituted with cysteine (C);

(B2-4) K392 may be substituted with leucine (L), and D399 may be substituted with serine (S);

(B2-5) K392 may be substituted with serine (S), and D399 may be substituted with glycine (G); or (B2-6) K392 may be substituted with asparagine (N), and D399 may be substituted with valine (V).

The number of amino acids in the antibody chain is based on EU numbering (Cunningham, Pflumm et al. 1969).

The present disclosure also provides a method for producing a CH3 domain mutant (heterodimeric CH3) in which formation of a heterodimeric heavy chain constant region is preferred, the method including:

(1') substituting an amino acid at position K370 of a first CH3 domain and substituting an amino acid at position E357 and/or position S364 of a second CH3 domain; or (1") substituting an amino acid at position D399 of the first CH3 domain and substituting an amino acid at position EK392 and/or position K409 of the second CH3 domain; and (2) combining the first CH3 domain and the second CH3 domain.

In addition, an aspect of the present disclosure provides a heterodimer of an antibody CH3 domain comprising the following mutation:

(A1) substitution of an amino acid at position K370 of a first CH3 domain; and substitution of an amino acid at position E357 and/or position S364 of a second CH3 domain; or (B1) substitution of an amino acid at position D399 of a first CH3 domain; and substitution of an amino acid at position K392 and/or K409 of a second CH3 domain.

Preferably, in the (A1) mutation,

K370 may be substituted with glutamic acid (E), methionine (M) or aspartic acid (D);

E357 may be substituted with asparagine (N), isoleucine (I), or methionine (M); and S364 may be substituted with threonine (T) or tryptophan (W).

Preferably, in the (A1) mutation, (A1-1) K370 may be substituted with glutamic acid (E), and E357 may be substituted with asparagine (N);

(A1-2) K370 may be substituted with glutamic acid (E), E357 may be substituted with isoleucine (I), and S364 may be substituted with threonine (T);

(A1-3) K370 may be substituted with methionine (M), E357 may be substituted with methionine (M), and S364 may be substituted with tryptophan (W); or (A1-4) K370 may be substituted with an aspartic acid (D), and E357 may be substituted with methionine (M).

Preferably, in the (B1) mutation,

D399 may be substituted with glutamic acid (E) or leucine (L); and

K392 may be substituted with glutamic acid (E), serine (S) or glycine (G);

K409 may be substituted with leucine (L) or methionine (M).

More preferably, in the (B1) mutation, (B1-1) D399 may be substituted with glutamic acid (E), and K392 may be substituted with glutamic acid (E);

(B1-2) D399 may be substituted with leucine (L), K392 may be substituted with serine (S), and K409 may be substituted with leucine (L); or (B1-3) D399 may be substituted with leucine (L), K392 may be substituted with glycine (G), and K409 may be substituted with methionine (M).

The heterodimer of the antibody CH3 domain may further comprise:

a mutation in which K409 of the first CH3 domain is substituted with tryptophan (W), D399 of the second CH3 domain is substituted with valine (V), and F405 is substituted with threonine (T).

In addition, the heterodimer of the antibody CH3 domain may further comprise the following mutation:

(A2) substitution of amino acids at positions E370 and S364 of the first CH3 domain, or substitution of the amino acid at position E357 of the second CH3 domain.

Further, preferably, in the A2 mutation,

E370 may be substituted with aspartic acid (D), alanine (A), glycine (G), or asparagine (N);

S364 may be substituted with tryptophan (W) or tyrosine (Y);

E357 may be substituted with asparagine (N).

Further, more preferably, in the A2 mutation, (A2-1) E370 may be substituted with aspartic acid (D), S364 may be substituted with tryptophan (W), and E357 may be substituted with asparagine (N);

(A2-2) E370 may be substituted with alanine (A), S364 may be substituted with tyrosine (Y), and E357 may be substituted with asparagine (N);

(A2-3) E370 may be substituted with glycine (G), and S364 may be substituted with tryptophan (W); or (A2-4) E370 may be substituted with asparagine (N), and S364 may be substituted with tryptophan (W).

In addition, the heterodimer of the antibody CH3 domain may further include the following mutation:

(B2) substitution of an amino acid at position K392 and/or K409 of the first CH3 domain; and substitution of the amino acid at position D399 of the second CH3 domain.

Preferably, in the B2 mutation,

K392 may be substituted with isoleucine (I), arginine (R), cysteine (C), leucine (L), serine (S), or asparagine (N);

K409 may be substituted with arginine (R);

D399 may be substituted with glycine (G), tryptophan (W), cysteine (C), serine (S), or valine (V).

More preferably, in the B2 mutation, (B2-1) K392 may be substituted with isoleucine (I), and D399 may be substituted with glycine (G);

(B2-2) K392 may be substituted with arginine (R), K409 may be substituted with arginine (R), and D399 may be substituted with tryptophan (W);

(B2-3) K392 may be substituted with cysteine (C), and D399 may be substituted with cysteine (C);

(B2-4) K392 may be substituted with leucine (L), and D399 may be substituted with serine (S);

(B2-5) K392 may be substituted with serine (S), and D399 may be substituted with glycine (G); or (B2-6) K392 may be substituted with asparagine (N), and D399 may be substituted with valine (V).

The number of amino acids in the antibody chain is based on EU numbering (Cunningham, Pflumm et al. 1969).

In addition, the heterodimer of the antibody CH3 domain is preferably a heterodimer of an antibody CH3 domain which is characterized by being included in a Fc portion of an immunoglobulin selected from the group consisting of IgG, IgM, IgA, IgD and IgE, but is not limited thereto. Further, in the heterodimer of the antibody CH3 domain, it is preferred that the IgG is human IgG, but is not limited thereto. In the heterodimer of the antibody CH3 domain, it is preferred that the human IgG is selected from the group consisting of IgG1, IgG2, IgG3, and IgG4, but is not limited thereto.

In addition, the present disclosure also provides a heterodimeric heavy chain constant region (heterodimeric Fc) pair including the heterodimer of the CH3 domain and a bispecific antibody including the heterodimer of the CH3 domain.

The bispecific antibody is preferably any one selected from the group consisting of scFv-Fc, scIgG(scFab-Fc), (Fv)$_2$-Fc, mAb-Fv, and Fv-Fc, but is not limited thereto. The fusion protein is preferably in the form of Protein-Fc, but is not limited thereto.

The CH3 heterodimer in which the mutation is induced in the CH3 domain of the heavy chain constant region of the antibody according to the present disclosure may constitute a heterodimeric heavy chain constant region pair protein, wherein the heterodimeric heavy chain constant region pair protein may be in the form of a bispecific antibody in which antibodies having different antigen specificities are fused into a heavy chain variable region (VH), a light chain variable region (VL), a single chain antibody fragment (scFv) or a single chain antibody fragment (scFab) to be capable of binding simultaneously to two different antigens, and various types of bispecific antibodies of a bispecific variable region fusion monoclonal antibody (mAb-Fv) in which variable single antigen binding domains (VH, VL), respectively, are fused to a heavy chain C-terminus of a typical IgG, or an antibody (Fv-Fc) capable of monovalently binding to a single antigen by fusing a heavy chain variable region (VH) and a light chain variable region (VL) binding to a single antigen, or an antibody constant region fusion protein (Protein-Fc) capable of specifically recognizing one or two kinds of proteins by fusing a cell membrane receptor extracellular domain, a peptide, a single domain antibody, a ligand, a toxin, etc., capable of binding to a specific protein.

Herein, the term "single chain antibody fragment (scFv)" refers to a VH-L-VL to VL-L-VH polypeptide in which one VH and one VL are linked using a suitable peptide linker (L) having at least 12 residues, and an antibody fragment having an antigen-binding activity.

In addition, the term single chain antibody fragment (scFab) refers to a VL-CL-L-VH-CH1 to VH-CH1-L-VL-CL polypeptide in which a heavy chain fragment expressed from one VH up to CH1 is linked to a light chain including one VL and CL portion using a suitable peptide linker (L) having at least 34 residues, and an antibody fragment having an antigen-binding activity.

Further, Fv refers to a minimum antibody fragment including a complete antigen binding site. The term "Fv-Fc" used herein refers to an antibody in which a heavy chain variable region (VH) and a light chain variable region (VL) that bind to a single antigen are fused to N-terminus or C-terminus of the heterodimeric heavy chain constant region pair protein to be capable of binding to a single antigen in a monovalent form.

In addition, the term "mAb-Fv" used herein refers to an antibody in which a heavy chain variable region (VH) and a light chain variable region (VL) are fused to IgG heavy chain C-terminus in a typical form, respectively, to be capable of binding to an antigen in a trivalent form, or a bispecific antibody capable of divalently binding to a mAb antigen and monovalently binding to a Fv antigen.

In addition, the term "antibody constant region fusion protein (Protein-Fc)" used herein refers to a fusion protein in which a cell membrane receptor extracellular domain, a peptide, a single domain antibody, a ligand, a toxin, or the like, capable of binding to a specific protein is fused to N-terminus or C-terminus of the heterodimeric heavy chain constant region pair protein according to the present disclosure, thereby being capable of specifically recognizing one or two kinds of proteins.

In addition, an aspect of the invention provides a pharmaceutical composition including the heterodimeric heavy chain constant region pair, the bispecific antibody, the monovalent antigen binding antibody or the fusion protein.

The bispecific antibody or fusion protein produced by the present disclosure may specifically target an antigen or protein associated with a tumor, an angiogenesis-related disease or an immune disease, thereby being useful for the pharmaceutical composition capable of treating or preventing the diseases.

Here, the pharmaceutical composition including the bispecific antibody or the fusion protein produced according to the present disclosure may increase therapeutic effects of the diseases as compared to a pharmaceutical composition including a monoclonal antibody that targets only one kind of target protein, since a pathogenesis mechanism is not induced by one protein, but various proteins act in a redundant, bypass, and stepwise manner, to be able to simultaneously target two kinds of antigens associated with a tumor or an immune disease that occurs.

The term "treatment" used herein means any action that improves or alleviates symptoms caused by a disease according to administration of the composition of the present disclosure.

The pharmaceutical composition of the present disclosure may be used for treatment or prevention of cancer, angiogenesis-related diseases or immunological diseases.

The cancer may include, but is not limited to, squamous cell carcinoma, small cell lung cancer, non-small cell lung cancer, adenocarcinoma of lung, squamous cell carcinoma of the lung, peritoneal cancer, skin cancer, skin or intraocular melanoma, rectal cancer, cancer vicinity anus, esophageal cancer, small bowel cancer, endocrine cancer, parathyroid cancer, adrenal cancer, soft tissue sarcoma, urinary tract cancer, chronic or acute leukemia, lymphocytic lymphoma, hepatocellular carcinoma, gastrointestinal cancer, pancreatic cancer, glioblastoma, cervical cancer, ovarian cancer, liver cancer, bladder cancer, liver tumor, breast cancer, colon cancer, colorectal cancer, endometrial or uterine cancer, salivary gland cancer, kidney cancer, liver cancer, prostate cancer, vulva cancer, thyroid cancer, liver cancer or head and neck cancer.

The angiogenesis-related disease may include, but is not limited to, diabetic retinopathy, macular degeneration, senile macular degeneration, retinopathy of prematurity, corneal transplant rejection, neovascular glaucoma and fibroplasia retrolental, epidemic conjunctivitis, vitamin A deficiency, over-wearing contact lenses, atopic keratitis, upper corneal limbal keratitis, pterygium psoriasis keratitis, Sjogren's syndrome, acne vulgaris, phlyctenular keratitis, syphilis, mycobacterial infection, fatty degeneration, chemical burn, bacterial ulcer, fungal ulcer, herpes simplex infection, herpes zoster infection, protozoal infection, Kaposi sarcoma, Mooren ulcer, terrien marginal degeneration keratoconjunctival keratolysis, mental trauma, rheumatoid arthritis, systemic erythema, multiple arteritis, Wegener's sarcoidosis, scleritis, Steve Johnson's disease, peripheral scarring radial keratectomy or corneal transplant rejection, and the like.

The immune disease may include organ transplant complication, rheumatoid arthritis, multiple sclerosis, myasthenia gravis, Grave's disease, Hashimoto's thyroiditis, Addison's disease, vitiligo, scleroderma, Goodpasture syndrome, Behcet's disease, Crohn's disease, Ankylosing spondylitis, uveitis, thrombocytopenic purpura, pemphigus vulgaris, juvenile diabetes, autoimmune anemia, cryoglobulinemia, adrenal leukodystrophy (ALD), systemic lupus erythematosus (SLE), etc., but is not limited in view of the kind.

When the pharmaceutical composition according to the present disclosure is formulated, a diluent or an excipient such as a filler, an extender, a binder, a wetting agent, a disintegrant, a surfactant, or the like, which is generally used, is used.

A solid formulation for oral administration includes tablet, pill, powder, granule, capsule, troche, etc., and the solid formulation is prepared by admixing at least one excipient such as starch, calcium carbonate, sucrose, lactose, gelatin, or the like, with one or more of the compounds represented by the present disclosure. Further, in addition to the simple excipient, lubricants such as magnesium stearate talc, are also used. Liquid formulation for oral administration may include suspension, solution, emulsion, syrup, and the like, and may include various excipients, for example, wetting agent, sweetener, flavoring agent, preservative, and the like, in addition to generally used simple diluents such as water, liquid paraffin, and the like.

A preparation for parenteral administration includes sterilized aqueous solution, non-aqueous agent, suspension, emulsion, freeze-dried preparation, and suppositories, etc.

Examples of the non-aqueous agent and the suspension may include propylene glycol, polyethylene glycol, vegetable oil such as olive oil, injectable ester such as ethyl oleate, and the like. As a suppository base, witepsol, macrogol, Tween 61, cocoa butter, laurinum, glycerol, gelatin, etc., may be used.

The composition of the present disclosure may be administered orally or parenterally (for example, intravenously, subcutaneously, intraperitoneally or topically) depending on the intended method, and the dosage may vary depending on the condition and the weight of the patient, the degree of disease, the type of drug, the administration route and time, but may be appropriately selected by those skilled in the art.

The composition according to the present disclosure is administered in a pharmaceutically effective amount. In the present disclosure, "pharmaceutically effective amount" means an amount sufficient to treat a disease at a reasonable benefit/risk ratio applicable to medical treatment, and an effective dose level may be determined by factors including the type of disease, severity of the patient, activity of the drug, sensitivity to the drug, administration time, administration route and rate of release, duration of treatment, simultaneously used drug, and by factors well known in other medical fields. The composition of the present disclosure may be administered as an individual therapeutic agent or in combination with other therapeutic agents, may be administered sequentially or concurrently with conventional therapeutic agents, and may be administered singly or multiply. It is important to administer an amount at which the maximum effect is able to be obtained with a minimum amount without causing side effects in consideration of all of the above-described factors, and may be easily determined by those skilled in the art.

Specifically, the effective amount of the compound according to the present disclosure may vary depending on the age, sex, and body weight of the patient. Generally, 0.01 to 100 mg, preferably 0.01 to 10 mg per body weight may be administered daily or every other day or may be administered into one to three divided doses per day. However, the dosage may increase or decrease depending on the route of administration, the severity of obesity, sex, weight, age, etc. Therefore, the dosage does not limit the scope of the present disclosure in any way.

Further, the present disclosure also provides a method for producing a heterodimeric heavy chain constant region pair ((hinge-CH2-CH3A)×(hinge-CH2-CH3B)) protein including the following steps:

producing a recombinant heavy chain constant region pair protein expression vector by cloning nucleic acids obtained by fusing the above-produced CH3 domain mutant pair to C-terminus of an antibody heavy chain constant region wild-type hinge-CH2 domain, respectively;

expressing a recombinant heavy chain constant region pair protein by co-transformation of the produced expression vector; and purifying and recovering the co-expressed recombinant heavy chain constant region pair protein.

Further, the present disclosure may provide a heterodimeric heavy chain constant region pair ((hinge-CH2-CH3A)×(hinge-CH2-CH3B)) protein produced by the method.

EXAMPLE

Hereinafter, Examples of the present disclosure will be described in detail. However, the following Examples are provided only to more easily understand the present disclosure, and the scope of the present disclosure is not limited to these Examples.

Example 1: Construction of Yeast Cell Surface Expression System of Human Antibody Heterodimeric Heavy Chain Constant Region A system for quantitatively evaluating a heterodimeric formation yield was constructed to select a CH3 domain mutant pair forming a human CH3 domain heterodimer at a high yield by using directed evolution. FIG. 1 is a schematic diagram showing a strategy for expressing a human antibody heterodimeric heavy chain constant region on a surface of a yeast cell using yeast mating. Specifically, a heavy chain constant region (displayed $Fc_{CH3A}$) including a CH3A domain was cloned into a yeast cell surface expression vector (pCTCON) (Kim et al., 2007) using restriction enzymes NheI/BamHI to construct a pCTCON-Displayed $Fc_{CH3A}$ vector (FIG. 2), and a heavy chain constant region (secreted $Fc_{CH3B}$) including a CH3B domain was cloned into a yeast extracellular secretion vector (pSEC2) (Baek et al. 2014) using restriction enzymes EagI/AflII to construct a pSEC2-Secreted $Fc_{CH3B}$ vector (FIG. 3). Here, the constructed displayed $Fc_{CH3}A$ and the secreted FcCH3B include a hinge-CH2-CH3 portion of the human antibody heavy chain (residues 225-447, EU number), Cys in the hinge portion (THTCPPCP) was substituted with Ser (THT-SPPSP) to avoid homodimer formation. In addition, in order to prevent excessive glycosylation during yeast expression, Asn297, the N-glycosylated portion of the heavy chain constant region, was substituted with Gln (Asn297Gln).

The constructed pCTCON-displayed $Fc_{CH3A}$ vector was transformed into JAR200 (MATα, Trp$^+$, Ura$^-$) yeast strains by electroporation and selected in a selective medium SDCAA+Ura (20 g/L glucose, 6.7 g/L yeast nitrogen base without amino acids, 5.4 g/L Na$_2$HPO$_4$, 8.6 g/L NaH$_2$PO$_4$, 5 g/L casamino acids, 0.2 mg/L uracil) (Sigma-Aldrich). The pSEC2-secreted $Fc_{CH3B}$ vector was transformed into YVH10 (MATα, Trp$^-$, Ura$^+$) yeast strains by electroporation and selected in a selective medium SDCAA+Trp (20 g/L glucose, 6.7 g/L yeast nitrogen base without amino acids, 5.4 g/L Na$_2$HPO$_4$, 8.6 g/L NaH$_2$PO$_4$, 5 g/L casamino acids, 0.4 mg/L tryptophan) (Sigma-Aldrich).

Two types of selected and cultured yeast strains were subjected to yeast mating. Specifically, in the case of yeast mating, the selected two kinds of yeasts each in amount $1.5 \times 10^7$ were mixed with each other, and washed three times with YPD (20 g/L dextrose, 20 g/L peptone, 10 g/L yeast extract, 14.7 g/L sodium citrate, 4.29 g/L citric acid, pH 4.5) (Sigma-Aldrich) medium, and resuspended in 100 µl of YPD medium, and then plated on a YPD plate and cultured at 30° C. for 6 hours. The yeast-plated portion was washed three times with the selective medium SDCAA (20 g/L glucose, 6.7 g/L yeast nitrogen base without amino acids, 5.4 g/L Na$_2$HPO$_4$, 8.6 g/L NaH$_2$PO$_4$, 5 g/L casamino acids) (Sigma-Aldrich), then resuspended in SD-CAA medium so that a final yeast concentration was $1 \times 10^6$ or less, and cultured at 30° C. for 24 hours. Then, only mated diploids were selected. In the selected diploids, SGCAA (20 g/L galactose, 6.7 g/L yeast nitrogen base without amino acids, 5.4 g/L Na$_2$HPO$_4$, 8.6 g/L NaH$_2$PO$_4$, 5 g/L casamino acids) (Sigma-Aldrich) medium was used to induce expression of the displayed $Fc_{CH3A}$ and the secreted $Fc_{CH3B}$. The secreted $Fc_{CH3B}$ that was extracellularly secreted was combined with non-covalent binding to the displayed $Fc_{CH3A}$ expressed on a yeast cell surface, such that the heterodimeric heavy chain constant region was formed on the yeast cell surface.

The yeast cell surface expression system of the heterodimeric heavy chain constant region described above was used to evaluate the heterodimer formation yield of the heavy chain constant region in which the diploid was expressed. Specifically, when heterodimer formation of the heavy chain constant region expressed by the diploid is dominant over the homoduplex formation, the secreted $Fc_{CH3B}$ that was extracellularly secreted was combined with the displayed $Fc_{CH3A}$ expressed on the yeast cell surface and immobilized on the cell surface, and thus the secreted $Fc_{CH3B}$ was detected on the yeast cell surface. On the other hand, when the homodimer formation of the heavy chain constant region expressed by the diploid was dominant over the heterodimer formation, the secreted $Fc_{CH3B}$ was not immobilized on the yeast cell surface, but discharged into the medium, and thus the secreted FcCH3B was not detected on the yeast cell surface. Therefore, a detection level of the secreted $Fc_{CH3B}$ immobilized on the yeast cell surface may be used to compare the heterodimer yield of the heavy chain constant region expressed by the diploid.

Example 2: Evaluation of Yeast Cell Surface Expression System of Human Antibody Heterodimeric Heavy Chain Constant Region In order to confirm the heterodimer formation yield evaluation system constructed in Example 1, a CH3 domain mutant pair having different heterodimeric heavy chain constant region formation yields was used to construct the dimer by using the above-described method, and a detection level of the secreted $Fc_{CH3B}$ immobilized on the yeast cell surface was measured (FIG. 4). The used CH3 domain mutant pair were W-VT (~61%) (Choi et al., 2013), EW-RVT (~91%) (Choi et al., 2013), and KiH (~86%) (Atwell et al., 1997), and as a control group, a hole-hole mutant pair of wild-type heavy chain constant region and KiH were used. Table 1 shows the sequence of the used CH3 domain mutant pair.

TABLE 1

CH3 domain mutant pair sequence used for evaluating yeast cell surface expression system of heterodimeric heavy chain constant region

| Mutant name | Displayed $Fc_{CH3A}$ (CH3A chain) | Secreted $Fc_{CH3B}$ (CH3B chain) |
| --- | --- | --- |
| W-VT | K409W | D399V/F405T |
| EW-RVT | K360E/K409W | Q347R/D399V/F405T |
| Hole-Hole (Genentech) | T366S/L368A/Y407V | T366S/L368A/Y407V |
| KiH (Genentech) | T366S/L368A/Y407V | T366W |

Specifically, the diploid in which the expression of the heterodimeric heavy chain constant region was induced was reacted with an antibody recognizing flag-tag included in the secreted $Fc_{CH3B}$ (anti-Flag mouse mAb, F3165) (Sigma-Aldrich) and an antibody conjugated with PE (phycoerythrin conjugated anti-mouse mAb, sc-3738) (Santa Cruz biotechnology), and a signal of PE was analyzed by flow cytometry. FIG. 4A is a histogram showing a PE signal value measured using FACS Caliber (Becton & Dickinson) of different CH3 domain mutant pairs, and FIG. 4B shows data showing mean fluorescence intensity (MFI) at the positive peak of the histogram as compared to the EW-RVT CH3 domain mutant pair (normalization of the mean fluorescence sensitivity of EW-RVT to 100%). The diploid expressing the mutant pair in which the heterodimer formation is preferred exhibits a higher level of PE signal value than that of the control, which is proportional to the above-described heterodimer formation yield. This result implies that there is a correlation between the detection degree of the secreted $Fc_{CH3B}$ on the yeast cell surface and the formation yield of the heterodimeric heavy chain constant region, and it means that the formation yield of the heterodimeric heavy chain constant region is able to be evaluated by using the yeast surface expression system of the heterodimeric heavy chain constant region.

Example 3: Human Antibody Heterodimeric Heavy Chain Constant Region Mutant Pair Combination Library Construction Strategy By using the above-described yeast cell surface expression system of the heterodimeric heavy chain constant region, a heterodimeric heavy chain constant region mutant pair combination library in which a mutation was introduced into a CH3 domain interaction surface, was constructed. As a site where the mutant pair was introduced, hydrophobic core regions (L351, T366, L368, Y407) affecting stability of the heavy chain constant region protein were preserved, and two pairs of electrostatic pair (K370-E357/S364 and D399-K392/K409) positioned at the edge of the hydrophobic core region were selected. The two pairs of electrostatic attraction are known to contribute to the formation of a dimer in the wild type heavy chain constant region (Gunasekaran et al., 2010; Choi et al., 2013). Therefore, by substituting a residue having electrostatic attraction with a residue inducing selective interaction between the CH3A domain and the CH3B domain, the formation yield of the heterodimeric heavy chain constant region formation was intended to improved.

FIG. 5 is a schematic diagram showing a library construction strategy for obtaining a CH3 domain mutant pair having a high heterodimer formation yield by introducing a mutation into a CH3 domain interaction surface. Specifically, based on the W-VT mutant pair (Choi et al., 2013) having the heterodimer formation yield of about 61%, two libraries were designed by introducing mutations into two pairs of electrostatic pairs $K370_{CH3A}$-$E357/S364_{CH3B}$ and $D399_{CH3A}$-$K392/K409_{CH3B}$ positioned at the opposite side of the W-VT mutation site ($K409W_{CH3A}$-$D399V/F405T_{CH3B}$), respectively, and a LibA1 library with mutation introduced into $K370_{CH3A}$, $E357_{CH3B}$, and $S364_{CH3B}$, and a LibB1 library with mutation introduced into $D399_{CH3A}$, $K392_{CH3B}$, and $K409_{CH3B}$ were constructed. Here, the amino acid that was mutated at the mutation site was allowed to include DNB. DNB encoded D (D=A, G, T) for the first, N (N=A, T, C, G) for the second, and B (B=C, G, T) for the third, and thus it could be substituted with non-polar amino acid (Gly, Ala, Val, Leu, Ile, Phe, Tyr, Trp, Cys, Met) at a probability of 55.6%, uncharged/polar amino acid (Ser, Thr, Asn) at a probability of 27.8%, positive charge/negative charge amino acid (Asp, Glu, Lys, Arg) at a probability of 13.9%, and termination codon at a probability of 2.8%, and could not be substituted with Pro, His, or Gln.

For the production of the LibA1 and LibB1 libraries, first, a displayed $Fc_{CH3A}$ library including a CH3A domain mutant and a secreted $Fc_{CH3B}$ library including a CH3B domain mutant were produced, respectively. The genes of each library were produced by performing overlapping PCR using the primers shown in Table 2, and the displayed $Fc_{CH3A}$ library gene (5 μg) was mixed with NheI/BamHI restriction enzymes-treated yeast surface expression vector pCTCON-displayed $Fc_{CH3A}$ (1 μg), transformed into JAR200 (MATα) yeast strain, and constructed by homologous recombination. The secreted $Fc_{CH3B}$ library gene (5 μg) was mixed with EagI/AflII restriction enzymes-treated yeast extracellular secretion vector pSEC2-secreted $Fc_{CH3B}$ (1 μg), transformed into YVH10 (MATα) yeast strain, and constructed by homologous recombination.

TABLE 2

Oligonucleotide sequence of primer used in constructing LibA1 library and LibB1 library

| Library | Purpose | Direction | Length | Oligonucleotide Sequence (5'-3') |
| --- | --- | --- | --- | --- |
| LibA1 | Displayed $Fc_{CH3A}$ (CH3A) | Amplifying Fc fragment 1 | Forward | 22 | GTTCCAGACTACGCTCTGCAGG (SEQ ID NO: 101) |

TABLE 2-continued

Oligonucleotide sequence of primer used in constructing LibA1 library and LibB1 library

| Library | | Purpose | Direction | Length | Oligonucleotide Sequence (5'-3') |
|---|---|---|---|---|---|
| | | Amplifying Fc fragment 1 | Reverse | 20 | GACCAGGCAGGTCAGGCTGA (SEQ ID 102) |
| | | Amplifying Fc fragment 2 | Forward | 45 | TCAGCCTGACCTGCCTGGTCDNBGG CTTCTATCCCAGCGACATCG (SEQ ID NO: 103) |
| | | Amplifying Fc fragment 2 | Reverse | 35 | TCGATTTTGTTACATCTACACTGTT GTTATCAGAT (SEQ ID NO: 104) |
| | Secreted Fc$_{CH3B}$ (CH3B) | Amplifying Fc fragment 1 | Forward | 26 | CTCAACCGGTTATTTCTACTACCGTC (SEQ ID NO: 105) |
| | | Amplifying Fc fragment 1 | Reverse | 18 | ATCCCGGGATGGGGGCAG (SEQ ID NO: 106) |
| | | Amplifying Fc fragment 2 | Forward | 63 | CTGCCCCCATCCCGGGATDNBCTGA CCAAGAACCAGGTCDNBCTGACCTG CCTGGTCAAAGGC (SEQ ID NO: 107) |
| | | Amplifying Fc fragment 2 | Reverse | 33 | GAACAAAGTCGATTTTGTTACATCT ACACTGTT (SEQ ID NO: 108) |
| LibB1 | Displayed Fc$_{CH3A}$ (CH3A) | Amplifying Fc fragment 1 | Forward | 22 | GTTCCAGACTACGCTCTGCAGG (SEQ ID NO: 109) |
| | | Amplifying Fc fragment 1 | Reverse | 18 | CAGCACGGGAGGCGTGGT (SEQ ID NO: 110) |
| | | Amplifying Fc fragment 2 | Forward | 42 | ACCACGCCTCCCGTGCTGDNBTCCGA CGGCTCCTTCTTCCTC (SEQ ID NO: 111) |
| | | Amplifying Fc fragment 2 | Reverse | 35 | TCGATTTTGTTACATCTACACTGTTG TTATCAGAT (SEQ ID NO: 112) |
| | Secreted Fc$_{CH3B}$ (CH3B) | Amplifying Fc fragment 1 | Forward | 26 | CTCAACCGGTTATTTCTACTACCGTC (SEQ ID NO: 113) |
| | | Amplifying Fc fragment 1 | Reverse | 58 | AGGAGCCGTCGGACACCAGCACGGG AGGCGTGGTVNHGTAGTTGTTCTCC GGCTGCCC (SEQ ID NO: 114) |
| | | Amplifying Fc fragment 2 | Forward | 57 | CTGGTGTCCGACGGCTCCTTCACCCT CTACAGCDNBCTCACCGTGGACAAG AGCAGG (SEQ ID NO: 115) |
| | | Amplifying Fc fragment 2 | Reverse | 33 | GAACAAAGTCGATTTTGTTACATCT ACACTGTT (SEQ ID NO: 116) |

The LibA1 and LibB1 mutant pair combination libraries were constructed through yeast mating between each haploid library. A detailed method of the yeast mating is described in Example 1. A size of the constructed library was confirmed by measuring the number of colonies grown on the selective medium after stepwise dilution. The LibA1 was produced to have a size of about $3.0 \times 10^7$ and the LibB1 was produced to have a size of about $2.8 \times 10^7$, both exceeded the theoretical library size of $5 \times 10^3$.

Example 4: Selection of CH3 Domain Mutant Pair Inducing High Efficient Formation of Heterodimeric Heavy Chain Constant Region from Human Antibody Heterodimeric Heavy Chain Heavy Chain Constant Region Mutant Pair Combination Libraries LibA1 and LibB1

In order to select the mutant pair in which high efficient formation of the heterodimeric heavy chain constant region was induced from the constructed libraries LibA1 and LibB1, FACS (fluorescence activated cell sorting) was performed to suspend the yeast having a high degree of immobilization of secreted $Fc_{CH3B}$ on the surface of yeast cell. Specifically, the heterodimeric heavy chain constant region library constructed in Example 3 was allowed to express on the surface of the yeast cell, primarily bound with anti-Flag mouse mAb (F3165) (Sigma-Aldrich), and secondly reacted with anti-mouse antibody conjugated with PE (phycoerythrin conjugated anti-mouse mAb, sc-3738) (Santa Cruz biotechnology), and then suspended using a FACS Aria II instrument (Becton & Dickinson). FACS was sequentially performed four times. FIG. 6A shows data obtained by comparison between mean fluorescence intensity (MFI) measured from a PE signal value obtained by detecting secreted $Fc_{CH3B}$ immobilized on a surface of the yeast cell with respect to the suspended libraries, using FACS caliber (Becton & Dickinson), and a PE signal value of the EW-RVT CH3 domain mutant pair (normalization of the mean fluorescence sensitivity of EW-RVT to 100%). Thus, suspension of the LibA1 and LibB1 libraries was confirmed.

Clones having a high degree of immobilization of the secreted $Fc_{CH3B}$ on the yeast cell surface by the above-described screening were suspended to obtain individual clones. Four individual clones A107, A108, A109, and A146 were separated from the LibA1 library and three individual clones B121, B135 and B168 were separated from the LibB1 library. The PE signal value obtained by detecting the secreted $Fc_{CH3B}$ of the selected individual clones was measured, and as a result, it was confirmed that the PE signal value was higher than that of the parent W-VT mutant pair (FIG. 6B). Sequences of CH3A and CH3B domain pairs of selected individual clones were identified using a yeast colony PCR method, and the colony PCR method has been described in detail in a previously published paper (Baek et al. 2014). Table 3 below summarizes the mutation pairs introduced into individual clones selected from the respective LibA1 and LibB1 libraries.

TABLE 3

Mutation pair introduced into individual clones selected from LibA1 and LibB1 libraries

| Mutant name | | CH3A | CH3B |
|---|---|---|---|
| LibA1 | A107 | K370E/K409W | E357N/D399V/F405T |
| | A108 | K370E/K409W | E357I/S364T/D399V/F405T |
| | A109 | K370M/K409W | E357M/S364W/D399V/F405T |
| | A146 | K370D/K409W | E357M/D399V/F405T |
| LibB1 | B121 | D399E/K409W | K392E/D399V/F403T |
| | B135 | D399L/K409W | K392S/K409L/D399V/F405T |
| | B168 | D399L/K409W | K392G/K409M/D399V/F405T |

Example 5: Evaluation of Heterodimeric Heavy Chain Constant Region Formation Ability of CH3 Domain Mutant Pair Selected from LibA1 and LibB1 Libraries A scFv-$Fc_{CH3A}$/$Fc_{CH3B}$ co-expression system was used to evaluate the heterodimer formation yield of the CH3 domain mutant selected in Example 4 above. FIG. 7 is a schematic diagram showing a scFv-$Fc_{CH3A}$/$Fc_{CH3B}$ co-expression system. An antibody purified in the scFv-$Fc_{CH3A}$/$Fc_{CH3B}$ co-expression system showed that the scFv-$Fc_{CH3A}$ homodimer (103 kDa) the scFv-$Fc_{CH3A}$/$Fc_{CH3B}$ heterodimer (78 kDa), and the $Fc_{CH3B}$ homodimer (53 kDa) had different molecular weights from each other, and thus a formation degree of the heterodimer on SDS-PAGE could be compared.

A pcDNA3.1(+)-scFv-hinge-CH2-CH3A (scFv-$Fc_{CH3A}$) vector and a pcDNA3.1(+)-hinge-CH2-CH3B ($Fc_{CH3B}$) vector, which are animal cell expression vectors used in the scFv-$Fc_{CH3A}$/$Fc_{CH3B}$ simultaneous expression system, have been described in detail in a previously published paper (Choi et al., 2013; Choi et al., 2015). The CH3 domain mutant pair of the individual clones selected in Example 4 above was cloned into an animal cell expression vector so that the CH3A mutant was expressed in the scFv-$Fc_{CH3A}$ format and the CH3B mutant was expressed in the $Fc_{CH3B}$ format. Table 4 below shows constructed scFv-$Fc_{CH3A}$/$Fc_{CH3B}$ mutant pairs, which include 3 domain mutant pairs of individual clones selected in Example 4 above, wherein the EW-RVT mutant pair was used as a control group.

TABLE 4

Mutant pair constructed for evaluation of heterodimer formation ability of mutant selected from LibA1 and LibB1 libraries

| Mutant name | | scFv-$Fc_{CH3A}$ (CH3A chain) | $Fc_{CH3B}$ (CH3B chain) |
|---|---|---|---|
| EW-RVT | | K360E/K409W | Q347R/D399V/F405T |
| LibA1 | A107 | K370E/K409W | E357N/D399V/F405T |
| | A108 | K370E/K409W | E357I/S364T/D399V/F405T |
| | A109 | K370M/K409W | E357M/S364W/D399V/F405T |
| | A146 | K370D/K409W | E357M/D399V/F405T |
| LibB1 | B121 | D399E/K409W | K392E/D399V/F405T |
| | B135 | D399L/K409W | K392S/K409L/D399V/F405T |
| | B168 | D399L/K409W | K392G/K409M/D399V/F405T |

The pcDNA3.1 (+)-scFv-$Fc_{CH3A}$ and pcDNA3.1 (+)-$Fc_{CH3B}$ animal cell expression vectors that were constructed using the HEK293-F system (Invitrogen) were used to produce antibodies by transient transfection, and the heterodimer formation ability was compared. Specifically, a mixture of an expression vector and polyethylenimine (PEI) (Polyscience) was transfected into HEK293-F cells (Invitrogen) that were suspension-grown on a serum-free FreeStyle 293 expression medium (Invitrogen) in a shaking flask (Corning). When transfecting 30 ml of the mixture in the shaking flask, HEK293-F cells were seeded at a density of $1.0 \times 10^6$ cell/ml in 30 ml of medium and cultured at 125 rpm and 8% $CO_2$. The pcDNA3.1(+)-scFv-$Fc_{CH3A}$ and pcDNA3.1(+)-$Fc_{CH3B}$ plasmid DNA that were constructed as above at the same molar ratio were diluted in a FreeStyle 293 expression medium (Invitrogen) to a total of 75 μg (each 1.25 μg/ml), and mixed with 3 ml of medium in which PEI 225 μg (7.5 μg/ml) was diluted, and then reacted at room temperature for 10 minutes. Then, the reacted mixed medium was added to 30 ml of the previously seeded cells and cultured at 125 rpm and 8% $CO_2$ for 6 days. The cell culture supernatant collected with reference to the standard protocol was applied to Protein A Sepharose column (GE healthcare), washed with PBS (pH 7.4). The antibody was eluted at pH 3.0 with 0.1 M glycine buffer and immediately neutralized with 1 M Tris buffer. The eluted antibody fraction was concentrated using an Amicon Ultra (MILLIPORE) centrifugal concentrator after the buffer was exchanged with PBS (pH 7.4) using a Dextran Desalting Column (Thermo Scientific Pierce). The purified antibody was quantified by BCA technique.

FIG. 8 shows data obtained by analyzing 5 μg of the purified antibody on SDS-PAGE under 12% non-reducing conditions. The scFv-$Fc_{CH3A}$ homodimer was observed at 103 kDa, the $Fc_{CH3B}$ homodimer was observed at 53 kDa, the $Fc_{CH3B}$ monomer was observed at 25 kDa, and the scFv-$Fc_{CH3A}$/$Fc_{CH3B}$ heterodimer was observed at 78 kDa.

The selected clones were found to have about 68 to 93% heterodimer formation ability (Table 5). Among the mutants selected from the library LibA1, A107 had a high degree of heterodimer formation ability at a yield of about 93%, which was higher than that of the control EW-RVT (about 91%), amino and then analyzing each band density on SDS-PAGE using Image J (Wayne Rasband, NIH) program. The W-VT and EW-RVT mutants were used as control groups. The result values were expressed as mean±standard deviation after three independent experiments were performed.

TABLE 6

Heterodimer formation yield of mutant selected from library and mutant in which W-VT mutation site is substituted with wild-type amino acid (SDS-PAGE analysis result)

| | Mutant name | (scFv-Fc)$_2$ (homodimer) (%) | (scFv-Fc)(Fc) (heterodimer) (%) | (Fc)$_2$ (homodimer) (%) | Fc monomer (%) |
|---|---|---|---|---|---|
| | W-VT | 1.4 ± 0.1 | 60.8 ± 3.0 | 27.8 ± 0.4 | 10.0 ± 3.3 |
| | EW-RVT | 0.5 ± 0.6 | 91.4 ± 1.2 | 1.6 ± 0.6 | 6.5 ± 1.3 |
| LibA1 | A107 | 4.2 ± 0.3 | 93.4 ± 1.1 | 2.4 ± 1.2 | ND |
| | A108 | ND | 70.5 ± 3.3 | 13.0 ± 1.1 | 16.5 ± 1.1 |
| | A109 | 0.5 ± 0.4 | 90.5 ± 2.7 | 5.8 ± 1.3 | 3.2 ± 2.1 |
| | A146 | ND | 74.5 ± 3.4 | 14.6 ± 1.8 | 10.9 ± 2.6 |
| LibB1 | B121 | 1.5 ± 1.0 | 73.3 ± 5.3 | 25.2 ± 4.0 | ND |
| | B135 | 4.1 ± 0.8 | 67.8 ± 3.2 | 27.9 ± 2.1 | 0.2 ± 0.1 |
| | B168 | 1.2 ± 0.3 | 77.7 ± 4.5 | 21.1 ± 6.4 | ND |
| Mutant where W-VT mutation site is substituted with wild type | A107$_{w/oW-VT}$ | 21.3 ± 0.4 | 78.2 ± 4.2 | 0.5 ± 2.3 | ND |
| | A109$_{w/oW-VT}$ | 5.6 ± 0.2 | 61.6 ± 4.5 | 32.8 ± 4.4 | ND |
| | A146$_{w/oW-VT}$ | 4.6 ± 1.4 | 71.0 ± 3.7 | 24.4 ± 2.5 | ND |
| | B168$_{w/oW-VT}$ | 1.6 ± 0.8 | 60.9 ± 2.4 | 37.5 ± 2.6 | ND | and among the mutants selected from the library LibB1, B168 had a high degree of heterodimer formation ability at a yield of about 78%. It was also confirmed that heterodimer formation of the A107 and B168 mutant pairs was affected by a molar ratio of the pcDNA3.1(+)-scFv-Fc$_{CH3A}$ and pcDNA3.1(+)-Fc$_{CH3B}$ plasmids added at the transfection (FIG. 9).

Since the selected individual clones included the W-VT mutation site (K409W$_{CH3A}$-D399V/F405T$_{CH3B}$), the heterodimer formation ability of the mutant pair alone that was introduced through the library selection with respect to four kinds of mutants (A107, A109, A146, and B168) having relatively high heterodimer formation ability was analyzed using the scFv-Fc$_{CH3A}$/Fc$_{CH3B}$ coexpression system described above (FIG. 10). To do this, four kinds of mutant pairs (A107$_{w/oW-VT}$, A109$_{w/oW-VT}$, A146$_{w/oW-VT}$, B168$_{w/oW-VT}$) in which the W-VT mutation site was substituted with a wild-type amino acid were constructed. Table 5 below shows sequences of the mutant pairs in which the W-VT mutation site is substituted with the wild-type amino acid.

TABLE 5

Mutant pairs constructed for evaluation of heterodimer formation ability of four kinds of mutants in which W-VT mutation site is substituted with wild-type amino acid

| | Mutant name | scFv-Fc$_{CH3A}$ (CH3A chain) | Fc$_{CH3B}$ (CH3B chain) |
|---|---|---|---|
| | W-VT | K409W | D399V/F405T |
| | EW-RVT | K360E/K409W | Q347R/D399V/F405T |
| Mutant where W-VT mutation site is substituted with wild type | A107$_{w/oW-VT}$ | K370E | E357N |
| | A109$_{w/oW-VT}$ | K370M | E357M/S364W |
| | A146$_{w/oW-VT}$ | K370D | E357M |
| | B168$_{w/oW-VT}$ | D399L | K392G/K409M |

FIG. 11 and Table 6 show quantitative data showing the heterodimer formation yield obtained by repeatedly expressing and purifying the scFv-Fc$_{CH3A}$/Fc$_{CH3B}$ heterodimer including the selected mutant and a mutant in which the W-VT mutation site was substituted with the wild-type Table 7 shows purification yield of the selected mutants. The yield when the heterodimers described in Tables 4 and 5 were expressed and purified by the above-described method was calculated by normalizing a purification yield of the heterodimer having the EW-RVT mutant pair as the control group as 100%. The purification yield of EW-RVT heterodimer was 3.1±0.7 mg/transfection 100 ml in HEK293-F cell. The heterodimer heavy chain constant region was repeatedly expressed and purified three or more times to obtain mean±SD. As a result, the heterodimer including the Fc mutant had a similar yield to that of the control group. Thus, it was determined that the introduction of the selected mutant pair through the library did not significantly impair the stability of the heavy chain constant region protein.

TABLE 7

Purification yield of mutant selected from library and mutant in which W-VT mutation site is substituted with wild-type amino acid (HEK293-F cell, about 6 days expression)

| | Mutant name | Final product after buffer change [normalization with yield of EW-RVT mutant] [%] |
|---|---|---|
| | EW-RVT | 100 |
| LibA1 | A107 | 108 ± 51.1 |
| | A108 | 125 ± 78.1 |
| | A109 | 102 ± 27.7 |
| | A146 | 127 ± 22.7 |
| LibB1 | B121 | 127 ± 29.3 |
| | B135 | 104 ± 31.4 |
| | B168 | 119 ± 24.8 |
| Mutant where W-VT mutation site is substituted with wild type | A107$_{w/oW-VT}$ | 103 ± 49.0 |
| | A109$_{w/oW-VT}$ | 86.9 ± 2.1 |
| | A146$_{w/oW-VT}$ | 89.5 ± 13.5 |
| | B168$_{w/oW-VT}$ | 96.9 ± 18.4 |

Example 6: Structural Analysis of CH3 Domain Mutant Pair Selected from LibA1 and LibB1 Libraries To confirm the reason that heterodimer formation of the CH3 domain mutant pair selected through the LibA1 and LibB1 libraries was preferred, the CH3 domain interaction surface was modeled and analyzed by using the protein structure of the known CH3 domain mutant pair EW-RVT (Choi et al., 2015).

A107 [CH3A (K370E/K409W): CH3B (E357N/D399V/F405T)]

In the wild type CH3 domain interaction surface, K370 of one domain was adjacent to E357 and S364 of another domain. Among them, the electrostatic interaction between K370 and E357 of the other domain contributed to the dimer formation of the CH3 domain. In the A107 mutant screened in the LibA1 library, an electrostatic binding between the CH3A domain and the CH3B domain was substituted with a hydrogen bond to stabilize formation of heterodimers (K370$E_{CH3A}$-E357$N_{CH3B}$, K370$E_{CH3A}$-S364$_{CH3B}$, Y349$_{CH3A}$-E357$N_{CH3B}$). In addition, when a CH3A domain homodimer was formed, the formation was inhibited by electrostatic repulsion (E357$_{CH3A}$-K370$E_{CH3A}$), and when a CH3B domain homodimer was formed, there was no remarkable repulsion, but the existing interaction that contributes to the formation of the homodimer was absent. As a result, the formation of heterodimer was more thermodynamically stable than the formation of homodimer, and thus the formation of heterodimer was preferred (FIG. 12A).

A108 [CH3A (K370E/K409W): CH3B (E357T/S364T/D399V/F405T)]

In the wild type CH3 domain interaction surface, K370 of one domain was adjacent to E357 and S364 of another domain. Among them, the electrostatic interaction between K370 and E357 of the other domain contributed to the dimer formation of the CH3 domain. In the A108 mutant selected from the LibA1 library, an electrostatic binding between the CH3A domain and the CH3B domain was substituted with an asymmetric electrostatic bond to stabilize formation of a heterodimer (K370$E_{CH3A}$-K409$_{CH3B}$). In addition, when a CH3A domain homodimer was formed, the formation was inhibited by electrostatic repulsion (E357$_{CH3A}$-K370E), and when a CH3B domain homodimer was formed, there was no remarkable repulsion, but the existing interaction that contributes to the formation of the homodimer was absent. As a result, the formation of heterodimer was more thermodynamically stable than the formation of homodimer, and thus the formation of heterodimer was preferred (FIG. 12B).

A109 [CH3A (K370M/K409W): CH3B (E357M/S364W/D399V/F405T)]

In the wild type CH3 domain interaction surface, K370 of one domain was adjacent to E357 and S364 of another domain. Among them, the electrostatic interaction between K370 and E357 of the other domain contributed to the dimer formation of the CH3 domain. In the A109 mutant selected from the LibA1 library, an electrostatic binding between the CH3A domain and the CH3B domain was substituted with a spatial complementary hydrophobic bond to stabilize formation of a heterodimer (K370$M_{CH3A}$-E357M/S364$W_{CH3B}$). In addition, when a CH3A domain homodimer was formed, a residue (E357) having a change that does not form a pair but exists alone, was present, and when a CH3B domain homodimer was formed, spacing within the CH3 domain interaction surface was difficult due to a side chain between adjacent residues (K370$_{CH3B}$-S364$W_{CH3B}$). As a result, the formation of the heterodimer was more thermodynamically stable than the formation of the homodimer, and thus the formation of heterodimer was preferred (FIG. 13A).

A146 [CH3A (K370D/K409W): CH3B (E357M/D399V/F405T)]

In the wild type CH3 domain interaction surface, K370 of one domain was adjacent to E357 and S364 of another domain. Among them, the electrostatic interaction between K370 and E357 of the other domain contributed to the dimer formation of the CH3 domain. In the A146 mutant selected from the LibA1 library, an electrostatic binding between the CH3A domain and the CH3B domain was substituted with an asymmetric electrostatic bond to stabilize formation of a heterodimer (K370$D_{CH3A}$-K409$_{CH3B}$). In addition, when a CH3A domain homodimer was formed, the formation was inhibited by electrostatic repulsion (E357$_{CH3A}$-K370$D_{CH3A}$), and when a CH3B domain homodimer was formed, there was no remarkable repulsion, but the existing interaction that contributes to the formation of the homodimer was absent. As a result, the formation of heterodimer was more thermodynamically stable than the formation of homodimer, and thus the formation of heterodimer was preferred (FIG. 13B).

B121 [CH3A (D399E/K409W): CH3B (K392E/D399V/F405T)]

In the wild type CH3 domain interaction surface, D399 of one domain was adjacent to K392 and K409 of another domain, and the electrostatic interaction between these residues contributed to the dimer formation of the CH3 domain. In the B121 mutant selected from the LibB1 library, an electrostatic binding between the CH3A domain and the CH3B domain was substituted with an asymmetric electrostatic bond to stabilize formation of a heterodimer (D399$E_{CH3A}$-K409$_{CH3B}$). In addition, when the CH3A domain homodimer was formed, the formation was inhibited by anionic-n repulsion (D399$E_{CH3A}$-K409$W_{CH3A}$), and when a CH3B domain homodimer was formed, residues (K392$E_{CH3B}$, K409$_{CH3B}$) having a change that does not form a pair but exists alone, was present. As a result, the formation of heterodimer was more thermodynamically stable than the formation of homodimer, and thus the formation of heterodimer was preferred (FIG. 14A).

B135 [CH3A (D399L/K409W): CH3B (K392S/K409L/D399V/F405T)]

In the wild type CH3 domain interaction surface, D399 of one domain was adjacent to K392 and K409 of another domain, and the electrostatic interaction between these residues contributed to the dimer formation of the CH3 domain. In the B135 mutant selected from the LibB1 library, an electrostatic binding between the CH3A domain and the CH3B domain was substituted with a spatial complementary hydrophobic bond to stabilize formation of a heterodimer (D399$L_{CH3A}$-K392S/K409$L_{CH3B}$). In addition, when a CH3A domain homodimer was formed, a residue (K392$_{CH3A}$) that does not form a pair but exists alone, was present, and when a CH3B domain homodimer was formed, a lack of inter-domain interaction (hole-hole interaction surface) caused when a residue including a side chain having a small size was positioned on the interaction surface, was observed. As a result, the formation of heterodimer was more thermodynamically stable than the formation of homodimer, and thus the formation of heterodimer was preferred (FIG. 14B).

B168 [CH3A (D399L/K409W): CH3B (K392G/K409M/D399V/F405T)]

In the wild type CH3 domain interaction surface, D399 of one domain was adjacent to K392 and K409 of another domain, and the electrostatic interaction between these residues contributed to the dimer formation of the CH3 domain. In the B168 mutant selected from the LibB1 library, an electrostatic binding between the CH3A domain and the CH3B domain was substituted with a spatial complementary hydrophobic bond to stabilize formation of a heterodimer (D399L$_{CH3A}$-K392G/K409M$_{CH3B}$). In addition, when a CH3A domain homodimer was formed, a residue (K392$_{CH3A}$) that does not form a pair but exists alone, was present, and when a CH3B domain homodimer was formed, a hole-hole interaction surface was observed. As a result, the formation of heterodimer was more thermodynamically stable than the formation of homodimer, and thus the formation of heterodimer was preferred (FIG. 15).

Example 7: Second Mutant Pair Combination Library Construction Strategy Based on Mutant Pairs Selected from LibA1 and LibB1 Libraries An additional secondary library was constructed to improve a heterodimer formation yield of the mutant pairs selected from the LibA1 and LibB1 libraries. FIG. 16 is a schematic diagram showing secondary library construction strategy based on A107$_{w/oW-VT}$ and B168$_{w/oW-VT}$ mutant pair having a high heterodimer formation yield without the W-VT mutation site confirmed in Example 5 above. As a site where the mutant pair was introduced, electrostatic pairs (E357/S364-K370 and K392/K409-D399) at the symmetrical position of two pairs of electrostatic bonding pairs, i.e., mutation sites included in the library constructed in Example 3, were selected. Specifically, the LibA2 library in which mutation was introduced into E357/S364$_{CH3A}$-K370$_{CH3B}$ site of A107$_{w/oW-VT}$ mutant (K370E$_{CH3A}$-E357N$_{CH3B}$) including the mutant pair selected from LibA1 and the LibB2 library in which mutation was introduced into K392/K409$_{CH3A}$-D399$_{CH3B}$ site of B168$_{w/oW-VT}$ mutant (D399L$_{CH3A}$-K392G/K409M$_{CH3B}$) were constructed. Here, the amino acid that was mutated at the mutation site was allowed to include NKK. NNK encoded N(N=A, T, C, G) for the first and second, and K(B=G, T) for the third, and thus it could be substituted with non-polar amino acid (Gly, Ala, Val, Leu, Ile, Phe, Tyr, Trp, Cys, Met) at a probability of 53.1%, uncharged/polar amino acid (Ser, Thr, Asn, Gln) at a probability of 21.9%, positive charge/negative charge amino acid (Asp, Glu, His, Lys, Arg) at a probability of 21.9%, and termination codon at a probability of 3.1%.

For production of the LibA2 library and the LibB2 library, a displayed Fc$_{CH3A}$ library including a CH3A domain mutant and a secreted Fc$_{CH3B}$ library including a CH3B domain mutant were first produced, and the library gene was amplified using primers shown in Table 8 below.

TABLE 8

Oligonucleotide sequence of primer used in constructing LibA1 library and LibB1 library

| Library | | Purpose | Direction | Length | Oligonucleotide Sequence (5'-3') |
|---|---|---|---|---|---|
| LibA2 | Displayed Fc$_{CH3A}$ (CH3A) | Amplifying Fc fragment 1 | Forward | 22 | GTTCCAGACTACGCTCTGCAGG (SEQ ID NO: 117) |
| | | Amplifying Fc fragment 1 | Reverse | 18 | ATCCCGGGATGGGGGCAG (SEQ ID 118) |
| | | Amplifying Fc fragment 2 | Forward | 63 | CTGCCCCCATCCCGGGATNNKCTGACCAAG AACCAGGTCNNKCTGACCTGCCTGGTCGAG GGC(SEQ ID NO: 119) |
| | | Amplifying Fc fragment 2 | Reverse | 35 | TCGATTTTGTTACATCTACACTGTT GTTATCAGAT (SEQ ID NO: 120) |
| | Secreted Fc$_{CH3B}$ (CH3B) | Amplifying Fc fragment 1 | Forward | 26 | CTCAACCGGTTATTTCTACTACCGTC (SEQ ID NO: 121) |
| | | Amplifying Fc fragment 1 | Reverse | 20 | GACCAGGCAGGTCAGGCTGA (SEQ ID NO: 122) |
| | | Amplifying Fc fragment 2 | Forward | 45 | TCAGCCTGACCTGCCTGGTCNNK GGCTTCTATCCCAGCGACATCG (SEQ ID NO: 123) |
| | | Amplifying Fc fragment 2 | Reverse | 33 | GAACAAAGTCGATTTTGTTACATCT ACACTGTT (SEQ ID NO: 124) |
| LibB2 | Displayed Fc$_{CH3A}$ (CH3A) | Amplifying Fc fragment 1 | Forward | 22 | GTTCCAGACTACGCTCTGCAGG (SEQ ID NO: 125) |
| | | Amplifying Fc fragment 1 | Reverse | 58 | AGGAGCCGTCGGACAACAGCACGGGAGGC GTGGTMNNGTAGTTGTTCTCCGGCTGCCC (SEQ ID NO: 126) |
| | | Amplifying Fc fragment 2 | Forward | 57 | CTGTTGTCCGACGGCTCCTTCTTCCTCTACA GCNNKCTCACCGTGGACAAGAGCAGG (SEQ ID NO: 127) |
| | | Amplifying Fc fragment 2 | Reverse | 35 | TCGATTTTGTTACATCTACACTGTTG TTATCAGAT (SEQ ID NO: 128) |

TABLE 8-continued

Oligonucleotide sequence of primer used in constructing LibA1 library and LibB1 library

| Library | Purpose | Direction | Length | Oligonucleotide Sequence (5'-3') |
|---|---|---|---|---|
| Secreted Fc$_{CH3B}$ (CH3B) | Amplifying Fc fragment 1 | Forward | 26 | CTCAACCGGTTATTTCTACTACCGTC (SEQ ID NO: 129) |
| | Amplifying Fc fragment 1 | Reverse | 18 | CAGCACGGGAGGCGTGGT (SEQ ID NO: 130) |
| | Amplifying Fc fragment 2 | Forward | 42 | ACCACGCCTCCCGTGCTGNNKTCCGACGGC TCCTTCTTCCTC (SEQ ID NO: 131) |
| | Amplifying Fc fragment 2 | Reverse | 33 | GAACAAAGTCGATTTTGTTACATCT ACACTGTT (SEQ ID NO: 132) |

A method for producing the haploid library of LibA2 and LibB2, and a method for producing the diploid library using the yeast mating were the same as described in Example 3. A size of the constructed diploid library was confirmed by measuring the number of colonies grown on the selective medium after stepwise dilution. LibA2 was produced to have a size of about 3.3×10$^7$ and LibB2 was produced to have a size of about 3.0×10$^7$, all of which exceeded the theoretical library size of 8×10$^3$.

Example 8: Selection of CH3 Domain Mutant Pair Inducing High Efficient Formation of Heterodimeric Heavy Chain Constant Region from Secondary Mutant Pair Combination Libraries LibA2 and LibB2

In order to select the mutant pair in which high efficient formation of the heterodimeric heavy chain constant region was induced from the libraries LibA2 and LibB2 constructed in Example 7 above, FACS was performed to suspend the yeast having a high degree of immobilization of secreted Fc$_{CH3B}$ on the surface of yeast cell. Specifically, the LibA2 and LibB2 libraries were allowed to express on the surface of the yeast cell, primarily bound with anti-Flag mouse mAb (F3165) (Sigma-Aldrich), and secondly reacted with anti-mouse antibody conjugated with PE (phycoerythrin conjugated anti-mouse mAb, sc-3738) (Santa Cruz Biotechnology), and then suspended using a FACS Aria II instrument (Becton & Dickinson). FACS was sequentially performed four times. FIG. 17A shows data obtained by comparison between mean fluorescence intensity measured from a PE signal value obtained by detecting secreted Fc$_{CH3B}$ immobilized on a surface of the yeast cell with respect to the suspended LibA2 and LibB2 libraries, and a PE signal value of the EW-RVT CH3 domain mutant pair (normalization of the mean fluorescence sensitivity of EW-RVT to 100%). Thus, suspension of the LibA2 and LibB2 libraries was confirmed. Clones having a high degree of immobilization of the secreted Fc$_{CH3B}$ on the yeast cell surface by the above-described screening were suspended to obtain individual clones. Four individual clones A205, A210, A216, and A241 were separated from the LibA2 library and six individual clones B212, B215, B235, B239, B240, and B256 were separated from the LibB2 library. The PE signal value obtained by detecting the secreted Fc$_{CH3B}$ of the selected individual clones was measured, and as a result, it was confirmed that the PE signal value was higher than that of the parent mutant pair, i.e., A107$_{w/oW-VT}$ and B168$_{w/oW-VT}$ (FIG. 6B). Sequences of CH3A and CH3B domain pairs of the individual clones selected from the LibA2 and LibB2 libraries were identified using a yeast colony PCR method, and the colony PCR method has been described in detail in an already published paper (Baek et al. 2014). Table 9 below summarizes the mutation pairs introduced into individual clones selected from the respective LibA2 and LibB2 libraries.

TABLE 9

Mutation pair introduced into individual clone selected from LibA2 and LibB2 libraries

| Mutant name | | CH3A | CH3B |
|---|---|---|---|
| LibA2 | A205 | E357D/S364W/K370E | E357N/K370R |
| | A210 | E357A/S364Y/K370E | E357N/K370H |
| | A216 | E357G/S364W/K370E | E357N |
| | A241 | E357N/S364W/K370E | E357N |
| LibB2 | B212 | K392I/D399L | D399G/K392G/K409M |
| | B215 | K392R/K409R/D399L | D399W/K392G/K409M |
| | B235 | K392C/D399L | D399C/K392G/K409M |
| | B239 | K392L/D399L | D399S/K392G/K409M |
| | B240 | K392S/K409R/D399L | D399G/K392G/K409M |
| | B256 | K392N/D399L | D399V/K392G/K409M |

Example 9: Evaluation of Heterodimeric Heavy Chain Constant Region Formation Ability of CH3 Domain Mutant Pair Selected from LibA2 and LibB2 Libraries A scFv-Fc$_{CH3A}$/Fc$_{CH3B}$ co-expression system was used to evaluate the heterodimer formation yield of the CH3 domain mutant selected in Example 8 above. The scFv-Fc$_{CH3A}$/Fc$_{CH3B}$ co-expression system is described in detail in Example 5 above. The CH3 domain mutant pair of the individual clones selected from the LibA2 and LibB2 libraries in Example 8 above was cloned into an animal cell expression vector so that the CH3A mutant was expressed into the scFv-Fc$_{CH3A}$ format and the CH3B mutant was expressed into the Fc$_{CH3B}$ format. Table 10 below shows constructed scFv-Fc$_{CH3A}$/Fc$_{CH3B}$ mutant pairs, which include CH3 domain mutant pairs of the individual clones selected in Example 8 above, wherein the EW-RVT and the A107$_{w/oW-VT}$, B168$_{w/oW-VT}$ mutant pairs were used as control groups.

TABLE 10

Mutant pair constructed for evaluation of heterodimer formation ability of mutant selected from LibA2 and LibB2 libraries

| Mutant name | | scFv-Fc$_{CH3A}$ (CH3A chain) | Fc$_{CH3B}$ (CH3B chain) |
|---|---|---|---|
| | EW-RVT | K360E/K409W | Q347R/D399V/F405T |
| LibA1 | A107$_{w/oW-VT}$ | K370E | E357N |
| LibA2 | A205 | E357D/S364W/K370E | E357N/K370R |
| | A210 | E357A/S364Y/K370E | E357N/K370H |

TABLE 10-continued

Mutant pair constructed for evaluation of heterodimer formation ability of mutant selected from LibA2 and LibB2 libraries

| Mutant name | | scFv-Fc$_{CH3A}$ (CH3A chain) | Fc$_{CH3B}$ (CH3B chain) |
|---|---|---|---|
| | A216 | E357G/S364W/K370E | E357N |
| | A241 | E357N/S364W/K370E | E357N |
| LibB1 | B168$_{w/oW-VT}$ | D399L | K392G/K409M |
| LibB2 | B212 | K392I/D399L | D399G/K392G/K409M |
| | B215 | K392R/K409R/D399L | D399W/K392G/K409M |
| | B235 | K392C/D399L | D399C/K392G/K409M |
| | B239 | K392L/D399L | D399S/K392G/K409M |
| | B240 | K392S/K409R/D399L | D399G/K392G/K409M |
| | B256 | K392N/D399L | D399V/K392G/K409M |

The expression and purification procedure of the scFv-Fc$_{CH3A}$/Fc$_{CH3B}$ heterodimer antibody using the HEK293-F system (Invitrogen) are the same as described in Example 5. The purified antibody was quantified by BCA technique. FIG. 18A shows data obtained by analyzing 5 μg of the purified antibody on SDS-PAGE under 12% non-reducing conditions. The scFv-Fc$_{CH3A}$ homodimer was observed at 103 kDa, the Fc$_{CH3B}$ homodimer was observed at 53 kDa, the Fc$_{CH3B}$ monomer was observed at 25 kDa, and the scFv-Fc$_{CH3A}$/Fc$_{CH3B}$ heterodimer was observed at 78 kDa. It was confirmed that the selected clones had high heterodimer formation ability as compared with the parent mutant pair, i.e., A107$_{w/oW-VT}$ and B168$_{w/oW-VT}$. It was confirmed that among the mutants selected from the library LibA2, the A205 had a high heterodimer formation yield of about 89%, and among the mutants selected from the library LibB2, the B235 had a high heterodimer formation yield of about 89%.

FIG. 18B and Table 11 show quantitative data showing the heterodimer formation yield obtained by repeatedly expressing and purifying the scFv-Fc$_{CH3A}$/Fc$_{CH3B}$ heterodimer of Table 10 above, then analyzing each band density on the SDS-PAGE by using Image J (Wayne Rasband, NIH) program. The EW-RVT and A107$_{w/oW-VT}$, B168$_{w/oW-VT}$ mutant pairs were used as control groups. The result values were expressed as mean±standard deviation after three independent experiments were performed. It was also confirmed that heterodimer formation of the A205 and B235 variant pairs having high heterodimer formation yield among the selected individual clones was affected by a molar ratio of the pcDNA3.1(+)-scFv-Fc$_{CH3A}$ and pcDNA3.1(+)-Fc$_{CH3B}$ plasmids added at the transfection (FIG. 19).

TABLE 11

Heterodimer formation yield of mutant selected from secondary libraries (LibA2 and LibB2) (SDS-PAGE analysis result)

| Mutant name | | (scFv-Fc)$_2$ (homodimer)(%) | (scFv-Fc)(Fc) (heterodimer)(%) | (FC)$_2$ (homodimer)(%) | Fc monomer (%) |
|---|---|---|---|---|---|
| | EW-RVT | 0.5 ± 0.6 | 91.4 ± 1.2 | 1.6 ± 0.6 | 6.6 ± 1.3 |
| LibA1 | A107$_{w/oW-VT}$ | 21.3 ± 0.4 | 78.2 ± 4.2 | 0.5 ± 2.3 | ND |
| LibA2 | A205 | 1.0 ± 0.1 | 88.8 ± 2.2 | 10.2 ± 2.3 | ND |
| | A210 | 9.9 ± 6.9 | 80.8 ± 5.8 | 9.3 ± 2.9 | ND |
| | A216 | 1.5 ± 0.4 | 80.3 ± 4.6 | 18.2 ± 2.7 | ND |
| | A241 | 15.7 ± 3.0 | 81.0 ± 3.9 | 3.3 ± 0.8 | ND |
| LibB1 | B168$_{w/oW-VT}$ | 1.5 ± 0.8 | 60.9 ± 2.4 | 37.6 ± 2.6 | ND |
| LibB2 | B212 | 0.9 ± 0.7 | 65.3 ± 4.3 | 33.8 ± 4.1 | ND |
| | B215 | 1.9 ± 1.2 | 78.1 ± 6.9 | 20.0 ± 5.6 | ND |
| | B235 | 3.7 ± 1.0 | 89.4 ± 4.1 | 6.9 ± 2.0 | ND |
| | B239 | 3.4 ± 1.6 | 76.3 ± 6.8 | 20.3 ± 5.2 | ND |
| | B240 | 4.8 ± 1.4 | 83.3 ± 4.7 | 11.9 ± 3.2 | ND |
| | B256 | 3.9 ± 1.4 | 79.4 ± 5.2 | 16.7 ± 3.7 | ND |

Table 12 below shows purification yield of mutants selected from the secondary libraries, LibA2 and LibB2. The yield when the heterodimers described in Table 10 were expressed and purified by the above-described method was calculated by normalizing a purification yield of the heterodimer having the EW-RVT mutant pair as the control group as 100%. The purification yield of EW-RVT heterodimer was 3.1±0.7 mg/transfection 100 ml in HEK293-F cell. The heterodimer heavy chain constant region was repeatedly expressed and purified three or more times to obtain mean±standard deviation. As a result, the heterodimer including the heavy chain constant region mutant had a similar yield to that of the control group. Thus, it was determined that the introduction of the mutant pair selected through the library did not significantly impair the stability of the heavy chain constant region protein.

TABLE 12

Purification yield of mutant selected from secondary libraries (LibA2 and LiB2) (HEK293-F cells, about 6 days expression, and 3.1 ± 0.7 mg/100 ml culture volume for EW-RVT mutant)

| Mutant name | | Final product after buffer change [normalization with yield of EW-RVT mutant] [%] |
|---|---|---|
| EW-RVT | | 100 |
| LibA2 | A205 | 118 ± 5.0 |
| | A210 | 104 ± 9.2 |
| | A216 | 92.1 ± 13.1 |
| | A241 | 150 ± 49.6 |
| LibB2 | B212 | 123 ± 31.2 |
| | B215 | 114 ± 12.9 |
| | B235 | 101 ± 25.3 |
| | B239 | 93.8 ± 31.2 |
| | B240 | 104 ± 16.9 |
| | B256 | 103 ± 11.8 |

Example 10: Structural Analysis of CH3 Domain Mutant Pair Selected from LibA2 and LibB2 Libraries To confirm the reason that the heterodimer formation of the CH3 domain mutant pair selected through the LibA2 and LibB2 libraries was preferred, the CH3 domain interaction surface was modeled and analyzed by using the protein structure of the known CH3 domain mutant pair EW-RVT (Choi et al., 2015).

A205 [CH3A (E357D/S364W/K370E): CH3B (E357N/K370R)]

In the wild type CH3 domain interaction surface, E357 and S364 of one domain were adjacent to K370 of another domain. Among them, the electrostatic interaction between E357 and K370 of the other domain contributed to the dimer formation of the CH3 domain. In the A205 variant selected from the LibA2 library, an electrostatic binding between the CH3A domain and the CH3B domain is substituted with a cation-π bond to stabilize the formation of a heterodimer ($S364W_{CH3A}$-$K370R_{CH3B}$). In addition, when a CH3A domain homodimer was formed, the formation was inhibited by an anion-π repulsion ($E357D_{CH3A}$-$S364W_{CH3A}$), and when a CH3B domain homodimer was formed, a hole-hole interaction surface was observed. As a result, the formation of heterodimer was more thermodynamically stable than the formation of homodimer, and thus the formation of heterodimer was preferred (FIG. 20A).

A210 [CH3A (E357A/S364Y/K370E): CH3B (E357N/K370H)]

In the wild type CH3 domain interaction surface, E357 and S364 of one domain were adjacent to K370 of another domain. Among them, the electrostatic interaction between E357 and K370 of the other domain contributes to the dimer formation of the CH3 domain. In the A210 mutant selected from the LibA2 library, an electrostatic binding between the CH3A domain and the CH3B domain is substituted with a π-π bond to stabilize the formation of a heterodimer ($S364Y_{CH3A}$-$K370H_{CH3B}$) In addition, when a CH3A domain homodimer was formed, the formation was inhibited by an anion-π repulsion ($S364Y_{CH3A}$-$K370E_{CH3A}$), and when a CH3B domain homodimer was formed, a hole-hole interaction surface was observed. As a result, the formation of heterodimer was more thermodynamically stable than the formation of the homodimer, and thus the formation of the heterodimer was preferred (FIG. 20B).

A216 [CH3A (E357G/S364W/K370E): CH3B (E357N)]

In the wild type CH3 domain interaction surface, E357 and S364 of one domain were adjacent to K370 of another domain. Among them, the electrostatic interaction between E357 and K370 of the other domain contributes to the dimer formation of the CH3 domain. In the A216 mutant selected from the LibA2 library, an electrostatic binding between the CH3A domain and the CH3B domain is substituted with a cation-π bond to stabilize the formation of a heterodimer ($S364W_{CH3A}$-$K370R_{CH3B}$). In addition, when a CH3A domain homodimer was formed, the formation was inhibited by an anion-π repulsion ($S364W_{CH3A}$-$K370E_{CH3A}$) and when a CH3B domain homodimer was formed, there was no remarkable repulsion, but the existing interaction that contributes to the formation of the homodimer was absent. As a result, the formation of heterodimer was more thermodynamically stable than the formation of homodimer, and thus the formation of heterodimer was preferred (FIG. 21A).

A241 [CH3A (E357N/S364W/K370E): CH3B (E357N)]

In the wild type CH3 domain interaction surface, E357 and S364 of one domain were adjacent to K370 of another domain. Among them, the electrostatic interaction between E357 and K370 of the other domain contributes to the dimer formation of the CH3 domain. In the A241 mutant selected from the LibA2 library, an electrostatic binding between the CH3A domain and the CH3B domain is substituted with a cation-π bond to stabilize the formation of a heterodimer ($S364W_{CH3A}$-$K370_{CH3B}$). In addition, when a CH3A domain homodimer was formed, the formation was inhibited by an anion-π repulsion ($S364W_{CH3A}$-$K370E_{CH3A}$) and when a CH3B domain homodimer was formed, there was no remarkable repulsion, but the existing interaction that contributes to the formation of the homodimer was absent. As a result, the formation of heterodimer was more thermodynamically stable than the formation of homodimer, and thus the formation of heterodimer was preferred (FIG. 21B).

B212 [CH3A (K392I/D399L): CH3B (D399G/K392G/K409M)]

In the wild type CH3 domain interaction surface, K392 and K409 of one domain were adjacent to D399 of another domain, and the electrostatic interaction between these residues contributed to the dimer formation of the CH3 domain. In the B212 mutant selected from the LibB2 library, an electrostatic binding between the CH3A domain and the CH3B domain was substituted with a cation-π bond to stabilize the formation of a heterodimer ($K409_{CH3A}$-$F405_{CH3B}$). In addition, when a CH3A domain homodimer was formed, a residue ($K409_{CH3A}$) that does not form a pair but exists alone, was present, and when a CH3B domain homodimer is formed, a hole-hole interaction surface was observed. As a result, the formation of heterodimer was more thermodynamically stable than the formation of homodimer, and thus the formation of heterodimer was preferred (FIG. 22A).

B215 [CH3A (K392R/K409R/D399L): CH3B (D399W/K392G/K409M)]

In the wild type CH3 domain interaction surface, K392 and K409 of one domain were adjacent to D399 of another domain, and the electrostatic interaction between these residues contributed to the dimer formation of the CH3 domain. In the B215 mutant selected from the LibB2 library, an electrostatic binding between the CH3A domain and the CH3B domain was substituted with a cation-π bond to stabilize the formation of heterodimers ($K392R_{CH3A}$-$D399W_{CH3B}$, $K409R_{CH3A}$-$D399W_{CH3B}$). In addition, when the CH3A domain homodimer is formed, residues ($K392R_{CH3A}$, $K409_{CH3A}$) having a change that does not form a pair but exists alone were present, and spacing within the CH3 domain interaction surface is difficult due to a side chain between adjacent residues ($K409M_{CH3B}$-$D399W_{CH3B}$). As a result, the formation of heterodimer was more thermodynamically stable than the formation of homodimer, and thus the formation of heterodimer was preferred (FIG. 22B).

B235 [CH3A (K392C/D399L): CH3B (D399C/K392G/K409M)]

In the wild type CH3 domain interaction surface, K392 and K409 of one domain were adjacent to D399 of another domain, and the electrostatic interaction between these residues contributed to the dimer formation of the CH3 domain. In the B235 variant selected from the LibB2 library, an electrostatic binding between the CH3A domain and the CH3B domain is substituted with a disulfide bond to stabilize formation of a heterodimer ($K392C_{CH3A}$-$D399C_{CH3B}$). In addition, when a CH3A domain homodimer was formed, a residue ($K409_{CH3A}$) that does not form a pair but exists alone, was present, and when a CH3B domain homodimer is formed, a hole-hole interaction surface was observed. As a result, the formation of the heterodimer was more thermodynamically stable than the formation of the homodimer, and thus the formation of the heterodimer was preferred (FIG. 23A).

B239 [CH3A (K392L/D399L): CH3B (D399S/K392G/K409M)]

In the wild type CH3 domain interaction surface, K392 and K409 of one domain were adjacent to D399 of another domain, and the electrostatic interaction between these residues contributed to the dimer formation of the CH3 domain. In the B239 mutant selected from the LibB2 library, an electrostatic binding between the CH3A domain and the CH3B domain was substituted with a cation-π bond to stabilize the formation of a heterodimer ($K409_{CH3A}$-$F405_{CH3B}$). In addition, when a CH3A domain homodimer was formed, a residue ($K409_{CH3A}$) that does not form a pair but exists alone, was present, and when a CH3B domain homodimer is formed, a hole-hole interaction surface was observed. As a result, the formation of heterodimer was more thermodynamically stable than the formation of homodimer, and thus the formation of heterodimer was preferred (FIG. 23B).

B240 [CH3A (K392S/K409R/D399L): CH3B (D399G/K392G/K409M)]

In the wild type CH3 domain interaction surface, K392 and K409 of one domain were adjacent to D399 of another domain, and the electrostatic interaction between these residues contributed to the dimer formation of the CH3 domain. In the B240 mutant selected from the LibB2 library, an electrostatic binding between the CH3A domain and the CH3B domain was substituted with a cation-π bond to stabilize the formation of a heterodimer ($K409_{CH3A}$-$F405_{CH3B}$). In addition, when a CH3A domain homodimer was formed, a residue ($K409_{CH3A}$) that does not form a pair but exists alone, was present, and when a CH3B domain homodimer is formed, a hole-hole interaction surface was observed. As a result, the formation of heterodimer was more thermodynamically stable than the formation of homodimer, and thus the formation of heterodimer was preferred (FIG. 24A).

B256 [CH3A (K392N/D399L): CH3B (D399V/K392G/K409M)]

In the wild type CH3 domain interaction surface, K392 and K409 of one domain were adjacent to D399 of another domain, and the electrostatic interaction between these residues contributed to the dimer formation of the CH3 domain. In the B256 mutant selected from the LibB2 library, an electrostatic binding between the CH3A domain and the CH3B domain was substituted with a cation-π bond to stabilize the formation of a heterodimer ($K409_{CH3A}$-$F405_{CH3B}$). In addition, when a CH3A domain homodimer was formed, a residue ($K409_{CH3A}$) that does not form a pair but exists alone, was present, and when a CH3B domain homodimer is formed, a hole-hole interaction surface was observed. As a result, the formation of heterodimer was more thermodynamically stable than the formation of homodimer, and thus the formation of heterodimer was preferred (FIG. 24B).

Example 11: Expression and Purification of Selected Mutant Pairs Selected from CH3 Domain Mutant Pair Library In order to analyze biochemical properties of four kinds of mutant pairs (A107, B168, A205, and B235) having a high heterodimer formation yield in each individual clone selected from the above-constructed four CH3 domain mutant pair combination libraries (LibA1, LibB1, LibA2 and LibB2), the mutant pairs were produced into a heavy chain constant region dimer format ($Fc_{CH3A}$-$Fc_{CH3B}$). Table 13 below shows sequences of mutant pairs produced into the heavy chain constant region dimer format. To this end, each CH3A domain mutant and CH3B domain mutant were cloned into the pcDNA3.1(+)-$Fc_{CH3}$ vector described in Example 5.

TABLE 13

| | Mutant pair produced into heavy chain constant region dimer format | |
|---|---|---|
| Mutant name | $Fc_{CH3A}$ (CH3A chain) | $Fc_{CH3B}$ (CH3B chain) |
| Fc-A107 | K370E/K409W | E357N/D399V/F405T |
| Fc-B168 | D399L/K409W | K392G/K409M/D399V/F405T |
| Fc-A205 | E357D/S364W/K370E | E357N/K370R |
| Fc-B235 | K392C/D399L | D399C/K392G/K409M |

FIG. 25 schematically shows $Fc_{CH3A}$-$Fc_{CH3B}$ format including the mutant pair used in the analysis. The constructed pcDNA3.1 (+)-$Fc_{CH3A}$ and pcDNA3.1 (+)-$Fc_{CH3B}$ animal cell expression vectors were produced using the HEK293-F system (Invitrogen). Specifically, a mixture of an expression vector and polyethylenimine (PEI) (Polyscience) was transfected into HEK293-F cells (Invitrogen) that were suspension-grown on a serum-free FreeStyle 293 expression medium (Invitrogen) in a shaking flask (Corning). When transfecting 200 m of the mixture in the shaking flask, HEK293-F cells were seeded at a density of $2.0 \times 10^6$ cell/ml in 100 ml of medium and cultured at 125 rpm and 8% $CO_2$. The pcDNA3.1(+)-scFv-$Fc_{CH3A}$ and pcDNA3.1(+)-$Fc_{CH3B}$ plasmid DNA that were constructed as above at the same molar ratio were diluted in a FreeStyle 293 expression medium (Invitrogen) to a total of 250 μg (each DNA 1.25 μg/ml), and mixed with 5 ml of medium in which PEI 750 μg (7.5 μg/ml) was diluted, and then reacted at room temperature for 10 minutes. Then, the reacted mixed medium was put into cells that had been previously seeded with 100 ml and incubated at 125 rpm, 8% $CO_2$ for 4 hours. Then, the remaining 100 ml of FreeStyle 293 expression medium (Invitrogen) was added and the medium was incubated for 5 days. The cell culture supernatant collected with reference to the standard protocol was applied to Protein A Sepharose column (GE healthcare), and washed with PBS (pH 7.4). The heavy chain constant region mutant was eluted at pH 3.0 with 0.1 M glycine buffer and immediately neutralized with 1 M Tris buffer. The eluted protein fraction was concentrated using an Amicon Ultra (MILLIPORE) centrifugal concentrator after the buffer was exchanged with PBS (pH 7.4) using a Dextran Desalting Column (Thermo Scientific Pierce). The purified heavy chain constant region mutant was quantified by BCA technique.

FIG. 26 shows data obtained by analyzing 5 μg of the purified heavy chain constant region dimer protein on SDS-PAGE under 12% non-reducing conditions and reducing conditions. The purified heavy chain constant region mutant had a molecular weight of about 53 kDa under non-reducing conditions and a molecular weight of about 26 kDa under reducing conditions. This shows that the expressed purified heavy chain constant region mutant is present as the dimer through natural disulfide bond in solution and do not form an oligomer.

FIG. 27 shows results of HPLC (High Performance Liquid Chromatography) (Agilent 1200 Series LC Systems and Modules, Agilent) analysis using a size exclusion chromatography column (Superdex™ 200 10/300GC, GE Healthcare) in order to confirm that the purified heavy chain constant region mutant does not form an oligomer but is present as the dimer. An elution buffer was PBS (pH 7.4) and a flow rate was 0.5 ml/min. Proteins used as protein size markers were alcohol dehydrogenase (150 kDa), bovine serum albumin (66 kDa), and cytochrome C (12.4 kDa) (Sigma-Aldrich). In the heavy chain constant region mutant including all CH3 mutant pairs, one pole was measured at about 53 kDa, the size of the heavy chain constant region dimer protein, which showed that the mutant was present as the dimer without oligomer formation.

Example 12: Evaluation of Thermodynamic Stability of CH3 Domain Mutant Pair Selected from CH3 Domain Mutant Pair Library In order to evaluate thermodynamic stability of the heavy chain constant region mutants including four kinds of mutant pairs (A107, B168, A205, and B235) produced in Example 11, a maximum heat capacity temperature ($T_m$) was analyzed using a differential scanning calorimetry (DSC), MicroCal VP-DSC microcalorimeter (MicroCal, UK). Thermodynamic denaturation was measured at a rate of 1.5° C./min from 25° C. to 95° C., and the measured values were corrected through a buffer solution having the same composition except for the heavy chain constant region mutant. The maximum heat capacity temperature of the heavy chain constant region mutant was obtained by conversion after measuring a temperature of the maximal heat capacity at constant pressure ($\Delta C_p$). FIG. 28 and Table 14 show results of differential scanning calorimetry (DSC) analysis of the wild type heavy chain constant region and the Fc-A107, Fc-B168, Fc-A205, and Fc-B235 heavy chain constant region mutants, each including the mutant pair selected from the library, and show the maximum heat capacity temperature of the CH2 domain and the CH3 domain.

TABLE 14

Maximum heat capacity temperature of mutant pair produced into heavy chain constant region dimer format

| Fc proteins | $T_m$ (CH2 Domain )(° C.) | $T_m$ (CH3 Domain )(° C.) |
|---|---|---|
| Fc-WT | 71.3 ± 0.9 | 85.3 ± 0.4 |
| Fc-A107 | 72.4 ± 0.4 | 76.9 ± 0.5 |
| Fc-B168 | 71.5 ± 0.1 | 75.6 ± 0.4 |
| Fc-A205 | 72.2 ± 0.6 | 79.5 ± 1.0 |
| Fc-B235 | 73.1 ± 0.1 | 79.7 ± 0.7 |

The maximum heat capacity temperature of the CH2 domain of the wild type heavy chain constant region and the four heavy chain constant region mutants were similar to each other, but it was confirmed that regarding the maximum heat capacity temperature of the CH3 domain, the Fc-A205 (about 79.5° C.) and the Fc-B235 (about 76.9° C.) selected from the secondary library were higher than the Fc-A107 (about 76.9° C.) and the Fc-B168 (about 75.6° C.) selected from the primary library, and the known CH3 domain mutants, Fc-EW-RVT (about 77.4° C.) (Choi et al., 2013; Choi et al., 2015), and Fc-KiH (about 76.2° C.) (Choi et al., 2013; Atwell et al., 1997). It means that the mutants selected from the library retain thermodynamic stability, despite the introduction of mutation.

Example 13: Evaluation of FcRn Binding Ability of CH3 Domain Mutant Pair Selected from CH3 Domain Mutant Pair Library In order to confirm whether the heavy chain constant region mutants including the four kinds of mutant pairs (A107, B168, A205, B235) produced in Example 11 retain the binding ability to FcRn as they are as compared to the wild type heavy chain constant region, SPR (surface plasmon resonance) analysis was performed. The analysis was performed using a Biacore 2000 instrument (GE healthcare). Specifically, FcRn (Feng et al., 2011) was diluted in about 10 mM Na-acetate buffer (pH 4.0) and immobilized in 1000 response units (RU) on a CM5 sensor chip (GE healthcare). Binding and dissociation analyses were performed for 3 minutes, respectively, at a flow rate of 30 µl/min using PBS (pH 6.0) buffer or HBS-EP buffer (pH 7.4) containing 0.005% Tween 20, and the wild type heavy chain constant region and the four kinds of heavy chain constant region mutants were analyzed at concentrations of 312.5 nM, 0.625 µM, 1.25 µM, 2.5 µM and 5 µM. After the binding and dissociation analyses, regeneration of the CM5 sensor chip was performed for 1.5 minutes with a regeneration buffer (10 mM NaOH, 1 M NaCl, pH 10.0) at a flow rate of 30 µl/min. FIG. 29 shows the sensorgram obtained after the binding and dissociation analyses, and Table 15 below shows affinity calculated by using the obtained sensorgram. As a result, it was confirmed that the heavy chain constant region mutant including the mutant pair selected from the library retained a pH-dependent FcRn binding ability, which is similar to the wild type heavy chain constant region.

TABLE 15

Affinity for FcRn of mutant pair produced in heavy chain constant region dimer format (pH 6.0 condition)

| Fc proteins | $k_{on}$ (M$^{-1}$s$^{-1}$) | $k_{off}$ (s$^{-1}$) | $K_D$ (M) |
|---|---|---|---|
| Fc-WT | 1.64 ± 0.05 × 10$^3$ | 5.83 ± 0.46 × 10$^{-5}$ | 3.56 ± 0.39 × 10$^{-8}$ |
| Fc-A107 | 1.58 ± 0.03 × 10$^3$ | 1.02 ± 0.69 × 10$^{-4}$ | 6.50 ± 0.45 × 10$^{-8}$ |
| Fc-B168 | 1.09 ± 0.01 × 10$^3$ | 1.67 ± 0.39 × 10$^{-5}$ | 1.75 ± 0.15 × 10$^{-8}$ |
| Fc-A205 | 1.13 ± 0.01 × 10$^3$ | 1.11 ± 0.57 × 10$^{-4}$ | 1.18 ± 0.39 × 10$^{-8}$ |
| Fc-B235 | 1.58 ± 0.02 × 10$^3$ | 8.00 ± 0.57 × 10$^{-5}$ | 5.06 ± 0.43 × 10$^{-8}$ |

Table 16 and Table 17 below show sequence information of the heterodimer and the heterodimeric heavy constant region pair of the CH3 domain of the present disclosure

TABLE 16

Sequence information of heterodimer pair of CH3 domain

| Mutant name | CH3A (EU numbering 341~447) | CH3B (EU numbering 341~447) |
|---|---|---|
| Wild type | (EU number 341) GQPREPQVYTLPPSRDELTKNQVSL TCLVKGFYPSDIAVEWESNGQPENN YKTTPPVLDSDGSFFLYSKLTVDKS | Same as Wild type CH3A |

TABLE 16-continued

Sequence information of heterodimer pair of CH3 domain

| Mutant name | CH3A (EU numbering 341~447) | CH3B (EU numbering 341~447) |
|---|---|---|
| | RWQQGNVFSCSVMHEALHNHYTQKS<br>LSLSPGK<br>(EU number 447)<br>(SEQ ID NO: 1) | |
| W-VT | (EU number 341)<br>GQPREPQVYTLPPSRDELTKNQVSL<br>TCLVKGFYPSDIAVEWESNGQPENN<br>YKTTPPVLDSDGSFFLYSWLTVDKS<br>RWQQGNVFSCSVMHEALHNHYTQKS<br>LSLSPGK<br>(EU number 447)<br>(SEQ ID NO: 2) | (EU number 341)<br>GQPREPQVYTLPPSRDELTKNQVSLT<br>CLVKGFYPSDIAVEWESNGQPENNYK<br>TTPPVLVSDGSFTLYSKLTVDKSRWQ<br>QGNVFSCSVMHEALHNHYTQKSLSLS<br>PGK<br>(EU number 447)<br>(SEQ ID NO: 3) |
| EW-RVT | (EU number 341)<br>GQPREPQVYTLPPSRDELTENQVSL<br>TCLVKGFYPSDIAVEWESNGQPENN<br>YKTTPPVLDSDGSFFLYSWLTVDKS<br>RWQQGNVFSCSVMHEALHNHYTQKS<br>LSLSPGK<br>(EU number 447)<br>(SEQ ID NO: 4) | (EU number 341)<br>GQPREPRVYTLPPSRDELTKNQVSLT<br>CLVKGFYPSDIAVEWESNGQPENNYK<br>TTPPVLVSDGSFTLYSKLTVDKSRWQ<br>QGNVFSCSVMHEALHNHYTQKSLSLS<br>PGK<br>(EU number 447)<br>(SEQ ID NO: 5) |
| A107 | (EU number 341)<br>GQPREPQVYTLPPSRDELTKNQVSL<br>TCLVEGFYPSDIAVEWESNGQPENN<br>YKTTPPVLDSDGSFFLYSWLTVDKS<br>RWQQGNVFSCSVMHEALHNHYTQKS<br>LSLSPGK<br>(EU number 447)<br>(SEQ ID NO: 6) | (EU number 341)<br>GQPREPQVYTLPPSRDNLTKNQVSLT<br>CLVKGFYPSDIAVEWESNGQPENNYK<br>TTPPVLVSDGSFTLYSKLTVDKSRWQ<br>QGNVFSCSVMHEALHNHYTQKSLSLS<br>PGK<br>(EU number 447)<br>(SEQ ID NO: 7) |
| A108 | (EU number 341)<br>GQPREPQVYTLPPSRDELTKNQVSL<br>TCLVEGFYPSDIAVEWESNGQPENN<br>YKTTPPVLDSDGSFFLYSWLTVDKS<br>RWQQGNVFSCSVMHEALHNHYTQKS<br>LSLSPGK<br>(EU number 447)<br>(SEQ ID NO: 8) | (EU number 341)<br>GQPREPQVYTLPPSRDILTKNQVTLT<br>CLVKGFYPSDIAVEWESNGQPENNYK<br>TTPPVLVSDGSFTLYSKLTVDKSRWQ<br>QGNVFSCSVMHEALHNHYTQKSLSLS<br>PGK<br>(EU number 447)<br>(SEQ ID NO: 9) |
| A109 | (EU number 341)<br>GQPREPQVYTLPPSRDELTKNQVSL<br>TCLVMGFYPSDIAVEWESNGQPENN<br>YKTTPPVLDSDGSFFLYSWLTVDKS<br>RWQQGNVFSCSVMHEALHNHYTQKS<br>LSLSPGK<br>(EU number 447)<br>(SEQ ID NO: 10) | (EU number 341)<br>GQPREPQVYTLPPSRDMLTKNQVWLT<br>CLVKGFYPSDIAVEWESNGQPENNYK<br>TTPPVLVSDGSFTLYSKLTVDKSRWQ<br>QGNVFSCSVMHEALHNHYTQKSLSLS<br>PGK<br>(EU number 447)<br>(SEQ ID NO: 11) |
| A146 | (EU number 341)<br>GQPREPQVYTLPPSRDELTKNQVSL<br>TCLVDGFYPSDIAVEWESNGQPENN<br>YKTTPPVLDSDGSFFLYSWLTVDKS<br>RWQQGNVFSCSVMHEALHNHYTQKS<br>LSLSPGK<br>(EU number 447)<br>(SEQ ID NO: 12) | (EU number 341)<br>GQPREPQVYTLPPSRDMLTKNQVSLT<br>CLVKGFYPSDIAVEWESNGQPENNYK<br>TTPPVLVSDGSFTLYSKLTVDKSRWQ<br>QGNVFSCSVMHEALHNHYTQKSLSLS<br>PGK<br>(EU number 447)<br>(SEQ ID NO: 13) |
| B121 | (EU number 341)<br>GQPREPQVYTLPPSRDELTKNQVSL<br>TCLVKGFYPSDIAVEWESNGQPENN<br>YKTTPPVLESDGSFFLYSWLTVDKS<br>RWQQGNVFSCSVMHEALHNHYTQKS<br>LSLSPGK<br>(EU number 447)<br>(SEQ ID NO: 14) | (EU number 341)<br>GQPREPQVYTLPPSRDELTKNQVSLT<br>CLVKGFYPSDIAVEWESNGQPENNYE<br>TTPPVLVSDGSFTLYSKLTVDKSRWQ<br>QGNVFSCSVMHEALHNHYTQKSLSLS<br>PGK<br>(EU number 447)<br>(SEQ ID NO: 15) |
| B135 | (EU number 341)<br>GQPREPQVYTLPPSRDELTKNQVSL<br>TCLVKGFYPSDIAVEWESNGQPENN<br>YKTTPPVLLSDGSFFLYSWLTVDKS<br>RWQQGNVFSCSVMHEALHNHYTQKS<br>LSLSPGK<br>(EU number 447)<br>(SEQ ID NO: 16) | (EU number 341)<br>GQPREPQVYTLPPSRDELTKNQVSLT<br>CLVKGFYPSDIAVEWESNGQPENNYS<br>TTPPVLVSDGSFTLYSLLTVDKSRWQ<br>QGNVFSCSVMHEALHNHYTQKSLSLS<br>PGK<br>(EU number 447)<br>(SEQ ID NO: 17) |

TABLE 16-continued

Sequence information of heterodimer pair of CH3 domain

| Mutant name | CH3A (EU numbering 341~447) | CH3B (EU numbering 341~447) |
|---|---|---|
| B168 | (EU number 341)<br>GQPREPQVYTLPPSRDELTKNQVSL<br>TCLVKGFYPSDIAVEWESNGQPENN<br>YKTTPPVLLSDGSFFLYSWLTVDKS<br>RWQQGNVFSCSVMHEALHNHYTQKS<br>LSLSPGK<br>(EU number 447)<br>(SEQ ID NO: 18) | (EU number 341)<br>GQPREPQVYTLPPSRDELTKNQVSLT<br>CLVKGFYPSDIAVEWESNGQPENNYK<br>TTPPVLVSDGSFTLYSMLTVDKSRWQ<br>QGNVFSCSVMHEALHNHYTQKSLSLS<br>PGK<br>(EU number 447)<br>(SEQ ID NO: 19) |
| A205 | (EU number 341)<br>GQPREPQVYTLPPSRDDLTKNQVWL<br>TCLVEGFYPSDIAVEWESNGQPENN<br>YKTTPPVLDSDGSFFLYSKLTVDKS<br>RWQQGNVFSCSVMHEALHNHYTQKS<br>LSLSPGK<br>(EU number 447)<br>(SEQ ID NO: 20) | (EU number 341)<br>GQPREPQVYTLPPSRDNLTKNQVSLT<br>CLVRGFYPSDIAVEWESNGQPENNYK<br>TTPPVLDSDGSFFLYSKLTVDKSRWQ<br>QGNVFSCSVMHEALHNHYTQKSLSLS<br>PGK<br>(EU number 447)<br>(SEQ ID NO: 21) |
| A210 | (EU number 341)<br>GQPREPQVYTLPPSRDALTKNQVYL<br>TCLVEGFYPSDIAVEWESNGQPENN<br>YKTTPPVLDSDGSFFLYSKLTVDKS<br>RWQQGNVFSCSVMHEALHNHYTQKS<br>LSLSPGK<br>(EU number 447)<br>(SEQ ID NO: 22) | (EU number 341)<br>GQPREPQVYTLPPSRDNLTKNQVSLT<br>CLVHGFYPSDIAVEWESNGQPENNYK<br>TTPPVLDSDGSFFLYSKLTVDKSRWQ<br>QGNVFSCSVMHEALHNHYTQKSLSLS<br>PGK<br>(EU number 447)<br>(SEQ ID NO: 23) |
| A216 | (EU number 341)<br>GQPREPQVYTLPPSRDGLTKNQVWL<br>TCLVEGFYPSDIAVEWESNGQPENN<br>YKTTPPVLDSDGSFFLYSKLTVDKS<br>RWQQGNVFSCSVMHEALHNHYTQKS<br>LSLSPGK<br>(EU number 447)<br>(SEQ ID NO: 24) | (EU number 341)<br>GQPREPQVYTLPPSRDNLTKNQVSLT<br>CLVKGFYPSDIAVEWESNGQPENNYK<br>TTPPVLDSDGSFFLYSKLTVDKSRWQ<br>QGNVFSCSVMHEALHNHYTQKSLSLS<br>PGK<br>(EU number 447)<br>(SEQ ID NO: 25) |
| A241 | (EU number 341)<br>GQPREPQVYTLPPSRDNLTKNQVWL<br>TCLVEGFYPSDIAVEWESNGQPENN<br>YKTTPPVLDSDGSFFLYSKLTVDKS<br>RWQQGNVFSCSVMHEALHNHYTQKS<br>LSLSPGK<br>(EU number 447)<br>(SEQ ID NO: 26) | (EU number 341)<br>GQPREPQVYTLPPSRDNLTKNQVSLT<br>CLVKGFYPSDIAVEWESNGQPENNYK<br>TTPPVLDSDGSFFLYSKLTVDKSRWQ<br>QGNVFSCSVMHEALHNHYTQKSLSLS<br>PGK<br>(EU number 447)<br>(SEQ ID NO: 27) |
| B212 | (EU number 341)<br>GQPREPQVYTLPPSRDELTKNQVSL<br>TCLVKGFYPSDIAVEWESNGQPENN<br>YITTPPVLLSDGSFFLYSKLTVDKS<br>RWQQGNVFSCSVMHEALHNHYTQKS<br>LSLSPGK<br>(EU number 447)<br>(SEQ ID NO: 28) | (EU number 341)<br>GQPREPQVYTLPPSRDELTKNQVSLT<br>CLVKGFYPSDIAVEWESNGQPENNYG<br>TTPPVLGSDGSFFLYSMLTVDKSRWQ<br>QGNVFSCSVMHEALHNHYTQKSLSLS<br>PGK<br>(EU number 447)<br>(SEQ ID NO: 29) |
| B215 | (EU number 341)<br>GQPREPQVYTLPPSRDELTKNQVSL<br>TCLVKGFYPSDIAVEWESNGQPENN<br>YRTTPPVLLSDGSFFLYSRLTVDKS<br>RWQQGNVFSCSVMHEALHNHYTQKS<br>LSLSPGK<br>(EU number 447)<br>(SEQ ID NO: 30) | (EU number 341)<br>GQPREPQVYTLPPSRDELTKNQVSLT<br>CLVKGFYPSDIAVEWESNGQPENNYG<br>TTPPVLWSDGSFFLYSMLTVDKSRWQ<br>QGNVFSCSVMHEALHNHYTQKSLSLS<br>PGK<br>(EU number 447)<br>(SEQ ID NO: 31) |
| B235 | (EU number 341)<br>GQPREPQVYTLPPSRDELTKNQVSL<br>TCLVKGFYPSDIAVEWESNGQPENN<br>YCTTPPVLLSDGSFFLYSKLTVDKS<br>RWQQGNVFSCSVMHEALHNHYTQKS<br>LSLSPGK<br>(EU number 447)<br>(SEQ ID NO: 32) | (EU number 341)<br>GQPREPQVYTLPPSRDELTKNQVSLT<br>CLVKGFYPSDIAVEWESNGQPENNYG<br>TTPPVLCSDGSFFLYSMLTVDKSRWQ<br>QGNVFSCSVMHEALHNHYTQKSLSLS<br>PGK<br>(EU number 447)<br>(SEQ ID NO: 33) |
| B239 | (EU number 225)<br>TCPPCPAPELLGGPSVFLFPPKPKD<br>TLMISRTPEVTCVVVDVSHEDPEVK | (EU number 225)<br>TCPPCPAPELLGGPSVFLFPPKPKDT<br>LMISRTPEVTCVVVDVSHEDPEVKFN |

TABLE 16-continued

Sequence information of heterodimer pair of CH3 domain

| Mutant name | CH3A (EU numbering 341~447) | CH3B (EU numbering 341~447) |
|---|---|---|
| | FNWYVDGVEVHNAKTKPREEQYNST YRVVSVLTVLHQDWLNGKEYKCKVS NKALPAPIEKTISKAKGQPREPQVY TLPPSRDELTKNQVSLTCLVKGFYP SDIAVEWESNGQPENNYLTTPPVLL SDGSFFLYSKLTVDKSRWQQGNVFS CSVMHEALHNHYTQKSLSLSPGK (EU number 447) (SEQ ID NO: 34) | WYVDGVEVHNAKTKPREEQYNSTYRV VSVLTVLHQDWLNGKEYKCKVSNKAL PAPIEKTISKAKGQPREPQVYTLPPS RDELTKNQVSLTCLVKGFYPSDIAVE WESNGQPENNYGTTPPVLSSDGSFFL YSMLTVDKSRWQQGNVFSCSVMHEAL HNHYTQKSLSLSPGK (EU number 447) (SEQ ID NO: 35) |
| B240 | (EU number 341) GQPREPQVYTLPPSRDELTKNQVSL TCLVKGFYPSDIAVEWESNGQPENN YSTTPPVLLSDGSFFLYSRLTVDKS RWQQGNVFSCSVMHEALHNHYTQKS LSLSPGK (EU number 447) (SEQ ID NO: 36) | (EU number 341) GQPREPQVYTLPPSRDELTKNQVSLT CLVKGFYPSDIAVEWESNGQPENNYG TTPPVLGSDGSFFLYSMLTVDKSRWQ QGNVFSCSVMHEALHNHYTQKSLSLS PGK (EU number 447) (SEQ ID NO: 37) |
| B256 | (EU number 341) GQPREPQVYTLPPSRDELTKNQVSL TCLVKGFYPSDIAVEWESNGQPENN YNTTPPVLLSDGSFFLYSKLTVDKS RWQQGNVFSCSVMHEALHNHYTQKS LSLSPGK (EU number 447) (SEQ ID NO: 38) | (EU number 341) GQPREPQVYTLPPSRDELTKNQVSLT CLVKGFYPSDIAVEWESNGQPENNYG TTPPVLVSDGSFFLYSMLTVDKSRWQ QGNVFSCSVMHEALHNHYTQKSLSLS PGK (EU number 447) (SEQ ID NO: 39) |
| A107$_{w/oW-VT}$ | (EU number 341) GQPREPQVYTLPPSRDELTKNQVSL TCLVEGFYPSDIAVEWESNGQPENN YKTTPPVLDSDGSFFLYSKLTVDKS RWQQGNVFSCSVMHEALHNHYTQKS LSLSPGK (EU number 447) (SEQ ID NO: 40) | (EU number 341) GQPREPQVYTLPPSRDNLTKNQVSLT CLVKGFYPSDIAVEWESNGQPENNYK TTPPVLDSDGSFFLYSKLTVDKSRWQ QGNVFSCSVMHEALHNHYTQKSLSLS PGK (EU number 447) (SEQ ID NO: 41) |
| A109$_{w/oW-VT}$ | (EU number 341) GQPREPQVYTLPPSRDELTKNQVSL TCLVMGFYPSDIAVEWESNGQPENN YKTTPPVLDSDGSFFLYSKLTVDKS RWQQGNVFSCSVMHEALHNHYTQKS LSLSPGK (EU number 447) (SEQ ID NO: 42) | (EU number 341) GQPREPQVYTLPPSRDMLTKNQVWLT CLVKGFYPSDIAVEWESNGQPENNYK TTPPVLDSDGSFFLYSKLTVDKSRWQ QGNVFSCSVMHEALHNHYTQKSLSLS PGK (EU number 447) (SEQ ID NO: 43) |
| A146$_{w/oW-VT}$ | (EU number 341) GQPREPQVYTLPPSRDELTKNQVSL TCLVDGFYPSDIAVEWESNGQPENN YKTTPPVLDSDGSFFLYSKLTVDKS RWQQGNVFSCSVMHEALHNHYTQKS LSLSPGK (EU number 447) (SEQ ID NO: 44) | (EU number 341) GQPREPQVYTLPPSRDMLTKNQVSLT CLVKGFYPSDIAVEWESNGQPENNYK TTPPVLDSDGSFFLYSKLTVDKSRWQ QGNVFSCSVMHEALHNHYTQKSLSLS PGK (EU number 447) (SEQ ID NO: 45) |
| B168$_{w/oW-VT}$ | (EU number 341) GQPREPQVYTLPPSRDELTKNQVSL TCLVKGFYPSDIAVEWESNGQPENN YKTTPPVLLSDGSFFLYSKLTVDKS RWQQGNVFSCSVMHEALHNHYTQKS LSLSPGK (EU number 447) (SEQ ID NO: 46) | (EU number 341) GQPREPQVYTLPPSRDELTKNQVSLT CLVKGFYPSDIAVEWESNGQPENNYG TTPPVLDSDGSFFLYSMLTVDKSRWQ QGNVFSCSVMHEALHNHYTQKSLSLS PGK (EU number 447) (SEQ ID NO: 47) |
| KiH (Genentech) | (EU number 341) GQPREPQVYTLPPSRDELTKNQVSL SCAVKGFYPSDIAVEWESNGQPENN YKTTPPVLDSDGSFFLVSKLTVDKS RWQQGNVFSCSVMHEALHNHYTQKS LSLSPGK (EU number 447) (SEQ ID NO: 48) | (EU number 341) GQPREPQVYTLPPSRDELTKNQVSLW CLVKGFYPSDIAVEWESNGQPENNYK TTPPVLDSDGSFFLYSKLTVDKSRWQ QGNVFSCSVMHEALHNHYTQKSLSLS PGK (EU number 447) (SEQ ID NO: 49) |
| Hole-Hole (Genentech) | (EU number 341) GQPREPQVYTLPPSRDELTKNQVSL SCAVKGFYPSDIAVEWESNGQPENN | Same as Hole-Hole CH3A |

TABLE 16-continued

Sequence information of heterodimer pair of CH3 domain

| Mutant name | CH3A (EU numbering 341~447) | CH3B (EU numbering 341~447) |
|---|---|---|
| | | YKTTPPVLDSDGSFFLVSKLTVDKS<br>RWQQGNVFSCSVMHEALHNHYTQKS<br>LSLSPGK<br>(EU number 447)<br>(SEQ ID NO: 50) |

TABLE 17

Sequence information of heterodimer pair of CH3 domain

| Mutant name | Fc (including CH3A) (EU numbering 225~447) | Fc (including CH3B) (EU numbering 225~447) |
|---|---|---|
| Wild type | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVKGFYP<br>SDIAVEWESNGQPENNYKTTPPVLD<br>SDGSFFLYSKLTVDKSRWQQGNVFS<br>CSVMHEALHNHYTQKSLSLSPGK<br>(EU number 447)<br>(SEQ ID NO: 51) | Same as Wild type Fc (including CH3A) |
| W-VT | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVKGFYP<br>SDIAVEWESNGQPENNYKTTPPVLD<br>SDGSFFLYSWLTVDKSRWQQGNVFS<br>CSVMHEALHNHYTQKSLSLSPGK<br>(EU number 447)<br>(SEQ ID NO: 52) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDELTKNQVSLTCLVKGFYPSDIAVE<br>WESNGQPENNYKTTPPVLVSDGSFTL<br>YSKLTVDKSRWQQGNVFSCSVMHEAL<br>HNHYTQKSLSLSPGK<br>(EU number 447)<br>(SEQ ID NO: 53) |
| EW-RVT | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTENQVSLTCLVKGFYP<br>SDIAVEWESNGQPENNYKTTPPVLD<br>SDGSFFLYSWLTVDKSRWQQGNVFS<br>CSVMHEALHNHYTQKSLSLSPGK<br>(EU number 447)<br>(SEQ ID NO: 54) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPRVYTLPPS<br>RDELTKNQVSLTCLVKGFYPSDIAVE<br>WESNGQPENNYKTTPPVLVSDGSFTL<br>YSKLTVDKSRWQQGNVFSCSVMHEAL<br>HNHYTQKSLSLSPGK<br>(EU number 447)<br>(SEQ ID NO: 55) |
| A107 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVEGFYP<br>SDIAVEWESNGQPENNYKTTPPVLD<br>SDGSFFLYSWLTVDKSRWQQGNVFS<br>CSVMHEALHNHYTQKSLSLSPGK<br>(EU number 447)<br>(SEQ ID NO: 56) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDNLTKNQVSLTCLVKGFYPSDIAVE<br>WESNGQPENNYKTTPPVLVSDGSFTL<br>YSKLTVDKSRWQQGNVFSCSVMHEAL<br>HNHYTQKSLSLSPGK<br>(EU number 447)<br>(SEQ ID NO: 57) |
| A108 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVEGFYP<br>SDIAVEWESNGQPENNYKTTPPVLD | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDILTKNQVTLTCLVKGFYPSDIAVE<br>WESNGQPENNYKTTPPVLVSDGSFTL |

TABLE 17-continued

Sequence information of heterodimer pair of CH3 domain

| Mutant name | Fc (including CH3A)<br>(EU numbering 225~447) | Fc (including CH3B)<br>(EU numbering 225~447) |
|---|---|---|
| | SDGSFFLYSWLTVDKSRWQQGNVFS<br>CSVMHEALHNHYTQKSLSLSPGK<br>(EU number 447)<br>(SEQ ID NO: 58) | YSKLTVDKSRWQQGNVFSCSVMHEAL<br>HNHYTQKSLSLSPGK<br>(EU number 447)<br>(SEQ ID NO: 59) |
| A109 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVMGFYP<br>SDIAVEWESNGQPENNYKTTPPVLD<br>SDGSFFLYSWLTVDKSRWQQGNVFS<br>CSVMHEALHNHYTQKSLSLSPGK<br>(EU number 447)<br>(SEQ ID NO: 60) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDMLTKNQVWLTCLVKGFYPSDIAVE<br>WESNGQPENNYKTTPPVLVSDGSFTL<br>YSKLTVDKSRWQQGNVFSCSVMHEAL<br>HNHYTQKSLSLSPGK<br>(EU number 447)<br>(SEQ ID NO: 61) |
| A146 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVDGFYP<br>SDIAVEWESNGQPENNYKTTPPVLD<br>SDGSFFLYSWLTVDKSRWQQGNVFS<br>CSVMHEALHNHYTQKSLSLSPGK<br>(EU number 447)<br>(SEQ ID NO: 62) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDMLTKNQVSLTCLVKGFYPSDIAVE<br>WESNGQPENNYKTTPPVLVSDGSFTL<br>YSKLTVDKSRWQQGNVFSCSVMHEAL<br>HNHYTQKSLSLSPGK<br>(EU number 447)<br>(SEQ ID NO: 63) |
| B121 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVKGFYP<br>SDIAVEWESNGQPENNYKTTPPVLE<br>SDGSFFLYSWLTVDKSRWQQGNVFS<br>CSVMHEALHNHYTQKSLSLSPGK<br>(EU number 447)<br>(SEQ ID NO: 64) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDELTKNQVSLTCLVKGFYPSDIAVE<br>WESNGQPENNYETTPPVLVSDGSFTL<br>YSKLTVDKSRWQQGNVFSCSVMHEAL<br>HNHYTQKSLSLSPGK<br>(EU number 447)<br>(SEQ ID NO: 65) |
| B135 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVKGFYP<br>SDIAVEWESNGQPENNYKTTPPVLL<br>SDGSFFLYSWLTVDKSRWQQGNVFS<br>CSVMHEALHNHYTQKSLSLSPGK<br>(EU number 447)<br>(SEQ ID NO: 66) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDELTKNQVSLTCLVKGFYPSDIAVE<br>WESNGQPENNYSTTPPVLVSDGSFTL<br>YSLLTVDKSRWQQGNVFSCSVMHEAL<br>HNHYTQKSLSLSPGK<br>(EU number 447)<br>(SEQ ID NO: 67) |
| B168 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVKGFYP<br>SDIAVEWESNGQPENNYKTTPPVLL<br>SDGSFFLYSWLTVDKSRWQQGNVFS<br>CSVMHEALHNHYTQKSLSLSPGK<br>(EU number 447)<br>(SEQ ID NO: 68) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDELTKNQVSLTCLVKGFYPSDIAVE<br>WESNGQPENNYGTTPPVLVSDGSFTL<br>YSMLTVDKSRWQQGNVFSCSVMHEAL<br>HNHYTQKSLSLSPGK<br>(EU number 447)<br>(SEQ ID NO: 69) |
| A205 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL |

TABLE 17-continued

Sequence information of heterodimer pair of CH3 domain

| Mutant name | Fc (including CH3A)<br>(EU numbering 225~447) | Fc (including CH3B)<br>(EU numbering 225~447) |
|---|---|---|
| | NKALPAPIEKTISKAKGQPREPQVY<br>TLPPSRDDLTKNQVWLTCLVEGFYP<br>SDIAVEWESNGQPENNYKTTPPVLD<br>SDGSFFLYSKLTVDKSRWQQGNVFS<br>CSVMHEALHNHYTQKSLSLSPGK<br>(EU number 447)<br>(SEQ ID NO: 70) | PAPIEKTISKAKGQPREPQVYTLPPS<br>RDNLTKNQVSLTCLVRGFYPSDIAVE<br>WESNGQPENNYKTTPPVLDSDGSFFL<br>YSKLTVDKSRWQQGNVFSCSVMHEAL<br>HNHYTQKSLSLSPGK<br>(EU number 447)<br>(SEQ ID NO: 71) |
| A210 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDALTKNQVYLTCLVEGFYP<br>SDIAVEWESNGQPENNYKTTPPVLD<br>SDGSFFLYSKLTVDKSRWQQGNVFS<br>CSVMHEALHNHYTQKSLSLSPGK<br>(EU number 447)<br>(SEQ ID NO: 72) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDNLTKNQVSLTCLVHGFYPSDIAVE<br>WESNGQPENNYKTTPPVLDSDGSFFL<br>YSKLTVDKSRWQQGNVFSCSVMHEAL<br>HNHYTQKSLSLSPGK<br>(EU number 447)<br>(SEQ ID NO: 73) |
| A216 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDGLTKNQVWLTCLVEGFYP<br>SDIAVEWESNGQPENNYKTTPPVLD<br>SDGSFFLYSKLTVDKSRWQQGNVFS<br>CSVMHEALHNHYTQKSLSLSPGK<br>(EU number 447)<br>(SEQ ID NO: 74) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDNLTKNQVSLTCLVKGFYPSDIAVE<br>WESNGQPENNYKTTPPVLDSDGSFFL<br>YSKLTVDKSRWQQGNVFSCSVMHEAL<br>HNHYTQKSLSLSPGK<br>(EU number 447)<br>(SEQ ID NO: 75) |
| A241 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDNLTKNQVWLTCLVEGFYP<br>SDIAVEWESNGQPENNYKTTPPVLD<br>SDGSFFLYSKLTVDKSRWQQGNVFS<br>CSVMHEALHNHYTQKSLSLSPGK<br>(EU number 447)<br>(SEQ ID NO: 76) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDNLTKNQVSLTCLVKGFYPSDIAVE<br>WESNGQPENNYKTTPPVLDSDGSFFL<br>YSKLTVDKSRWQQGNVFSCSVMHEAL<br>HNHYTQKSLSLSPGK<br>(EU number 447)<br>(SEQ ID NO: 77) |
| B212 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVKGFYP<br>SDIAVEWESNGQPENNYITTPPVLL<br>SDGSFFLYSKLTVDKSRWQQGNVFS<br>CSVMHEALHNHYTQKSLSLSPGK<br>(EU number 447)<br>(SEQ ID NO: 78) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDELTKNQVSLTCLVKGFYPSDIAVE<br>WESNGQPENNYGTTPPVLGSDGSFFL<br>YSMLTVDKSRWQQGNVFSCSVMHEAL<br>HNHYTQKSLSLSPGK<br>(EU number 447)<br>(SEQ ID NO: 79) |
| B215 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVKGFYP<br>SDIAVEWESNGQPENNYRTTPPVLL<br>SDGSFFLYSRLTVDKSRWQQGNVFS<br>CSVMHEALHNHYTQKSLSLSPGK<br>(EU number 447)<br>(SEQ ID NO: 80) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDELTKNQVSLTCLVKGFYPSDIAVE<br>WESNGQPENNYGTTPPVLWSDGSFFL<br>YSMLTVDKSRWQQGNVFSCSVMHEAL<br>HNHYTQKSLSLSPGK<br>(EU number 447)<br>(SEQ ID NO: 81) |
| B235 | (EU number 225)<br>TCPPCPAPELLGGPSVFLFPPKPKD | (EU number 225)<br>TCPPCPAPELLGGPSVFLFPPKPKDT |

TABLE 17-continued

Sequence information of heterodimer pair of CH3 domain

| Mutant name | Fc (including CH3A) (EU numbering 225~447) | Fc (including CH3B) (EU numbering 225~447) |
|---|---|---|
| | TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVKGFYP<br>SDIAVEWESNGQPENNYCTTPPVLL<br>SDGSFFLYSKLTVDKSRWQQGNVFS<br>CSVMHEALHNHYTQKSLSLSPGK<br>(EU number 447)<br>(SEQ ID NO: 82) | LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDELTKNQVSLTCLVKGFYPSDIAVE<br>WESNGQPENNYGTTPPVLCSDGSFFL<br>YSMLTVDKSRWQQGNVFSCSVMHEAL<br>HNHYTQKSLSLSPGK<br>(EU number 447)<br>(SEQ ID NO: 83) |
| B239 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVKGFYP<br>SDIAVEWESNGQPENNYLTTPPVLL<br>SDGSFFLYSKLTVDKSRWQQGNVFS<br>CSVMHEALHNHYTQKSLSLSPGK<br>(EU number 447)<br>(SEQ ID NO: 84) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDELTKNQVSLTCLVKGFYPSDIAVE<br>WESNGQPENNYGTTPPVLSSDGSFFL<br>YSMLTVDKSRWQQGNVFSCSVMHEAL<br>HNHYTQKSLSLSPGK<br>(EU number 447)<br>(SEQ ID NO: 85) |
| B240 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVKGFYP<br>SDIAVEWESNGQPENNYSTTPPVLL<br>SDGSFFLYSRLTVDKSRWQQGNVFS<br>CSVMHEALHNHYTQKSLSLSPGK<br>(EU number 447)<br>(SEQ ID NO: 86) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDELTKNQVSLTCLVKGFYPSDIAVE<br>WESNGQPENNYGTTPPVLGSDGSFFL<br>YSMLTVDKSRWQQGNVFSCSVMHEAL<br>HNHYTQKSLSLSPGK<br>(EU number 447)<br>(SEQ ID NO: 87) |
| B256 | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVKGFYP<br>SDIAVEWESNGQPENNYNTTPPVLL<br>SDGSFFLYSKLTVDKSRWQQGNVFS<br>CSVMHEALHNHYTQKSLSLSPGK<br>(EU number 447)<br>(SEQ ID NO: 88) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDELTKNQVSLTCLVKGFYPSDIAVE<br>WESNGQPENNYGTTPPVLVSDGSFFL<br>YSMLTVDKSRWQQGNVFSCSVMHEAL<br>HNHYTQKSLSLSPGK<br>(EU number 447)<br>(SEQ ID NO: 89) |
| A107$_{w/oW\text{-}VT}$ | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVEGFYP<br>SDIAVEWESNGQPENNYKTTPPVLD<br>SDGSFFLYSKLTVDKSRWQQGNVFS<br>CSVMHEALHNHYTQKSLSLSPGK<br>(EU number 447)<br>(SEQ ID NO: 90) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDNLTKNQVSLTCLVKGFYPSDIAVE<br>WESNGQPENNYKTTPPVLDSDGSFFL<br>YSKLTVDKSRWQQGNVFSCSVMHEAL<br>HNHYTQKSLSLSPGK<br>(EU number 447)<br>(SEQ ID NO: 91) |
| A109$_{w/oW\text{-}VT}$ | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVMGFYP<br>SDIAVEWESNGQPENNYKTTPPVLD<br>SDGSFFLYSKLTVDKSRWQQGNVFS<br>CSVMHEALHNHYTQKSLSLSPGK<br>(EU number 447)<br>(SEQ ID NO: 92) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDMLTKNQVWLTCLVKGFYPSDIAVE<br>WESNGQPENNYKTTPPVLDSDGSFFL<br>YSKLTVDKSRWQQGNVFSCSVMHEAL<br>HNHYTQKSLSLSPGK<br>(EU number 447)<br>(SEQ ID NO: 93) |

TABLE 17-continued

Sequence information of heterodimer pair of CH3 domain

| Mutant name | Fc (including CH3A)<br>(EU numbering 225~447) | Fc (including CH3B)<br>(EU numbering 225~447) |
|---|---|---|
| A146$_{w/oW-VT}$ | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVDGFYP<br>SDIAVEWESNGQPENNYKTTPPVLD<br>SDGSFFLYSKLTVDKSRWQQGNVFS<br>CSVMHEALHNHYTQKSLSLSPGK<br>(EU number 447)<br>(SEQ ID NO: 94) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDMLTKNQVSLTCLVKGFYPSDIAVE<br>WESNGQPENNYKTTPPVLDSDGSFFL<br>YSKLTVDKSRWQQGNVFSCSVMHEAL<br>HNHYTQKSLSLSPGK<br>(EU number 447)<br>(SEQ ID NO: 95) |
| B168$_{w/oW-VT}$ | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLTCLVKGFYP<br>SDIAVEWESNGQPENNYKTTPPVLL<br>SDGSFFLYSKLTVDKSRWQQGNVFS<br>CSVMHEALHNHYTQKSLSLSPGK<br>(EU number 447)<br>(SEQ ID NO: 96) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDELTKNQVSLTCLVKGFYPSDIAVE<br>WESNGQPENNYGTTPPVLDSDGSFFL<br>YSMLTVDKSRWQQGNVFSCSVMHEAL<br>HNHYTQKSLSLSPGK<br>(EU number 447)<br>(SEQ ID NO: 97) |
| KiH<br>(Genentech) | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLSCAVKGFYP<br>SDIAVEWESNGQPENNYKTTPPVLD<br>SDGSFFLVSKLTVDKSRWQQGNVFS<br>CSVMHEALHNHYTQKSLSLSPGK<br>(EU number 447)<br>(SEQ ID NO: 98) | (EU number 225)<br>TCPPCPAPELLGGPSVFLFPPKPKDT<br>LMISRTPEVTCVVVDVSHEDPEVKFN<br>WYVDGVEVHNAKTKPREEQYNSTYRV<br>VSVLTVLHQDWLNGKEYKCKVSNKAL<br>PAPIEKTISKAKGQPREPQVYTLPPS<br>RDELTKNQVSLWCLVKGFYPSDIAVE<br>WESNGQPENNYKTTPPVLDSDGSFFL<br>YSKLTVDKSRWQQGNVFSCSVMHEAL<br>HNHYTQKSLSLSPGK<br>(EU number 447)<br>(SEQ ID NO: 99) |
| Hole-Hole<br>(Genentech) | (EU number 225)<br>TCPPCPAPELLGGPSVFLFPPKPKD<br>TLMISRTPEVTCVVVDVSHEDPEVK<br>FNWYVDGVEVHNAKTKPREEQYNST<br>YRVVSVLTVLHQDWLNGKEYKCKVS<br>NKALPAPIEKTISKAKGQPREPQVY<br>TLPPSRDELTKNQVSLSCAVKGFYP<br>SDIAVEWESNGQPENNYKTTPPVLD<br>SDGSFFLVSKLTVDKSRWQQGNVFS<br>CSVMHEALHNHYTQKSLSLSPGK<br>(EU number 447)<br>(SEQ ID NO: 100) | Same as Hole-Hole Fc<br>(including CH3A) |

Sequence information of heterodimer pair of CH3 domain

INDUSTRIAL APPLICABILITY

A system for evaluating a formation ability of a heterodimeric heavy chain according to the present disclosure is manufactured using a yeast cell surface expression system, and the system may be used to perform high speed selection of a mutant in which formation ability of the heterodimer heavy chain is preferred.

In addition, the human antibody heterodimeric heavy chain constant region library according to the present disclosure is obtained by introducing different mutations into each CH3 domain simultaneously using yeast mating, and includes mutants in which various kinds of noncovalent bonds are formed on a CH3 domain interaction surface.

In addition, the CH3 domain mutant pair of the heavy chain constant region of the human antibody according to the present disclosure is produced through high speed line of the human antibody heterodimeric heavy chain constant region library, wherein formation of a homodimer may be minimized, a yield of heterodimer formation may be high as 80 to 95% or more. The heterodimeric heavy chain constant region pair protein produced by using the CH3 domain mutant pair may have similar or improved characteristics, such as expression, production yield, and thermodynamic stability, as compared to those of the wild-type antibody at the time of expression production in animal cells.

In addition, the heterodimeric heavy chain constant region pair protein produced by using the CH3 domain mutant pair of the heavy chain constant region of the human antibody according to the present disclosure is advantageous in that an intrinsic function of a heavy chain constant region (Fc) possessed by the wild type antibody, i.e., a binding ability to FcRn (neonatal Fc receptor) is maintained to have a long serum half-life in blood, and binding sites (protein A and protein G) are conserved in a purification process.

In addition, the heterodimeric heavy chain constant region pair protein produced using the CH3 domain mutant pair of the heavy chain constant region of the human antibody according to the present disclosure does not independently express each CH3 mutant and synthesize each CH3 mutant again, but simultaneously expresses each CH3 mutant in one cell, thereby producing the heterodimer heavy chain constant region at a high yield of about 80 to 95% or more.

The above description of the present disclosure is provided for illustrative purposes, and it will be understood to those skilled in the art that the exemplary embodiments can be easily modified into various forms without changing the technical spirit or essential features of the present disclosure. Accordingly, the embodiments described herein are provided by way of example only and should not be construed as being limited.

SEQUENCE LISTING FREE TEXT

Attached as an electronic file.

The invention claimed is:

1. A method for evaluating a formation of a heterodimer comprised of a first CH3 domain and a second CH3 domain, wherein the second CH3 domain has a different amino acid sequence than the first CH3 domain, said method comprising:
   (1) preparing a yeast cell surface expression vector comprising a first nucleotide encoding the first CH3 domain and a yeast extracellular secretion vector comprising a second nucleotide encoding the second CH3 domain;
   (2) transfecting a first yeast with the yeast cell surface expression vector of step (1) and a second yeast which is of a different mating type than from the first yeast with the yeast extracellular secretion vector of step (1), respectively, to obtain transfected yeasts;
   (3) carrying out mating of the thus-obtained transfected yeasts of step (2) to obtain a mated yeast; and
   (4) detecting a presence of the second CH3 domain on a surface of the mated yeast of step (3).

2. The method according to claim 1, wherein the heterodimer comprises following mutations:
   (A1) a substitution of an amino acid at position K370 of the first CH3 domain; and a substitution of an amino acid at position E357 and/or position S364 of the second CH3 domain; or (B1) a substitution of an amino acid at position D399 of the first CH3 domain; and a substitution of an amino acid at position K392 and/or position K409 of the second CH3 domain, wherein the positions are numbered according to the EU index.

3. A library of a plurality of heterodimers comprised of a first CH3 domain and a second CH3 domain which has a different sequence than the first CH3 domain, wherein respective heterodimer of the library comprises the following mutations:

(A1) a substitution of an amino acid at position K370 of the first CH3 domain with glutamic acid (E), methionine (M) or aspartic acid (D); and a substitution of an amino acid at position E357 of the second CH3 domain with asparagine (N), isoleucine (I), or methionine (M) and/or position S364 of the second CH3 domain with threonine (T) or tryptophan (W); or (B1) a substitution of an amino acid at position D399 of the first CH3 domain with glutamic acid (E) or leucine (L); and a substitution of an amino acid at position K392 of the second CH3 domain with glutamic acid (E), serine (S) or glycine (G) and/or position K409 of the second CH3 domain with leucine (L) or methionine (M), wherein the positions are numbered according to the EU index, and wherein the library of the heterodimers are produced by the method of claim 1.

4. A method of preparing a library of heterodimeric pairs of a first CH3 domain and a second CH3 domain which has a different sequence than the first CH3 domain, comprising:

(1') generating (a) a first nucleotide encoding a first mutant CH3 domain containing a substitution of an amino acid at position K370 of the first CH3 domain with glutamic acid (E), methionine (M) or aspartic acid (D) and (b) a second nucleotide encoding a second mutant CH3 domain containing a substitution of an amino acid at position E357 of the second CH3 domain with asparagine (N), isoleucine (I), or methionine (M) and/or position S364 of the second CH3 domain with threonine (T) or tryptophan (W) to provide a library of the first and the second nucleotides; or (1") generating (a) a first nucleotide encoding a first mutant CH3 domain containing a substitution of an amino acid at position D399 of the first CH3 domain with glutamic acid (E) or leucine (L) and (b) a second nucleotide encoding a second mutant CH3 domain comprising a substitution of an amino acid at position EK392 of the second CH3 domain with glutamic acid €, serine (S), or glycine (G) and/or a substitution of amino acid at position K409 of the second CH3 domain with leucine (L) or methionine (M) to provide a library of the first and the second nucleotides;

(2) transfecting yeasts having different mating types with the first nucleotide and the second nucleotide, respectively;

(3) mating the transfected yeasts to give mated yeasts; and (4) culturing the mated yeasts of step (3) to express a library of the heterodimeric pairs comprised of the first mutant CH3 domain and the second mutant CH3 domain.

5. A heterodimer comprising a first CH3 domain and a second CH3 domain, wherein the first CH3 domain and the second CH3 domain comprise the following mutations:

(A1-1) a substitution of an amino acid at position K370 of the first CH3 domain with glutamic acid (E); and a substitution of an amino acid at position E357 of the second CH3 domain with asparagine (N);

(A1-2) a substitution of an amino acid at position K370 of the first CH3 domain with glutamic acid (E); a substitution of an amino acid at position E357 of the second CH3 domain with isoleucine (I); and a substitution of an amino acid at position S364 of the second CH3 domain with threonine (T);

(A1-3) a substitution of an amino acid at position K370 of the first CH3 domain with methionine (M); a substitution of an amino acid at position E357 of the second CH3 domain with methionine (M); and a substitution of an amino acid at position S364 of the second CH3 domain with tryptophan (W);

(A1-4) a substitution of an amino acid at position K370 of the first CH3 domain with aspartic acid (D); and a substitution of an amino acid at position E357 of the second CH3 domain with methionine (M);

(B1-1) a substitution of an amino acid at position D399 of the first CH3 domain with glutamic acid (E); and a substitution of an amino acid at position K392 the second CH3 domain with glutamic acid (E);

(B1-2) a substitution of an amino acid at position D399 of the first CH3 domain with leucine (L); a substitution of an amino acid at position K392 of the second CH3 domain with serine (S); and a substitution of an amino acid at position K409 of the second CH3 domain with leucine (L); or (B1-3) a substitution of an amino acid at position D399 of the first CH3 domain with leucine (L); a substitution of an amino acid at position K392 of the second CH3 domain with glycine (G); and a substitution of an amino acid at position K409 of the second CH3 domain with methionine (M), wherein the positions are numbered according to the EU index.

6. The heterodimer according to claim 5, wherein the heterodimer comprises the mutation selected from the group consisting of (A1-1)-(A1-4) and further comprises the following mutations:

a substitute of K409 of the first CH3 domain with tryptophan (W), a substitution of D399 of the second CH3 domain with valine (V), and a substitution of F405 of the second CH3 domain with threonine (T).

7. The heterodimer according to claim 5, wherein the heterodimer comprises the mutation (A1-1) and further comprises the following mutations:

(A2) substitutions of E357 and S364 of the first CH3 domain, wherein the positions are numbered according to the EU index.

8. The heterodimer according to claim 7, wherein the (A2) mutations comprises:

a substitution of E357 of the first CH3 domain with aspartic acid (D), alanine (A), glycine (G), or asparagine (N), and a substitution of S364 of the first CH3 domain with tryptophan (W) or tyrosine (Y), wherein the positions are numbered according to the EU index.

9. The heterodimer according to claim 7, wherein the (A2) mutations are selected from the group consisting of:
(A2-1) a substitution of E357 with aspartic acid (D) and a substitution of S364 with tryptophan (W);
(A2-2) a substitution of E357 with alanine (A) and a substitution of S364 with tyrosine (Y);
(A2-3) a substitution of E357 with glycine (G) and a substitution of S364 with tryptophan (W); and
(A2-4) a substitution of E357 with asparagine (N) and a substitution of S364 with tryptophan (W),
wherein the positions are numbered according to the EU index.

10. The heterodimer according to claim 5, wherein the heterodimer comprises the mutation (B1-3) and further comprises the following mutations:
(B2) a substitution of K392 and/or K409 of the first CH3 domain; and a substitution of D399 of the second CH3 domain,
wherein the positions are numbered according to the EU index.

11. The heterodimer according to claim 10, wherein the (B2) mutations are
a substitution of K392 of the first CH3 domain with isoleucine (I), arginine (R), cysteine (C), leucine (L), serine (S), or asparagine (N); and/or a substitution of K409 of the first CH3 domain with arginine (R); and
a substitution of D399 of the second CH3 domain with glycine (G), tryptophan (W), cysteine (C), serine (S), or valine (V),
wherein the positions are numbered according to the EU index.

12. The heterodimer according to claim 10, wherein the (B2) mutations are selected from the group consisting of:
(B2-1) a substitution of K392 of the first CH3 domain with isoleucine (I) and a substitution of D399 of the second CH3 domain with glycine (G);
(B2-2) a substitution of K392 of the first CH3 domain with arginine (R), a substitution of K409 of the first CH3 domain with arginine (R), and a substitution of D399 of the second CH3 domain with tryptophan (W);
(B2-3) a substitution of K392 of the first CH3 domain with cysteine (C) and a substitution of D399 of the second CH3 domain with cysteine (C);
(B2-4) a substitution of K392 of the first CH3 domain with leucine (L) and a substitution of D399 of the second CH3 domain with serine (S);
(B2-5) a substitution of K392 of the first CH3 domain with serine (S) and a substitution of D399 of the second CH3 domain with glycine (G); and
(B2-6) a substitution of K392 of the first CH3 domain with asparagine (N) and a substitution of D399 of the second CH3 domain with valine (V),
wherein the positions are numbered according to the EU index.

13. The heterodimer according to claim 5, wherein the first CH3 domain and the second CH3 domain are an Fc region of an immunoglobulin selected from the group consisting of IgG, IgM, IgA, IgD and IgE.

14. The heterodimer according to claim 13, wherein the IgG is a human IgG.

15. The heterodimer according to claim 14, wherein the human IgG is selected from the group consisting of IgG1, IgG2, IgG3 and IgG4.

16. A heterodimeric Fc pair comprising the heterodimer according to claim 5.

17. A bispecific antibody comprising the heterodimeric Fc pair according to claim 16.

18. The bispecific antibody according to claim 17, wherein the antibody is selected from the group consisting of scFv-Fc, scIgG(scFab-Fc), (Fv)2-Fc and mAb-Fv.

19. The bispecific antibody according to claim 18, wherein the scFv-Fc has a structure in which two scFvs each having a different antigen specificity from the other, are fused to the N-terminus or C-terminus of the heterodimeric Fc pair.

20. The bispecific antibody according to claim 18, wherein the scIgG(scFab-Fc) has a structure in which two scFabs are fused to the N-terminus of the heterodimeric Fc pair.

21. The bispecific antibody according to claim 18, wherein the (Fv)2-Fc has a structure in which two different antigen-binding Fvs each consisting of a variable region of heavy chain (VH) and a variable region of light chain (VL) are fused to the N-terminus and C-terminus of the heterodimeric Fc pair, respectively.

22. The bispecific antibody according to claim 18, wherein the mAb-Fv is a bispecific variable region-fused monoclonal antibody in which each of single variable antigen-binding domain VH and VL is fused to each of the C-terminus of an IgG heavy chain consisting of the heterodimeric Fc pair.

23. A monovalent antigen-binding antibody comprising the heterodimeric Fc pair of claim 16, wherein the antibody being in a form of Fv-Fc in which a variable region of heavy chain (VH) and a variable region of light chain (VL), which bind to a single antigen, are fused to the N-terminus or C-terminus of the heterodimeric Fc pair, and which is capable of monovalently binding to the single antigen.

24. A fusion protein in a form of Protein-Fc prepared by fusing two different biologically active proteins to the N-terminus or C-terminus of the heterodimeric Fc pair of claim 16.

25. A pharmaceutical composition comprising at least one active ingredient selected from the group consisting of the following (a)-(d):
(a) a heterodimeric Fc pair comprising the heterodimer of the antibody CH3 domain according to claim 5,
(b) a bispecific antibody comprising the heterodimer of the antibody CH3 domain according to claim 5,
(c) a monovalent antigen-binding antibody comprising the heterodimeric Fc pair (a), wherein the antibody being in a form of Fv-Fc in which a variable region of heavy chain (VH) and a variable region of light chain (VL), which bind to a single antigen, are fused to the N-terminus or C-terminus of the heterodimeric Fc pair, and which is capable of monovalently binding to the single antigen, and
(d) a fusion protein in a form of protein-Fc prepared by fusing two different biologically active proteins to the N-terminus or C-terminus of the heterodimeric Fc pair (a).

26. A heterodimer comprising a first CH3 domain and a second CH3 domain, wherein the first CH3 domain comprises substitutions of K370E and K409W, and the second CH3 domain comprises substitutions of E357N, D399V, and F405T.

27. The heterodimer of claim 26, wherein the first CH3 domain and the second CH3 domain are an Fc region of an immunoglobulin selected from the group consisting of IgG, IgM, IgA, IgD and IgE.

28. A heterodimeric Fc pair comprising a first Fc chain comprising a first CH3 domain and a second Fc chain comprising a second CH3 domain, wherein the first CH3 domain and the second CH3 domain are as defined in claim 26.

29. The heterodimeric Fc pair of claim 28, wherein the first Fc chain and/or the second Fc chain are of an IgG.

* * * * *